US006605590B1

(12) United States Patent
Lorbert et al.

(10) Patent No.: US 6,605,590 B1
(45) Date of Patent: Aug. 12, 2003

(54) OLIGOMERS AND OLIGOMERIC SEGMENTS OF ALPHA-HYDROXY CARBOXYLIC ACIDS AND ALPHA-AMINO ACIDS

(75) Inventors: Stephen J. Lorbert, St. Louis, MO (US); Charles S. Schasteen, St. Charles, MO (US); Paul K. S. Nam, Rolla, MO (US); Daniel Forciniti, Rolla, MO (US); Mathur P. Rajesh, Rolla, MO (US); Shubhender Kapila, Rolla, MO (US)

(73) Assignee: Novus International, Inc., St. Louis, MO (US)

( * ) Notice: Subject to any disclaimer, the term of this patent is extended or adjusted under 35 U.S.C. 154(b) by 54 days.

(21) Appl. No.: 09/699,946

(22) Filed: Oct. 30, 2000

Related U.S. Application Data

(60) Provisional application No. 60/162,725, filed on Oct. 29, 1999.

(51) Int. Cl.$^7$ .......................... A23L 1/305; A61K 38/03; C07K 4/00
(52) U.S. Cl. ........................... 514/2; 424/442; 426/648; 426/656; 514/19; 514/562; 514/563; 530/300; 530/345; 562/556; 562/564
(58) Field of Search .................... 424/439, 442; 426/648, 656; 514/2, 19, 562, 563, 625; 530/300, 345; 562/556, 557, 559, 561, 562, 564; 564/201

(56) References Cited

U.S. PATENT DOCUMENTS

| 3,803,327 A | 4/1974 | Fujimaki et al. ............ 426/32 |
| 3,966,985 A | 6/1976 | Jonas ...................... 426/533 |
| 4,116,768 A | 9/1978 | Isowa et al. ............. 435/68.1 |
| 4,119,493 A | 10/1978 | Isowa et al. ............. 435/68.1 |
| 4,172,072 A | 10/1979 | Ashmead .................. 530/345 |
| 4,393,228 A | 7/1983 | Sawada et al. ........... 549/549 |
| 4,701,328 A | 10/1987 | Bercovici et al. ........... 426/2 |
| 4,806,473 A | 2/1989 | Johansen et al. ........ 435/68.1 |
| 4,940,662 A | 7/1990 | Yamazaki et al. ....... 435/68.1 |
| 5,167,957 A | 12/1992 | Webb, Jr. et al. ............ 514/2 |
| 5,304,470 A | 4/1994 | Fischer et al. .......... 435/68.1 |
| 5,374,428 A | 12/1994 | Hansen et al. ............ 424/438 |
| 5,637,766 A | 6/1997 | Hsu et al. ................ 562/512 |
| 5,663,409 A | 9/1997 | Blackburn et al. ........ 558/351 |
| 5,670,332 A | 9/1997 | Kuhl et al. .............. 435/68.1 |
| 5,731,459 A | 3/1998 | Stockhammer et al. ...... 562/37 |

FOREIGN PATENT DOCUMENTS

| EP | 0 031 527 A2 | 7/1981 |
| FR | 2 708 938 A1 | 2/1995 |
| JP | 03 183495 A | 8/1991 |
| JP | 6-316557 | * 11/1994 |
| WO | WO 95/18781 A1 | 7/1995 |
| WO | 98/11126 | * 3/1998 |
| WO | WO01/27074 A1 | 4/2001 |
| WO | WO 01/56980 A1 | 8/2001 |

OTHER PUBLICATIONS

Tobe et al. Synthesis and Structure–Activity Relationships of Amastatin Analogues, Inhibitors of Aminopeptidase A. Agric. Biol. Chem. 1982, vol. 46, No. 7, pp. 1865–1872.*
Chen et al., Quantitative Analyses of Biochemical Kinetic Resolution of Enantiomers. 2. Enzyme–Catalyzed Esterifications in Water–Organic Solvent Biphasic Systems, Journal of the American Chemical Society, 1987, vol. 109, pp. 2812–2817.
Ohya et al., Polycondensation of a–Hydroxy Acids by Enzymes or Peg–Modified Enzymes in Organic Media, Journal of Macromolecular Science, vol. A32, No. 2, 1995, pp. 179–190.
Wallace, et al., Breakdown of N–Terminally Modified Peptides and an Isopeptide by Rumen Microorganisms, Applied and Environmental Microbiology, Sep. 1993, pp. 3147–3149.
Lee, et al., Papain Catalyzed Polymerization of L–α–Amino Acid Methyl Esters with Hydrophobic Side Chains, Chemistry Express, vol. 5, No. 10 pp. 741–744 (1990).
Kashe, e al., Stereo–and Sequence Specificity of Serine Proteases in Peptide Synthesis, Biomed. Biochim. Acta 50 (1991) 10/11, S 38–S 43.
Wang, et al., Cross–Linked Crystals of Substilisin: Versatile Catalyste for Organic Synthesis, The Journal of Organic Chemistry, vol. 62, May 30, 1997, No. 11, 1997, pp. 3488–3495.
Gololobov, et al., Nucleophile Specificity in α–chymotrpsin–and subtilisin–(*Bacillus subtilis* strain 72) Catalyzed Reactions, Biochimica et Biophysica Acta, 1160 (1992) pp. 188–192.
Wallace, et al., Analysis of Peptide Metabolism by Ruminal Microorganisms, Applied and Environmental Microbiology, Sep. 1989, pp. 2372–2376.
Wallace, Amino Acid adn Protein Synthesid, Turnover, and Breakdown by Ruminal Microorganisms, CRC Principles of Protein Nutrition of Ruminants, Chapter 5, pp. 71–111 (1994).
Webb, Jr., et al., Absorption of Amino Acids and Peptides, CRC Principles of Protein Nutrition of Ruminants, Chapter 7, pp. 127–146 (1994).

(List continued on next page.)

*Primary Examiner*—Jeffrey E. Russel
(74) *Attorney, Agent, or Firm*—Senniger, Powers, Leavitt & Roedel

(57) ABSTRACT

An enzymatic synthesis and composition of α-hydroxy carboxylic acid and α-amino acid or peptide co-oligomers is disclosed wherein a residue of the α-hydroxy carboxylic acid is linked to a residue of the α-amino acid or peptide by an amide linkage. Proteolytic enzyme papain catalyzes co-oligomerization of the α-hydroxy carboxylic acid and α-amino acid. The degree and distribution of oligomerization varies upon the type and concentrations of different reaction mixtures utilized and upon the length of allowed reaction time. The resultant oligomers may be provided to ruminants as bioavailable amino acid supplements that are resistant to degradation in the rumen.

22 Claims, 62 Drawing Sheets

OTHER PUBLICATIONS

Sluyterman, L.A. et al.; "Sigmoidal Progress Curves in The Polymerization Of Leucine Methyl Ester Catalyzed By Papain"; *Biochimica Et Biophysica Acta*; vol. 289; vol. E41; pp. 194–202; 1972.

Ohya, Yuichi et al.; "Polycondensation Of Alpha–hydroxy Acids By Enzymes Or PEG–modified Enzymes"; *Journal Of Macromolecular Science A. Pure And Applied Chemistry*; vol. A32; No. 2; pp. 179–190; 1995; Abstract.

Rajesh et al., Synthesis and Characterization of Methionine and 2–Hydroxy–4[methyl thio] Butanoic Acid (HMB) Co–oligomers; University of Missouri–Rolla, Missouri, submitted to J. Chromatography (2000).

Rajesh et al., Synthesis and Characterization of αAcid αAmino Acid and Hetero–Oligomers, University of Missouri–Rolla, Missouri, Pittcom 2001, Mar. 4–9, 2001, New Orleans, LA.

Rajesh et al., Synthesis and Characterization of MHBA–Methionine and MHBA–Lysine Co–oligomers, University of Missouri–Rolla, Missouri, Pittcon 2000, Mar. 12–17, 2000, New Orleans, LA.

Rajesh et al., Synthesis and Characterization of α–Hydroxy Acid and Amino Acid Co–oligomers, University of Missouri–Rolla, Missouri, 19th International Symposium on the Separation and Analysis of Proteins, Peptides and Polynucleotides, Oct. 31–Nov. 3, 1999.

Lozano et al., One–Step Synthesis of Gly–Gly–PheNH$_2$ from N–Unprotected Amino Acid Derivatives by Papain in One–Phase Liquid Media, Biotechnology Letters, vol. 14, No. 10, Oct. 1992, pp. 933–936.

Cerovsky et al., Nucleophile Specificity of Subtilisin in an Organic Solvent with Low Water Content: Investigation via Acyl Transfer Reactions, Biotechnology and Bioengineering, vol. 49, pp. 553–558 (1996).

Lozano et al., Peptide Synthesis by Papain in Alkali Halide Media, Biocatalysis and Biotransformation, vol. 13, pp. 255–269, 1996.

Kasai et al., Correlation between Molecular Weight Distribution of Oligo–L–methionine Prepared by Papain–catalyzed Polymerization and Its Supplementary Effect in a Low Protein Diet, Bioscience, Biotechnology, and Biochemistry, vol. 56, Nov. 1992.

Spindler et al, Amino Acid Anlaysis of Feedstruffs: Determination of Methionine and Cystine after Oxidatin with Performic Acid and Hydrolysis, Journal of Agricultural and Food Chemistry, vol. 32, 1984, pp. 1366–1371.

Yamashita et al, A Novel One–step Process for Enzymatic Incorporation of Amino Acids into Proteins: Application to Soy Protein and Flour for Enhancing Jost et al., Papain Catalyzed Oligomerization of α–Amino Acids. Synthesis and Characterization of Water–Insoluble Oligomers of L–Methionine, Helvetica Chimica Acta, vol. 63, 1980, pp. 375–384.

Ferjancic et al., Papain–Catalyzed Polymerization of Amino Acids in Low Water Organic Solvents, Biotechnology Letters, vol. 13, No. 3, pp. 161–166, 1991.

Wallace et al., Analysis of Peptide Metabolism by Ruminal Microorganisms, Applied and Environmental Microbiology, vol. 55, No. 9, Sep. 1989, pp. 2372–2376.

Wallace, Acetylation of Peptides Inhibits their Degradation by Rumen Micro–Organisms, British Journal of Nutrition, vol. 68, 1992, pp. 365–372.

Wallace, Ruminal Microbial Metabolism of Peptides and Amino Acids, American Institute of Nutrition, 1996, pp. 1326S–1334S.

Kitaguchi et al., Enzymatic Resolution of Racemic Amines: Crucial Role of the Solvent, Journal of the American Chemical Society, vol. 111, 1989, pp. 3094–3095.

Fitzpatrick et al., How Can the Solvent Affect Enzyme Enantioselectivity?, Journal of the American Chemical Society, vol. 113, 1991, pp. 3166–3171.

Arai et al., A Novel One–step Process for Enzymatic Incorporation of Amino Acids into Proteins: Papain–catalyzed Polymerization of L–Methionine Ethyl Ester and Its Regulation by Adding a Protein Substrate, Agricultural and Biological Chemistry, vol. 43, May 1979, pp. 1069–1074.

Ohkubo et al., Catalytic Activity of a Novel Water–Soluble Cross–Linked Polymer Imprinted by a Transition–state Analogue for the Stereoselective Hydrolysis of Enantiomeric Amino Acids Esters, Polymer, vol. 37, No. 17, pp. 3993–3995.

Yamashita et al., Stereoselective Polymerization of α–Amino Acid N–Carboxyanhydrides with Nickel dl–2–Methylbutyrate–Tri–n–butylphosphine Catalyst System, Macromolecules, vol. 7, No. 4, 1974, pp. 410–415.

Nozawa et al., On the Mechanism of the Stereoselective Hydrolysi of Phenylalanine Esters Catalyzed by Poly(L–l–ysine)–Copper(II) Complexes, Die Makromolekulare Chemie, vol. 161, 1972, pp. 289–291.

Itsuno et al., Novel Polymer–Supported Chiral Catalysis for Asymmetric Synthesis, Macromolecular Symposia, vol. 105, Mar. 1996, pp. 155–159.

* cited by examiner

FIG. 1 MALDI-TOF SPECTRA OF METHIONINE OLIGOMERS PAPAIN CATALYZED SYNTHESIS, pH 5.5, 24 HOURS INCUBATION

FIG. 2 MALDI-TOF SPECTRA OF MHBA – METHIONINE OLIGOMERS PAPAIN CATALYZED SYNTHESIS, pH 5.5, 24 HOURS INCUBATION

FIG. 4  HPLC OF MHBA - METHIONINE OLIGOMER SULFONES (10 min Rxn.) CHROMATOGRAPHY OF MHBA-Met CO-OLIGOMER SULFONES, pH 5.5, INCUBATION PERIOD 10 MINUTES.

FIG. 5 HPLC OF MHBA - METHIONINE OLIGOMER SULFONES (24 hrs Rxn.) CHROMATOGRAPHY OF MHBA - Met CO-OLIGOMER SULFONES, pH 5.5, INCUBATION PERIOD 24 HOURS.

RM - LysEE + MHBAEE Co-Olgtn

2-Phase LysEE Olgtn

LysEE + MHBAEE Co-Olgtn in 3 Phase

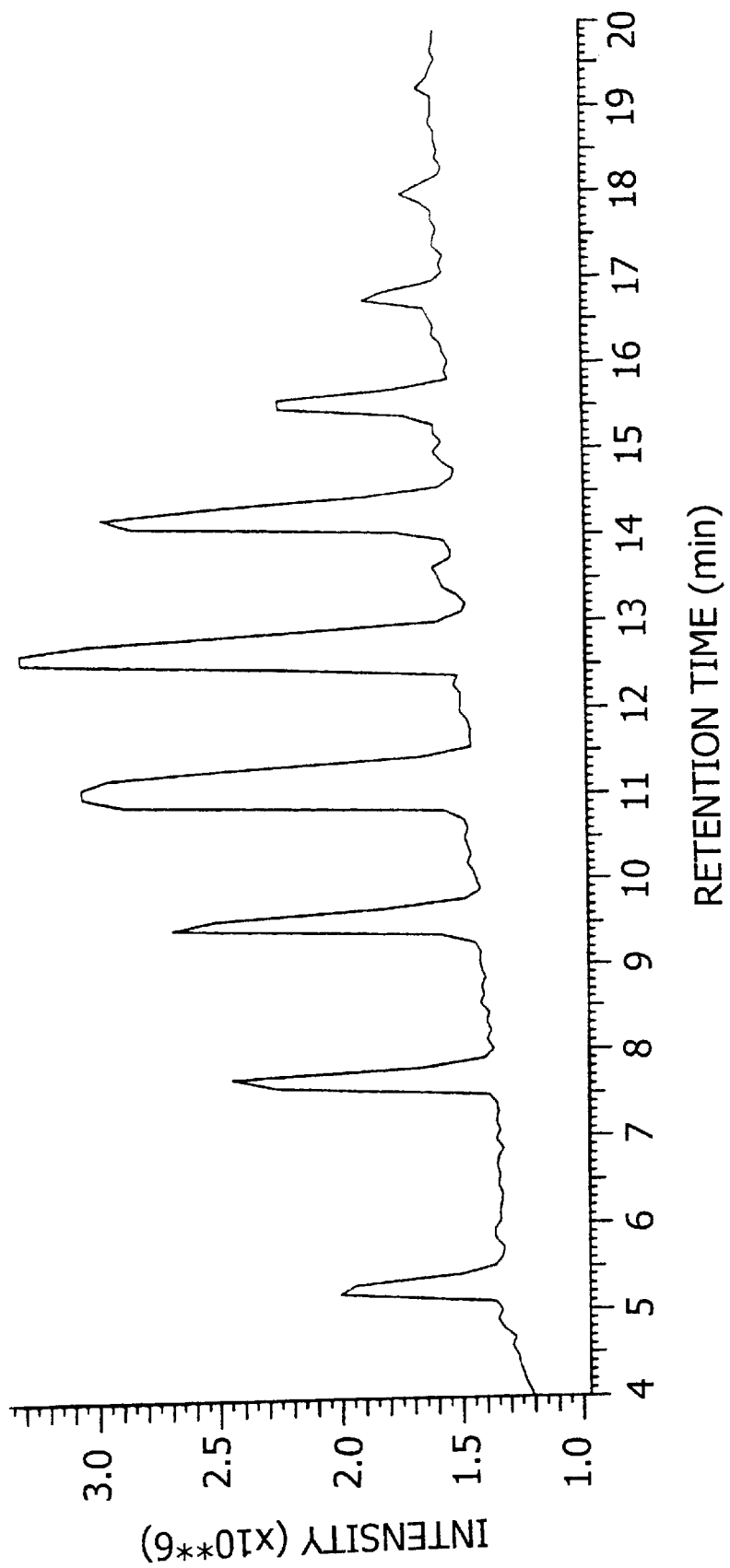
FIG. 14B CHROMATOGRAMS OF PERSULFONATED METHIONINE OLIGOMERS POSITIVE ION TOTAL ION CHROMATOGRAM

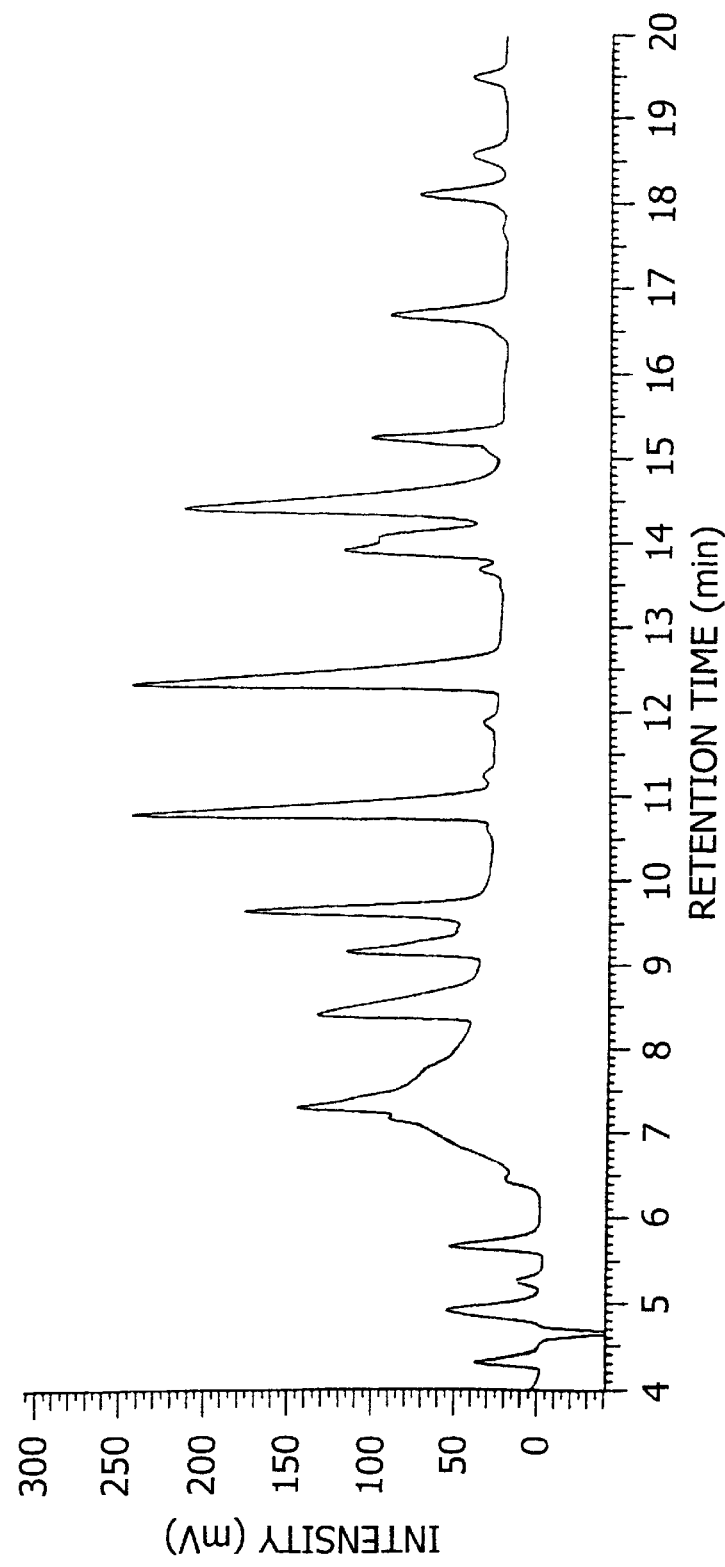
FIG. 15A CHROMATOGRAMS OF PERSULFONATED HMB-METHIONINE CO-OLIGOMERS UV DETECTOR

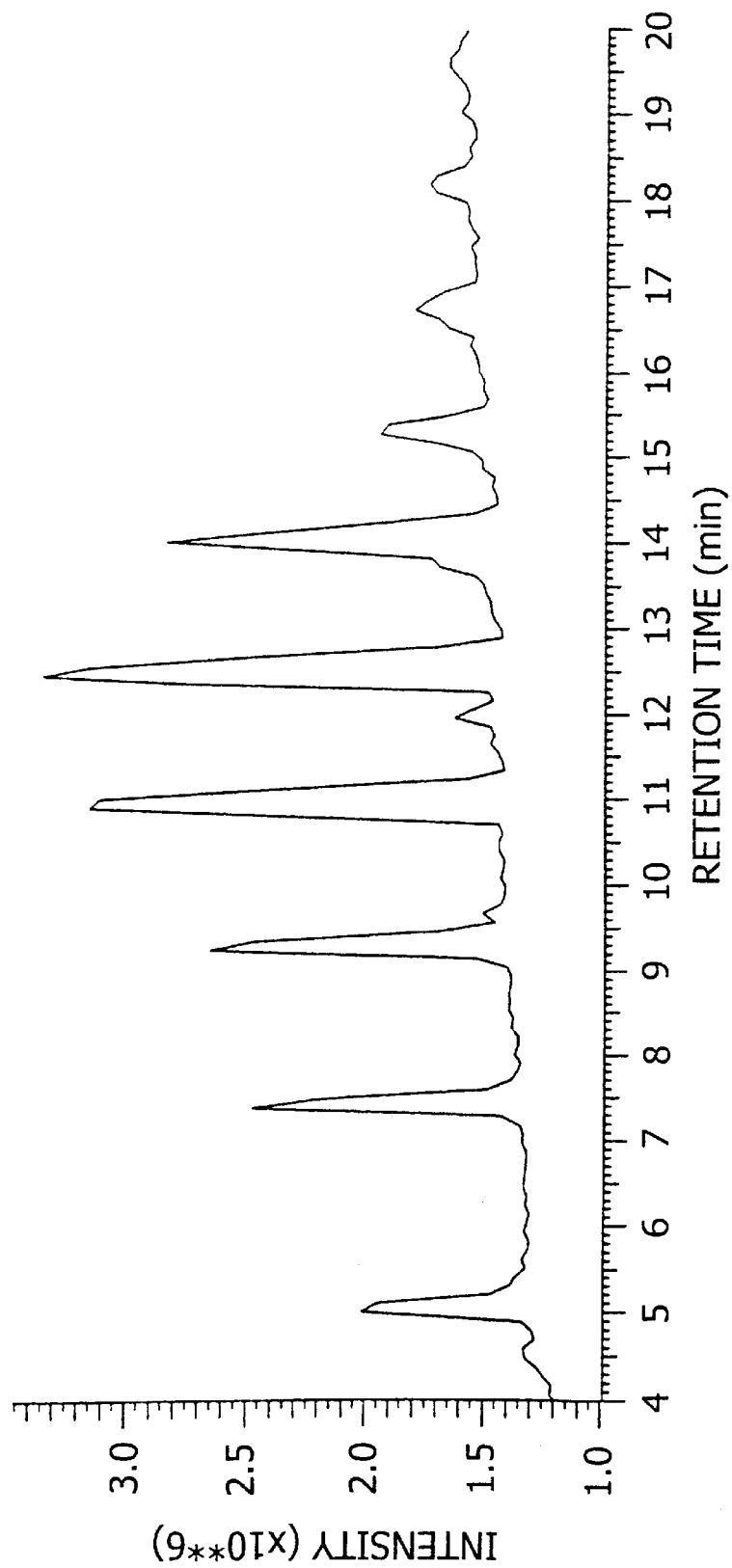
FIG. 15B CHROMATOGRAMS OF PERSULFONATED HMB-METHIONINE CO-OLIGOMERS POSITIVE ION TOTAL ION CHROMATOGRAM POSITIVE ION ESI SPECTRA OF (Met)$_3$ SULFONE PEAK ELUTING AT 5.27 min FIG. 17 POSITIVE ION ESI SPECTRA OF (Met)$_4$ SULFONE PEAK ELUTING AT 7.70 min

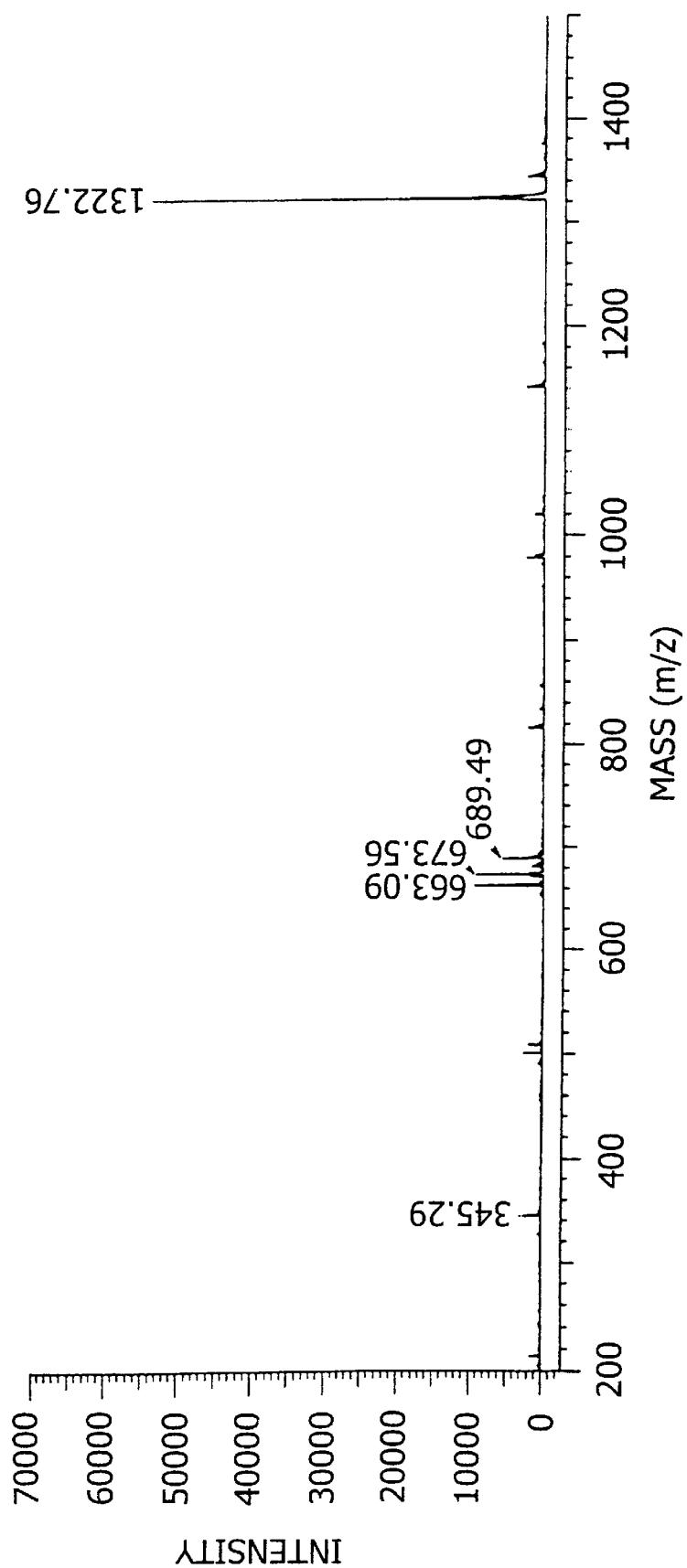
FIG. 20B POSITIVE ION ESI SPECTRA OF (Met)$_8$ SULFONE PEAK ELUTING AT 14.26 min

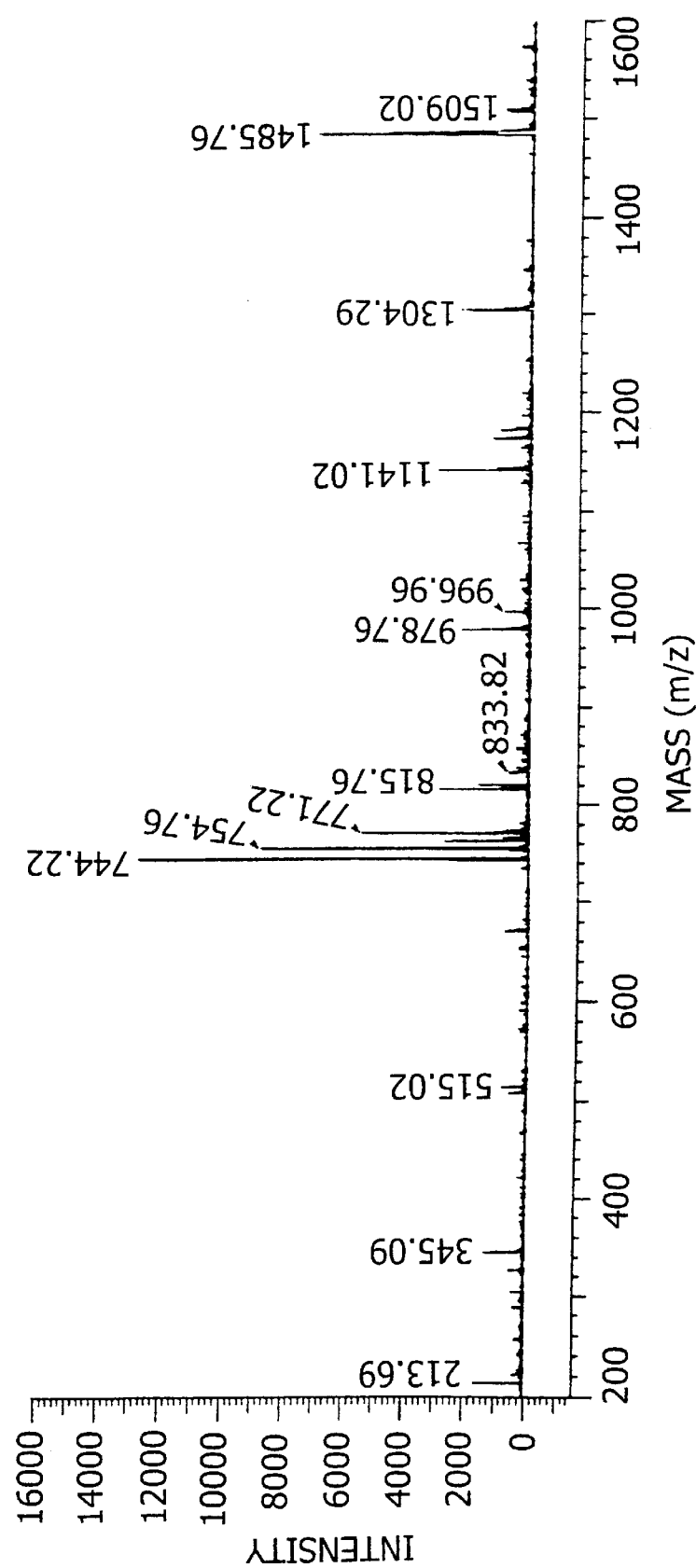
FIG. 20C POSITIVE ION ESI SPECTRA OF (Met)₉ SULFONE PEAK ELUTING AT 15.60 min. THE m/z 744 IS DOUBLY CHARGED (Met)₉

CHROMATOGRAMS OF PERSULFONATED Met OLIGOMERS
UV ABSORPTION DETECTOR

CHROMATOGRAMS OF PERSULFONATED Met OLIGOMERS
TOTAL ION CHROMATOGRAM ESI-NEGATIVE ION

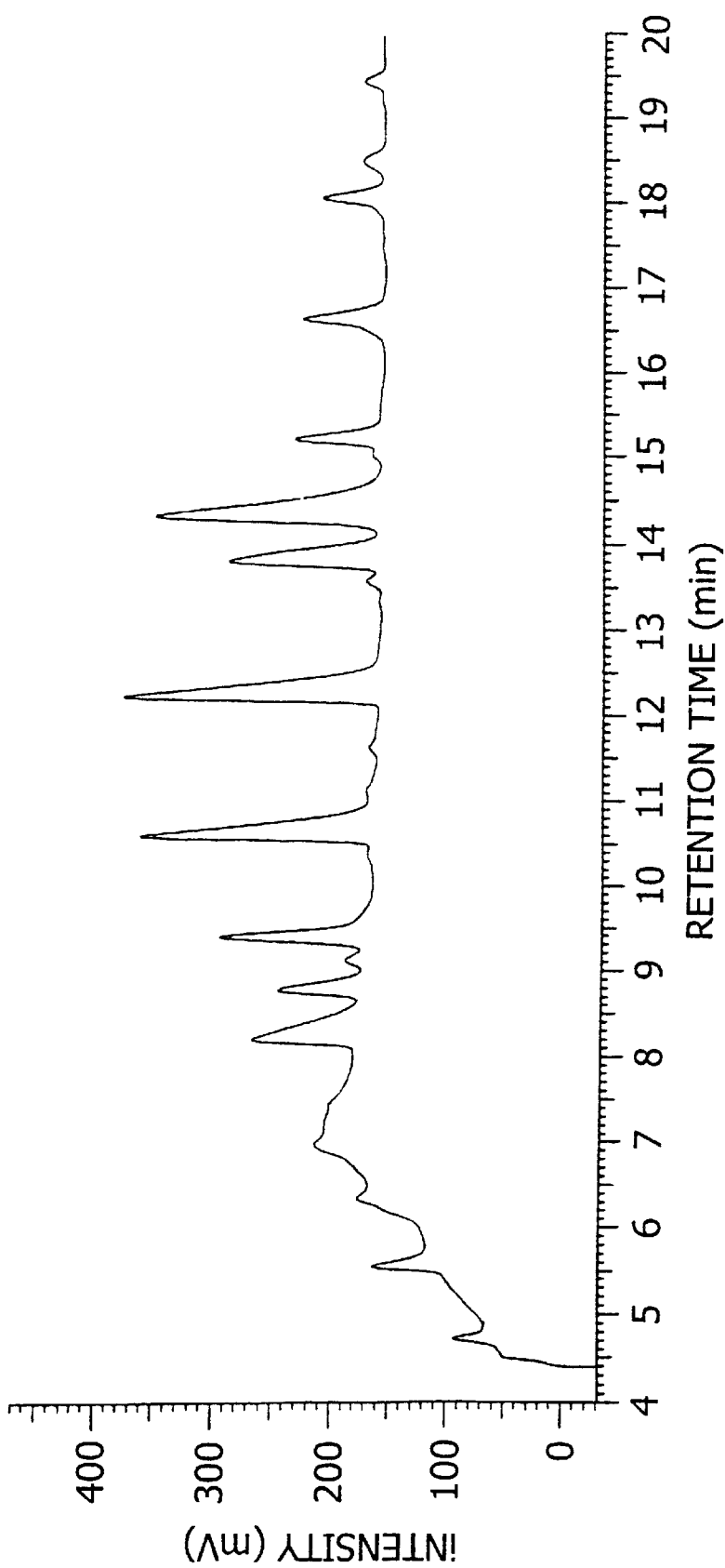
FIG. 22A CHROMATOGRAMS OF PERSULFONATED HMB-Met CO-OLIGOMERS UV ABSORPTION DETECTOR

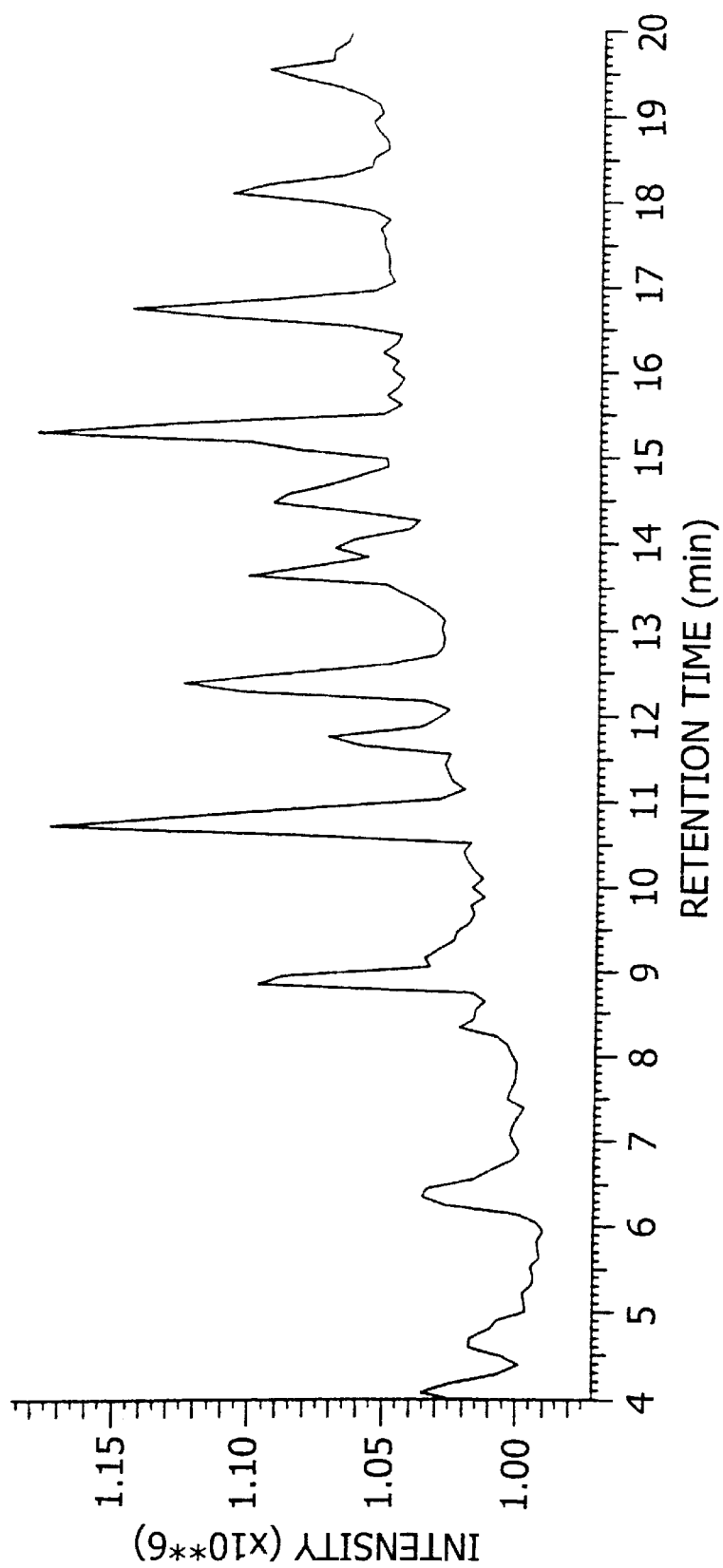
FIG. 22B CHROMATOGRAMS OF PERSULFONATED HMB-Met CO-OLIGOMERS
TOTAL ION CHROMATOGRAM ESI-NEGATIVE ION

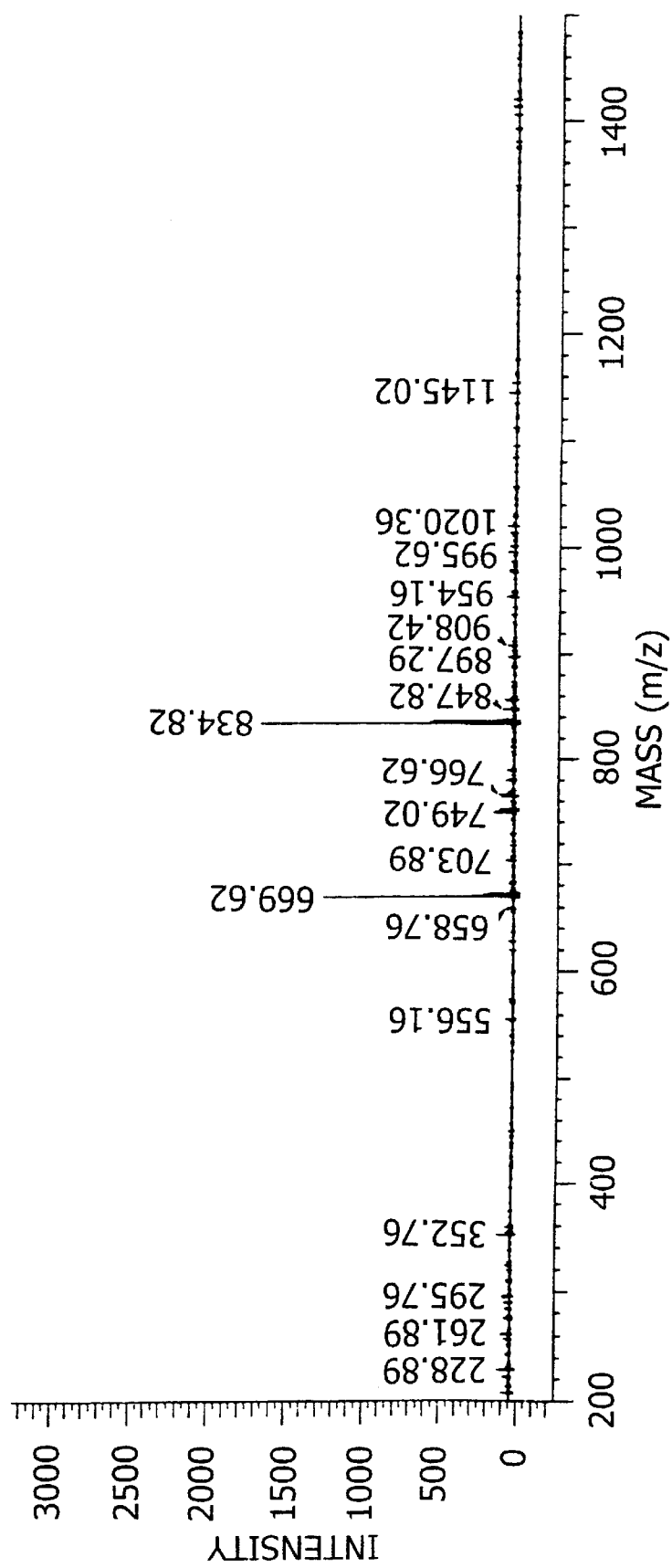
FIG. 23 NEGATIVE ION ESI SPECTRA OF HMB-(Met)$_5$ SULFONE PEAK ELUTING AT 11.57 MIN

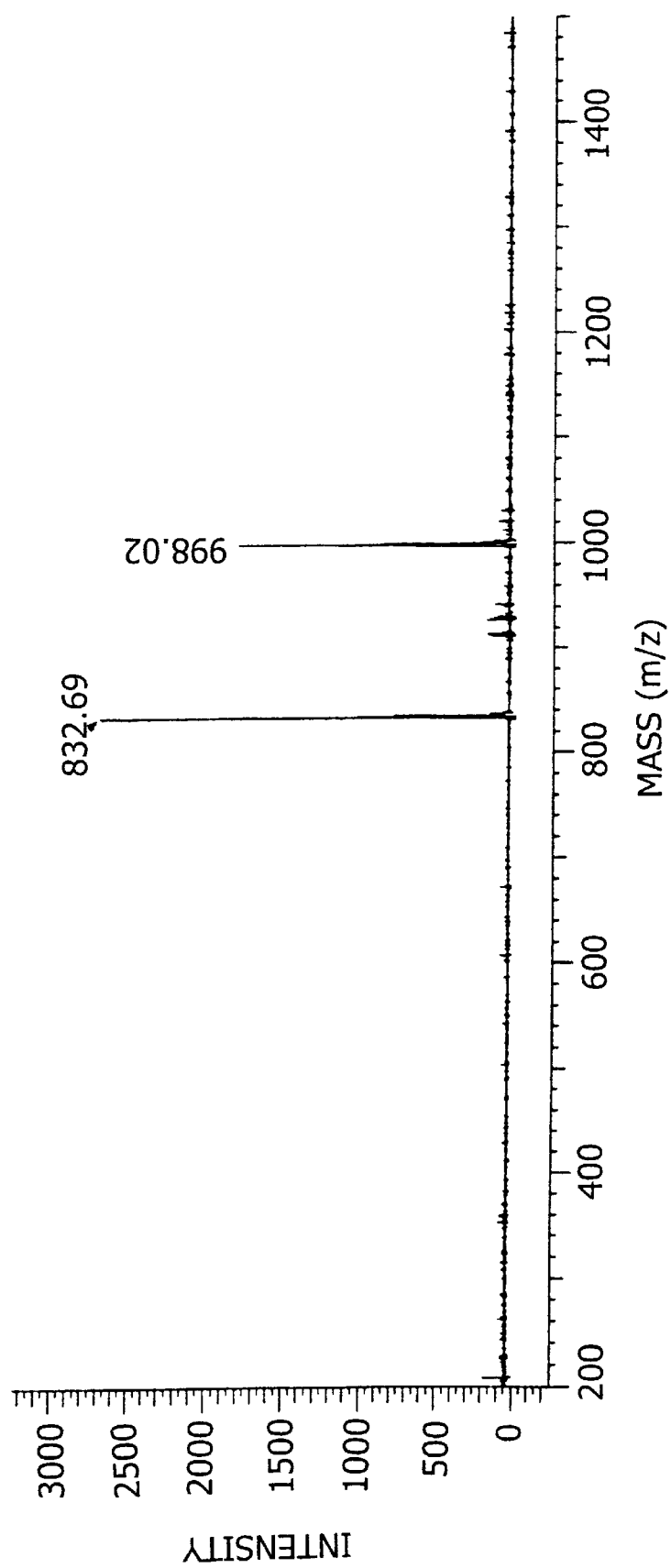
FIG. 24 NEGATIVE ION ESI SPECTRA OF HMB-(Met)$_6$ SULFONE PEAK ELUTING AT 13.86 MIN NEGATIVE ION ESI SPECTRA OF HMB-(Met)$_7$ SULFONE PEAK ELUTING AT 15.31 MIN

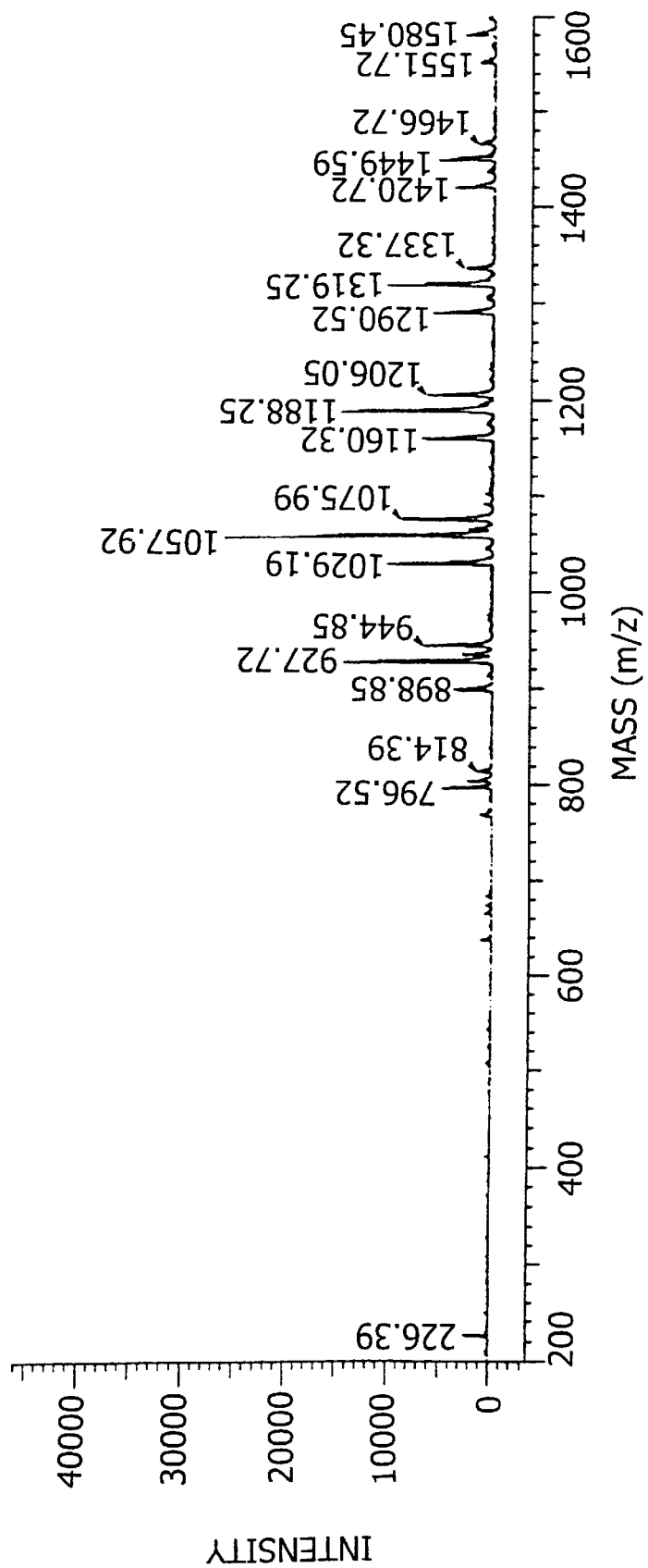
FIG. 28B POSITIVE AND NEGATIVE ESI-MS SPECTRA OF HMB-Met CO-OLIGOMER SYNTHESIS WITH HMB METHYL ESTER AND MetEE

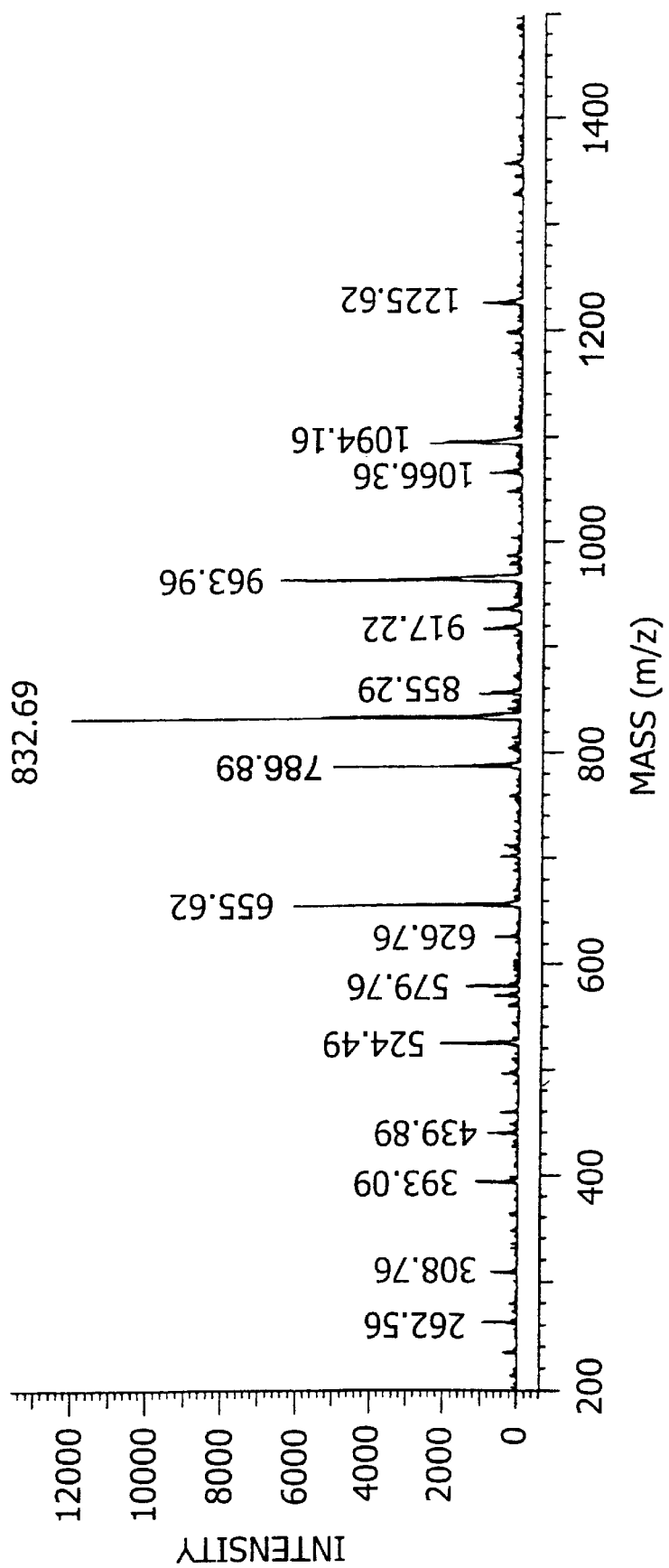
FIG. 29 PARENT ION SSI-MS SPECTRA OF HMB-MET CO-OLIGOMER SYNTHESIZED WITH HMB METHYL ESTER AND MetEE

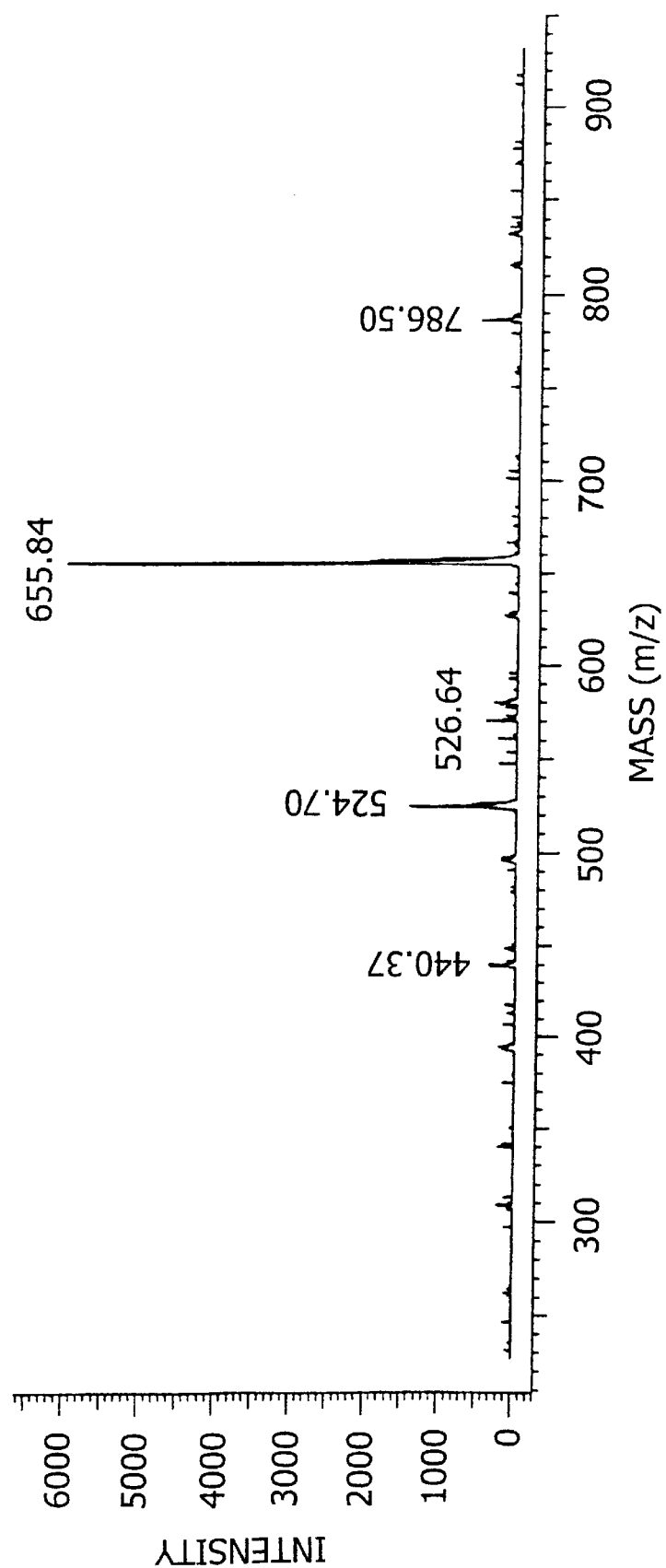
FIG. 30 DAUGHTER ION SPECTRUM OF (Met)$_6$-EE

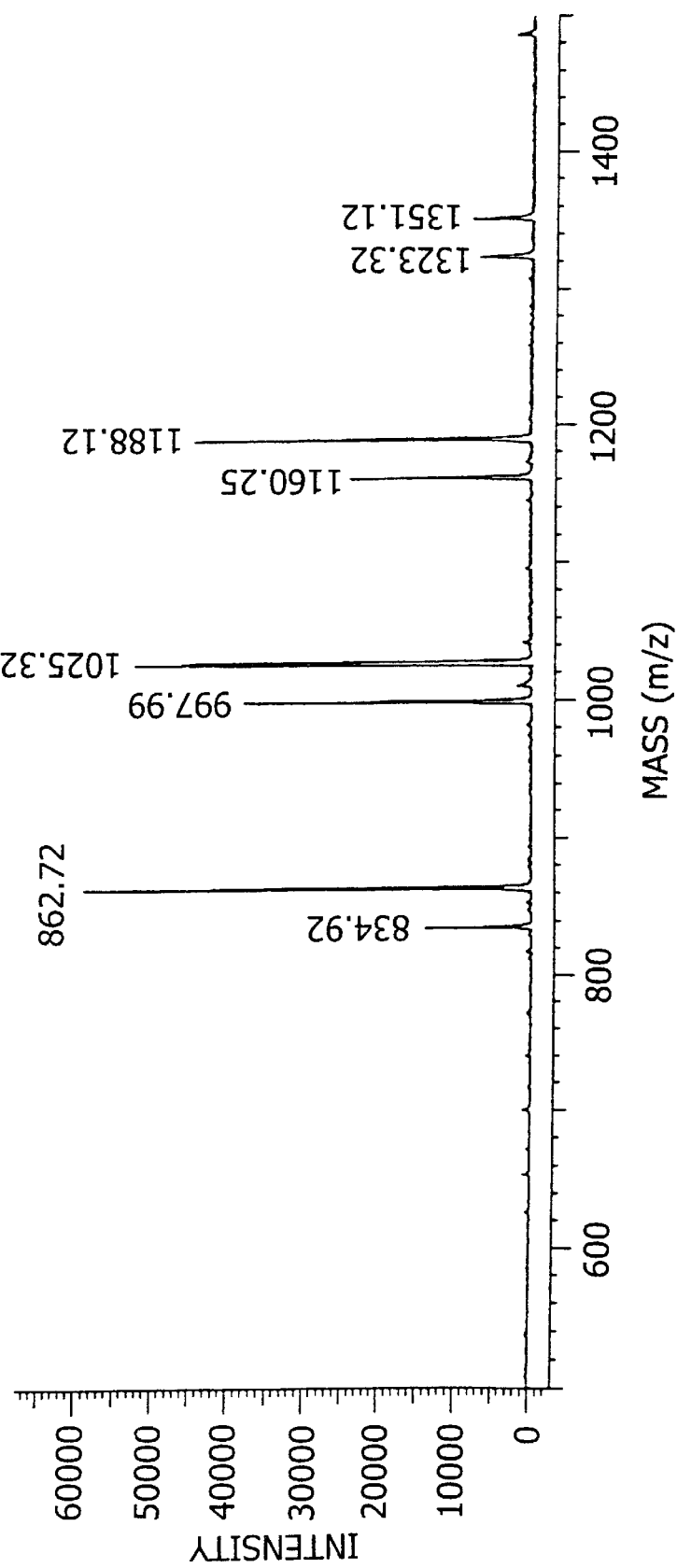
FIG. 31A  POSITIVE ION ESI-MS SPECTRA OF TYROSINE $(Tyr)_n$ OLIGOMERS

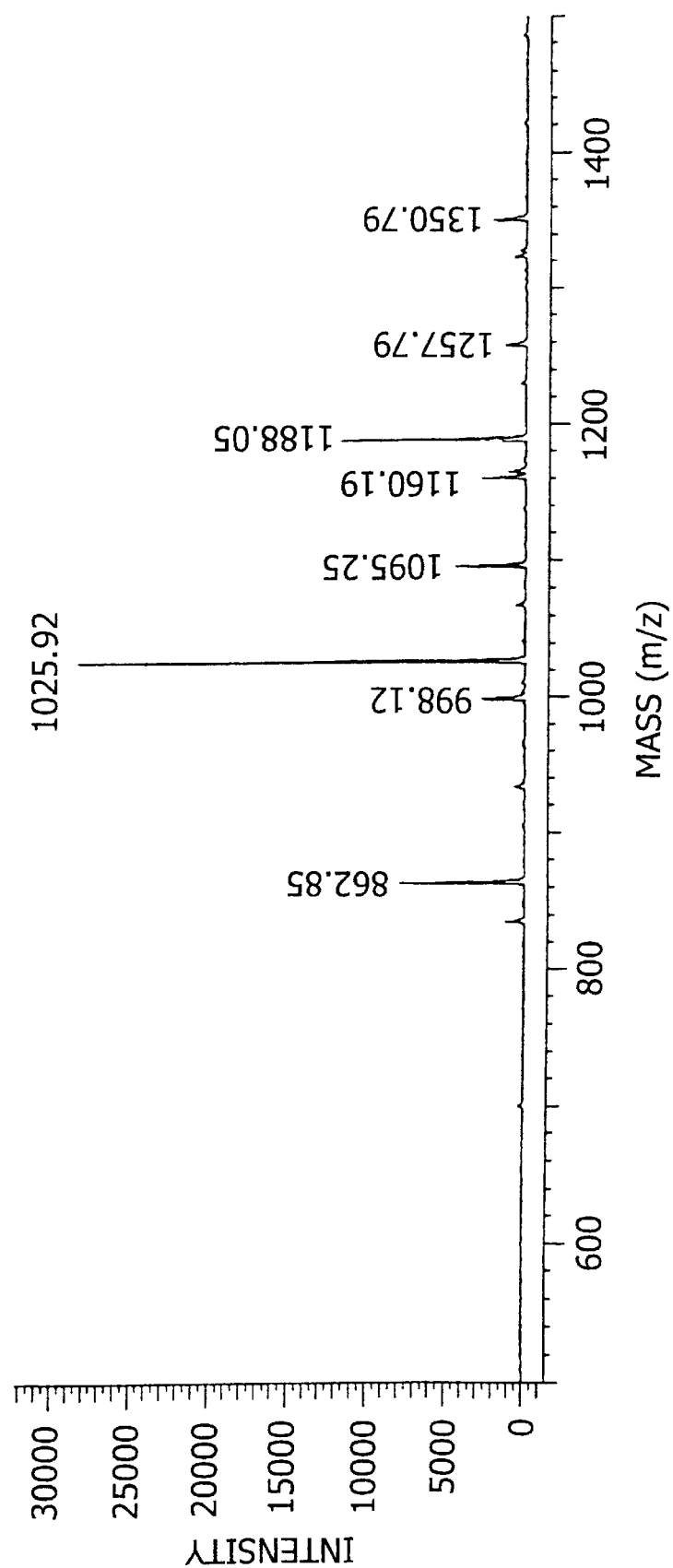
FIG. 32A  MHBA-TYROSINE CO-OLIGOMERS WITH POSITIVE ION SPECTRA

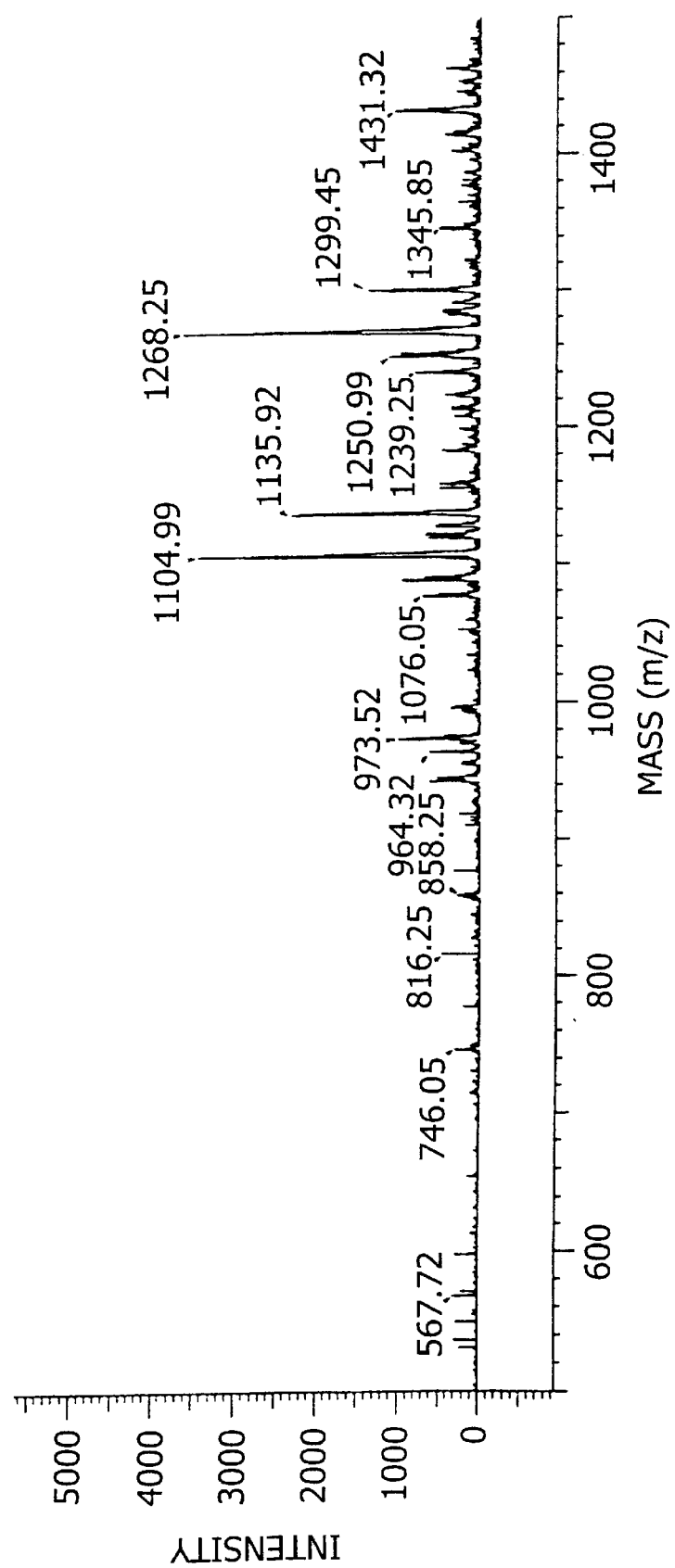
FIG. 32B  MHBA-TYROSINE CO-OLIGOMERS WITH NEGATIVE ION SPECTRA

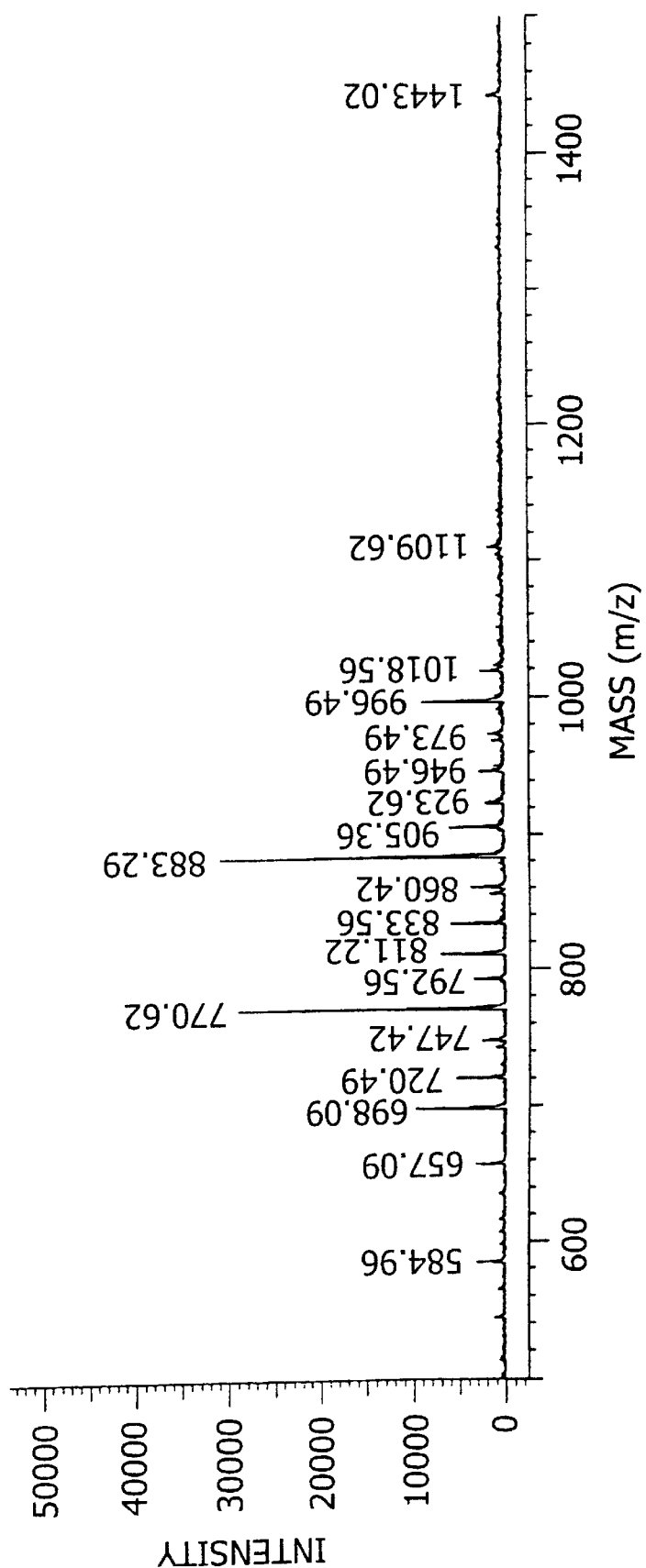
FIG. 33A POSITIVE ION ESI-MS SPECTRA OF LEUCINE OLIGOMERS

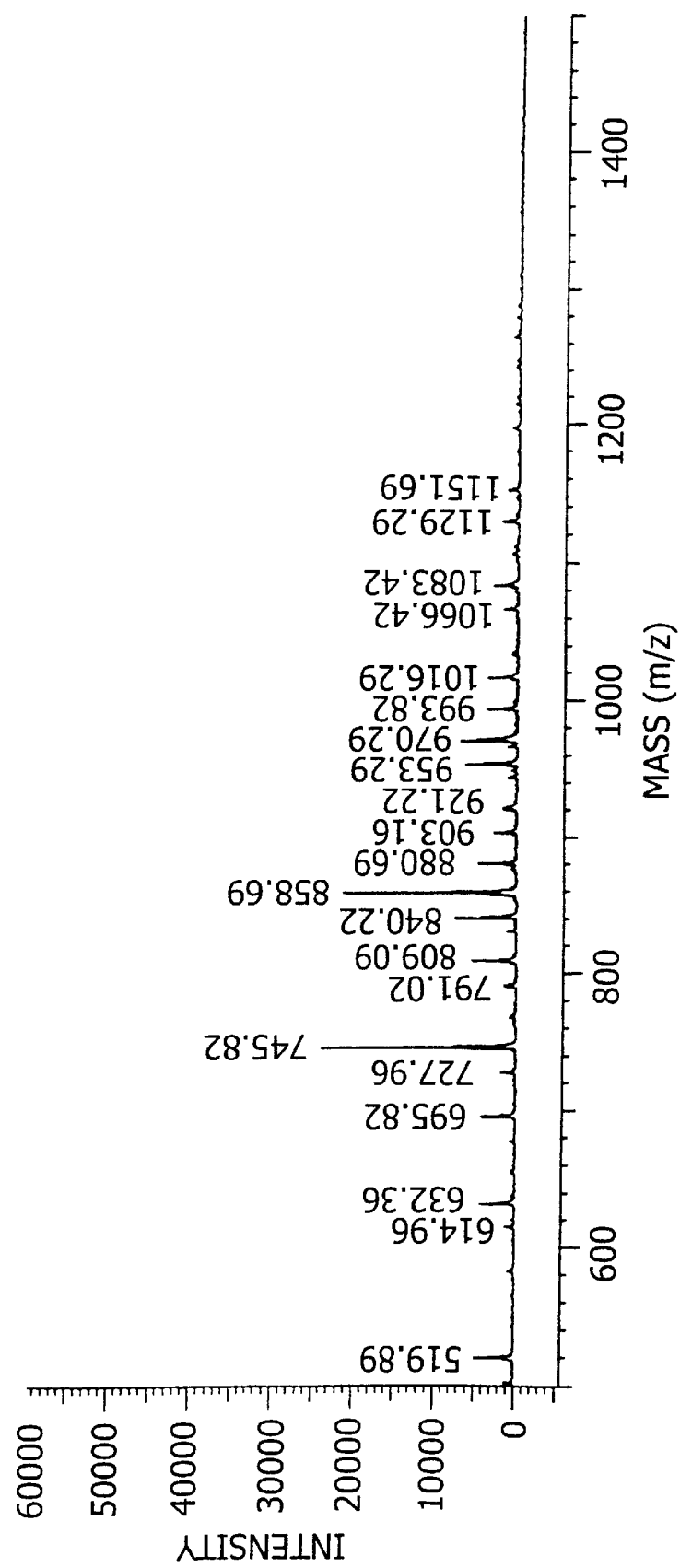
FIG. 33B NEGATIVE ION ESI-MS SPECTRA OF LEUCINE OLIGOMERS

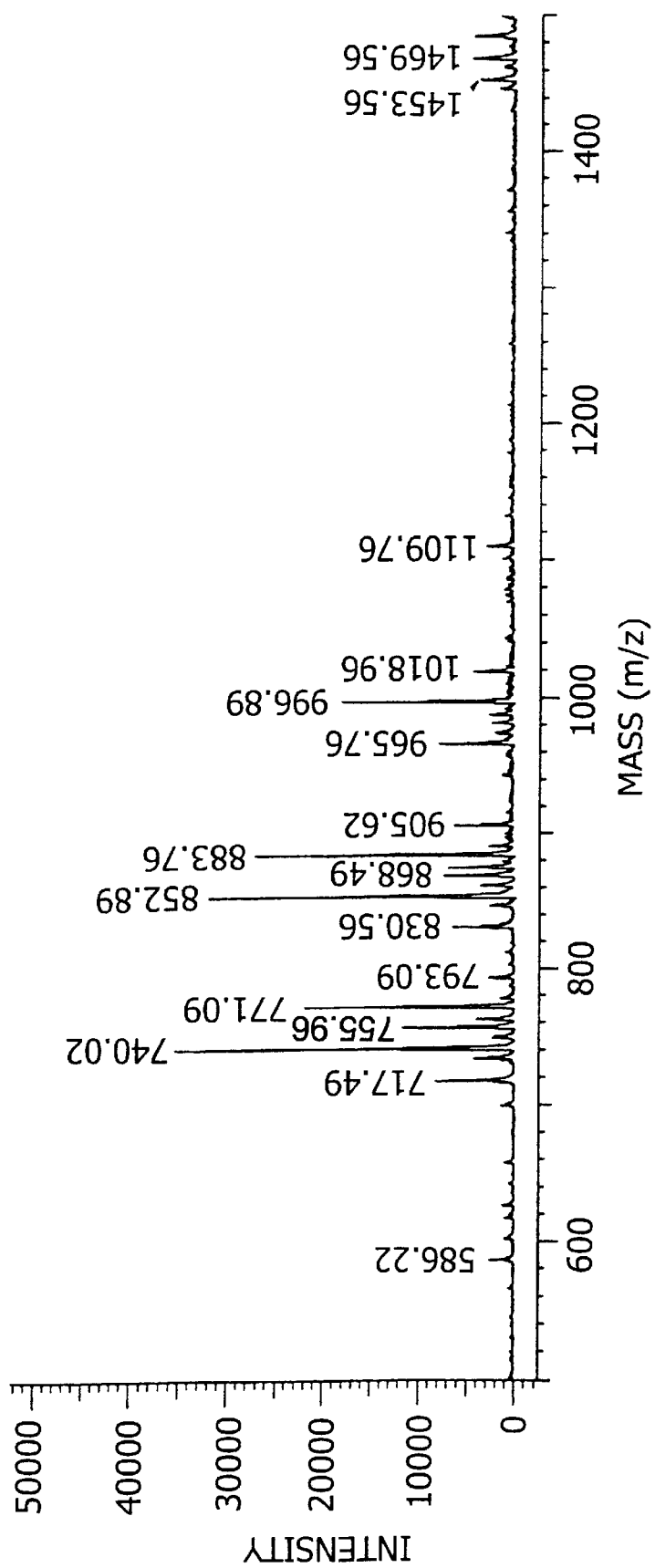
FIG. 34A POSITIVE ION ESI-MS SPECTRA OF HMB LEUCINE CO-OLIGOMERS

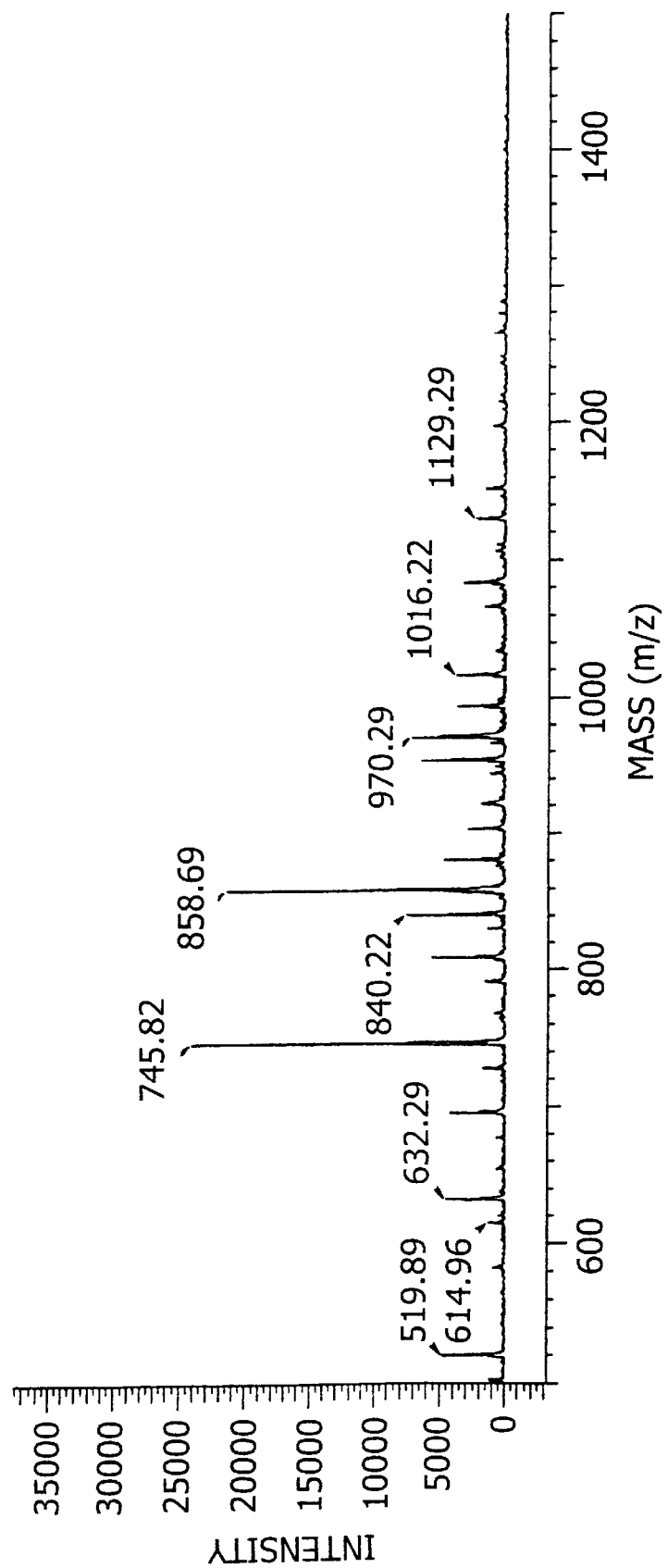
FIG. 34B  NEGATIVE ION ESI-MS SPECTRA OF HMB LEUCINE CO-OLIGOMERS

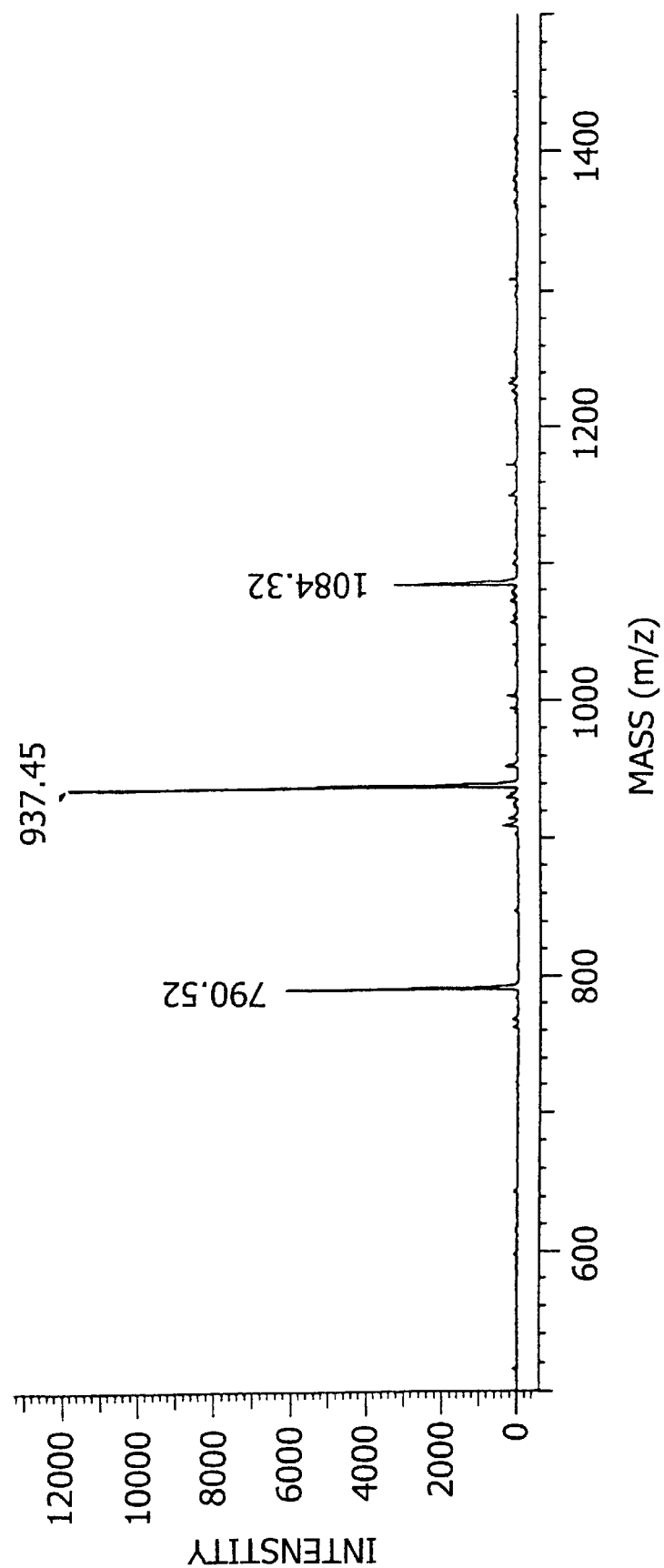
FIG. 35A POSITIVE ION ESI-MS SPECTRA OF HMB-Phe CO-OLIGOMERS

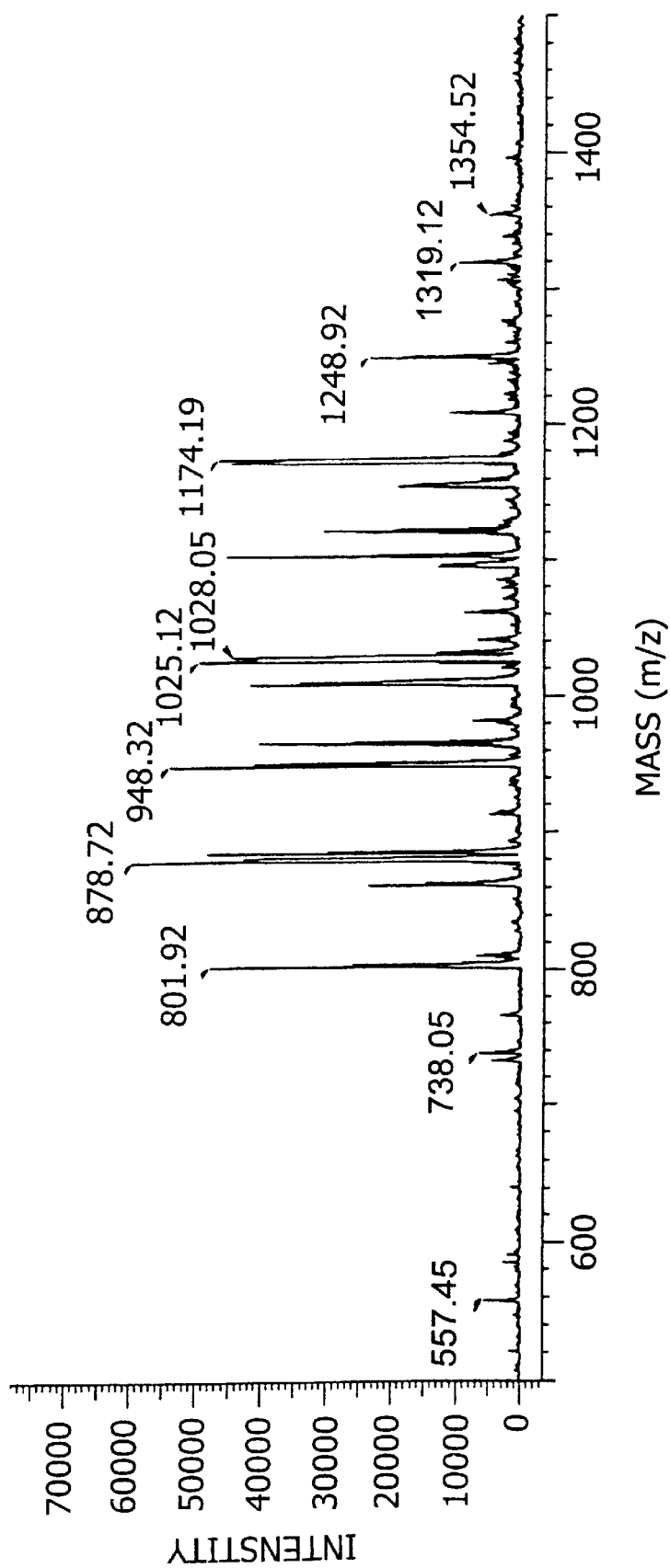
FIG. 35B NEGATIVE ION ESI-MS SPECTRA OF HMB-Phe CO-OLIGOMERS

FIG. 40 EFFECT OF SUBSTRATE CONCENTRATION ON $(Lys)_n$ YIELD
SUBSTRATE CONV vs $(Lys)_n$ YIELD IN THE TWO PHASE SYSTEM

FIG. 41 DISTRIBUTION OF LYSINE OLIGOMERS FORMED IN REACTION MIXTURES WITH VARIED SUBSTRATE CONCENTRATIONS

EFFECT OF SUBSTRATE CONCENTRATION ON THE TWO PHASE SYSTEM

DISTRIBUTION OF LYSINE OLIGOMERS FORMED ATER DIFFERENT INCUBATIONS PERIODS

TWO PHASE SYSTEM: EFFECT OF INCUBATION PERIOD ON OLIGOMERIZATION PROFILE

FIG. 44 EFFECT OF AQUEOUS TO NON-AQUEOUS SOLVENT PHASE RATIO ON OLIGOMERS YIELD
EFFECT OF PHASE RATIO (AQUEOUS TO NON-AQUEOUS)

DISTRIBUTION OF (Lys) OLIGOMERS FORMED IN REACTION MIXTURES WITH VARIED AQUEOUS TO NON-AQUEOUS SOLVENT RATIOS.

EFFECT OF VOLUMETRIC PHASE RATIO IN BIPHASIC SYSTEM

EFFECT OF ADDITIVE CONCENTRATION ON THE TOTAL LYSINE OLIGOMERS YIELD

EFFECT OF ADDITIVE COMPOSITION

EFFECT OF INCUBATION PERIOD ON THE TOTAL LYSINE OLIGOMERS YIELD

TIME-SERIES YIELD OF LYSINE OLIGOMERIZATION IN TRI-PHASIC SYSTEM

DISTRIBUTION OF (Lys) OLIGOMERS FORMED AFTER 24 HOUR INCUBATION PERIOD

THREE PHASE SYSTEM: OLIGOMERIZATION PROFILE

SEQUENCE LISTING

```
<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 1

Met Met Met Met
1

<210> SEQ ID NO 2
<211> LENGTH: 5
<212> TYPE: PRT
<213> ORGANISM: Artificial Sequence
<220> FEATURE:
<223> OTHER INFORMATION: Artificially synthesized sequence for use in
```

```
        feed supplement

<400> SEQUENCE: 2

Met Met Met Met Met
1               5

<210> SEQ ID NO 3
<211> LENGTH: 6
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 3

Met Met Met Met Met Met
1               5

<210> SEQ ID NO 4
<211> LENGTH: 7
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 4

Met Met Met Met Met Met Met
1               5

<210> SEQ ID NO 5
<211> LENGTH: 8
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 5

Met Met Met Met Met Met Met Met
1               5

<210> SEQ ID NO 6
<211> LENGTH: 9
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 6

Met Met Met Met Met Met Met Met Met
1               5

<210> SEQ ID NO 7
<211> LENGTH: 6
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 7

Xaa Met Met Met Met Met
```

```
<210> SEQ ID NO 8
<211> LENGTH: 7
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 8

Xaa Met Met Met Met Met Met
1               5

<210> SEQ ID NO 9
<211> LENGTH: 8
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 9

Xaa Met Met Met Met Met Met Met
1               5

<210> SEQ ID NO 10
<211> LENGTH: 4
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 10

Xaa Met Met Met
1

<210> SEQ ID NO 11
<211> LENGTH: 5
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 11

Xaa Met Met Met Met
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: Artificially sythesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 12

Xaa Met Met Met Met Met Met Met Met
1               5

<210> SEQ ID NO 13
<211> LENGTH: 10
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 13

Met Met Met Met Met Met Met Met Met Met
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Artificially synthesized sequence for use in
      feed supplement
<220> FEATURE:
<221> NAME/KEY: MISC_FEATURE
<222> LOCATION: (1)..(1)
<223> OTHER INFORMATION: Xaa=2-hydroxy-4-(methylthio)butyric acid

<400> SEQUENCE: 14

Xaa Met Met Met Met Met Met Met Met Met
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 15

Lys Lys Lys Lys Lys Lys Lys Lys Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 16

Lys Lys Lys Lys Lys Lys
1               5

<210> SEQ ID NO 17
<211> LENGTH: 4
<212> TYPE: PRT
<213> ORGANISM: Artificial Sequence
<220> FEATURE:
```

```
<223> OTHER INFORMATION: Artificially synthesized sequence for use in
      feed supplement

<400> SEQUENCE: 17

Lys Lys Lys Lys
1

<210> SEQ ID NO 18
<211> LENGTH: 5
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 18

Lys Lys Lys Lys Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 19

Lys Lys Lys Lys Lys Lys Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Artificially synthesized sequence for use in
      feed supplement

<400> SEQUENCE: 20

Lys Lys Lys Lys Lys Lys Lys Lys
1               5
```

OLIGOMERS AND OLIGOMERIC SEGMENTS OF ALPHA-HYDROXY CARBOXYLIC ACIDS AND ALPHA-AMINO ACIDS

CROSS-REFERENCE TO RELATED APPLICATION

This application claims priority from U.S. provisional application Ser. No. 60/162,725, filed Oct. 29, 1999, the entire disclosure of which is incorporated herein by reference.

BACKGROUND OF THE INVENTION

The present invention relates to a process for the preparation of oligomers of α-hydroxy carboxylic acids and α-amino acids and to compositions containing such oligomers.

In an effort to improve nutrition, the diets of ruminant animals have been supplemented with proteins and naturally occurring α-amino acids. Unfortunately, these proteins and α-amino acids can be subjected to extensive degradation in the rumen by ruminal microorganisms, thereby rendering the protein or amino acid unavailable to the animal for absorption. This is not a very efficient utilization of the feed, which is especially problematic in animals having increased nutritional requirements such as lactating dairy cows and fast growing animals such as beef cattle.

One approach to solving this problem has been to modify or protect the dietary protein or amino acid by a variety of chemical and physical methods so that it escapes degradation in the rumen. For example, heating soybean meal has shown some promise in producing protected proteins however the results were highly variable. Underheating the protein resulted in no protection while overheating the protein resulted in the degradation of important essential amino acids. See, for example, Plegge, S. D., Berger, L. L. and Fahey Jr. G. C. 1982. Effect of Roasting on Utilization of Soybean Meal by Ruminants. *J. Anim. Sci.* 55:395 and Faldet, M. A., Son, Y. S. and Satter, L. D. 1992. Chemical, in vitro and in vivo evaluation of soybean heat-treated by various processing methods. *J. Dairy Sci.* 75:789. Similarly, physical coating of proteins with materials such as fats and calcium soaps of fats has been with mixed success.

Therefore, there is a need to somehow protect the protein from degradation in the rumen in order to make it available to the animal in the intestine where it can be properly absorbed. This would allow the animal to get increased nutritional benefit from the feed. Increasing the nutritional benefit of the feed can reduce the amount of feed required by the animals.

The role played by short chain peptides and their derivatives in the areas of nutrition science, flavor chemistry and pharmacology has primed the advances in peptide chemistry. The inherent advantages of enzymatic peptide synthesis has led to it's evolution as an alternative to chemical coupling methods (Fruton, J. S., 1992, Adv. Enzymology, 53, 239–306). The thiol-protease papain is reported to be the most efficient catalyst for aqueous phase synthesis of homooligomers of hydrophobic amino acids like leucine, methionine, phenylalanine and tyrosine (A. Ferjancic, A. Puigserver and H.Gaertner, *Biotech. Lett,* 13(3) (1991) 161–166). The equilibria of such reactions is tilted in favor of synthesis by the precipitation of hydrophobic oligomers. However, the difficulty involved in the analysis of higher order, water insoluble oligomers, presents an unique challenge to biochromatography.

SUMMARY OF THE INVENTION

Among the objects of the present invention, therefore, is the provision of an oligomer which is protected from degradation in the rumen of a ruminant, the provision of such an oligomer which provides nutritional or pharmacological benefit to the animal, and the provision of a process for the preparation of such oligomers.

Briefly, therefore, the present invention is directed to a composition comprising the oligomeric segment —CA—(AA)$_n$—wherein CA is the residue of an α-hydroxy carboxylic acid, each AA is the residue of an α-amino acid independently selected from the group consisting of α-amino acids, n is at least 1 and CA is bonded to (AA)$_n$ by an amide linkage.

The present invention is further directed to a process for the preparation of an oligomer. The process comprises preparing a mixture containing (i) an enzyme, (ii) an α-hydroxy carboxylic acid and (iii) an α-amino acid or a peptide oligomer. The α-hydroxy carboxylic acid and the α-amino acid each are present in the mixture as a free acid, acid halide, amide, ester or anhydride independently of the other. The process further comprises forming an amide linkage between the residue of the α-hydroxy carboxylic acid and the residue of the α-amino acid or the peptide oligomer.

Other objects and features of this invention will be in part apparent and in part pointed out hereinafter.

BRIEF DESCRIPTION OF THE DRAWINGS

FIG. 14B is a positive ion total ion chromatogram of persulfonated methionine oligomers.

FIG. 15A is a chromatogram of persulfonated HMBA-methionine co-oligomers using a UV absorption detector.

FIG. 15B is a positive ion total ion chromatogram of persulfonated HMBA-methionine co-oligomers.

FIG. 20B is a positive ion ESI spectra of $(Met)_8$ sulfone (SEQ ID NO: 5) peak eluting at 14.26 minutes.

FIG. 20C is a positive ion ESI spectra of $(Met)_9$ sulfone (SEQ ID NO: 6) peak eluting at 15.60 minutes.

FIG. 22A is a chromatogram of persulfonated HMBA-methionine co-oligomers using a UV absorption detector.

FIG. 22B is a total ion chromatogram ESI-negative ion of persulfonated HMBA-methionine co-oligomers.

FIG. 23 is a negative ion ESI spectra of HMBA-$(Met)_5$ sulfone (SEQ ID NO: 7) peak eluting at 11.57 minutes.

FIG. 24 is a negative ion ESI spectra of HMBA-$(Met)_6$ sulfone (SEQ ID NO: 8) peak eluting at 13.86 minutes.

FIG. 28B is a negative ion ESI-MS spectra HMBA-methionine co-oligomers synthesized with HMBA methyl ester and methionine ethyl ester.

FIG. 29 is a parent ion SSI-MS spectra HMBA-methionine co-oligomers synthesized with HMBA methyl ester and methionine ethyl ester.

FIG. 30 is a daughter ion spectrum of $(Met)_6$-ethyl ester (SEQ ID NO: 3).

FIG. 31A is a positive ion ESI-MS spectra of tyrosine (Tyr)n oligomers wherein n is the number of tyrosine residues in the oligomers.

FIG. 32A is a positive ion spectra of MHBA-tyrosine co-oligomers.

FIG. 32B is a negative ion spectra of MHBA-tyrosine co-oligomers.

FIG. 33A is a positive ion ESI-MS spectra of leucine oligomers.

FIG. 33B is a negative ion ESI-MS spectra of leucine oligomers.

FIG. 34A is a positive ion ESI-MS spectra of HMBA-leucine co-oligomers.

FIG. 34B is a negative ion ESI-MS spectra of HMBA-leucine co-oligomers.

FIG. 35A is a positive ion ESI-MS spectra of HMBA-phenylanaline co-oligomers.

FIG. 35B is a negative ion ESI-MS spectra of HMBA-phenylanaline co-oligomers.

DETAILED DESCRIPTION OF THE PREFERRED EMBODIMENTS

Figure 1:
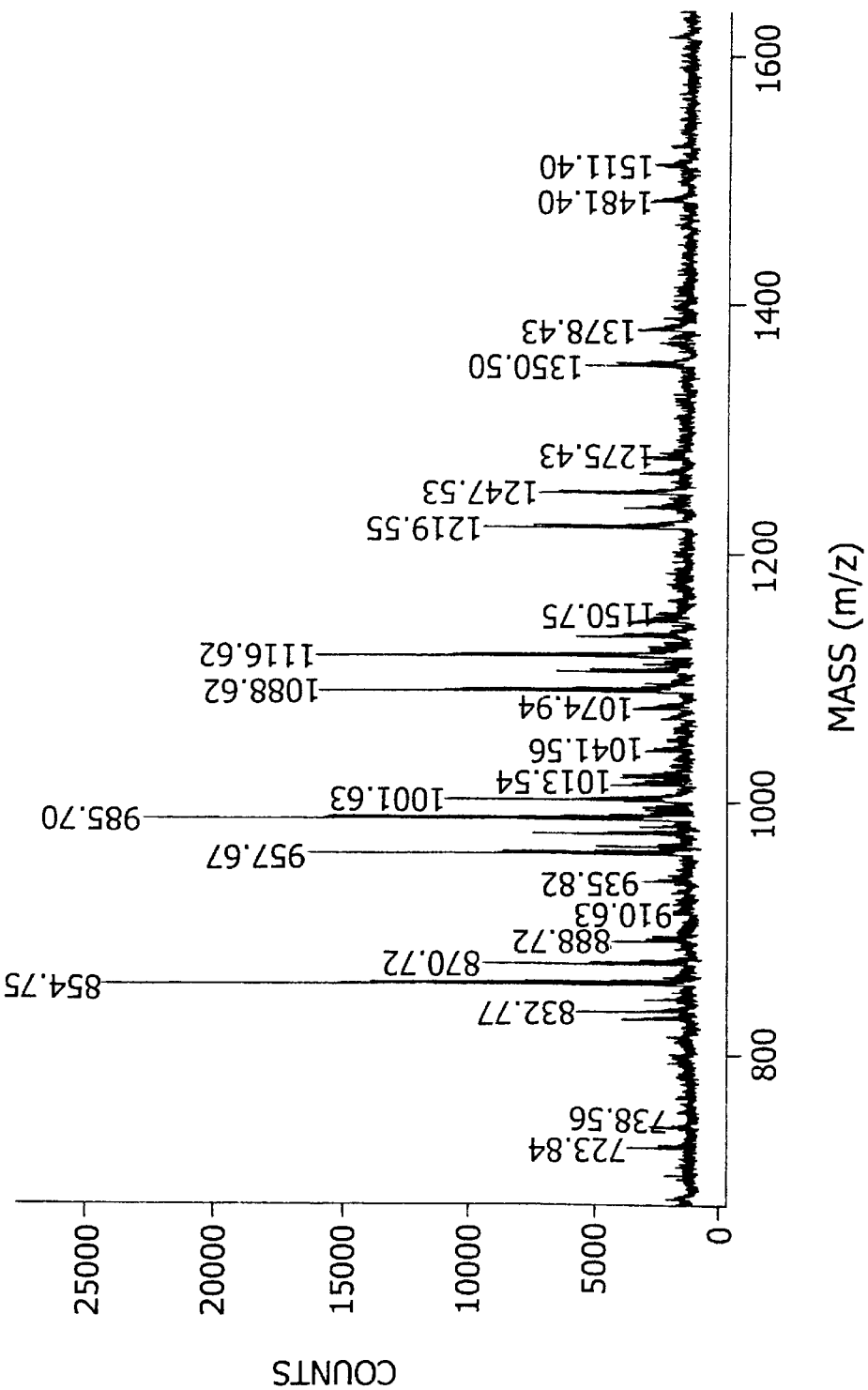
FIG. 1 is a MALDI-TOF graph of methionine oligomers from a papain catalyzed synthesis.

In accordance with the present invention, it has surprisingly been discovered that oligomers of α-hydroxy carboxylic acids and α-amino acids may be prepared in an enzymatically catalyzed reaction. In general, the oligomer corresponds to the formula CA—$(AA)_n$ wherein CA is the residue of an α-hydroxy carboxylic acid, each AA is the residue of an α-amino acid independently selected from the group consisting of α-amino acids, n is at least 1 and CA is bonded to (AA)$_n$ by an amide linkage. Typically, n will be less than 20. In some embodiments, n will range from about 1 to about 10, more typically about 2 to about 8 and, in some embodiments, about 3 to about 5.

Advantageously, the composition of the oligomer may be tailored for each application. For example, if n is greater than 1, the oligomer may contain only one amino acid residue (e.g., only methionine or lysine residues, but not both) or the oligomer may contain two or more different amino acid residues (e.g., methionine and lysine residues). Thus, the oligomer may be designed to meet the essential amino acid requirements of the animal (e.g. 3:1, lysine:methionine residues).

The oligomer may be obtained (and used) as a dimer, trimer, tetramer, pentamer, hexamer, septamer, octamer, nonamer, decamer, etc. in which a residue of the α-hydroxy carboxylic acid is linked to a residue of an α-amino acid via an amide linkage. Alternatively, an oligomeric segment may be obtained which is chemically or enzymatically linked to another moiety, for example, through the α-hydroxy group of the α-hydroxy carboxylic acid residue or the carboxy terminus of the α-amino acid residue.

In a preferred embodiment, the oligomer or oligomeric segment corresponds to the structure

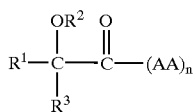

wherein

R$^1$ is hydrogen, hydrocarbyl or substituted hydrocarbyl,

R$^2$ is hydrogen, hydrocarbyl, substituted hydrocarbyl, or a hydroxy protecting group, R$^3$ is hydrogen, hydrocarbyl or substituted hydrocarbyl, each AA is the residue of an α-amino acid selected from the group consisting of α-amino acids independently of any other α-amino acid residue, and n is at least 1.

α-Hydroxy Carboxylic Acid Residue

In general, the oligomer or oligomeric segments of the present invention may comprise the residue of any α-hydroxy carboxylic acid. Preferred α-hydroxy acids correspond to the general structure R$^1$R$^3$C(OR$^2$)COOH wherein R$^1$ is hydrogen, hydrocarbyl or substituted hydrocarbyl; R$^2$ is hydrogen, hydroxy protecting group, hydrocarbyl, or substituted hydrocarbyl; and R$^3$ is hydrogen, hydrocarbyl or substituted hydrocarbyl, preferably hydrogen. For example, the α-hydroxy carboxylic residue may be the residue of any of the following naturally occurring α-hydroxy carboxylic acids (with R$^1$ for such acid being given in brackets): lactic acid [—CH$_3$], mandelic acid [—C$_6$H$_5$], malic acid [—CH$_2$COOH], and tartaric acid [—CH(OH)COOH]. In addition, the α-hydroxy carboxylic acid residue may be the residue of an α-hydroxy acid analog of a naturally occurring α-amino acid, more preferably the residue of the α-hydroxy analog of an essential α-amino acid, and still more preferably the residue of the α-hydroxy analog of methionine, i.e., 2-hydroxy-4-(methylthio)butyric acid.

In general, the α-hydroxy carboxylic acid residue may be the residue of an α-hydroxy carboxylic acid having the D configuration, the L configuration, or from a racemic or other mixture of the D and L isomers. In some embodiments, however, it is generally preferred that the α-hydroxy carboxylic acid residue be the residue of an α-hydroxy carboxylic acid having the L configuration.

α-Amino Acid Residue(s)

In general, the oligomer or oligomeric segments of the present invention may comprise the residue of any α-amino acid. Preferred α-amino acids correspond to the general structure R$^a$R$^b$C(NH$_2$)COOH wherein R$^a$ is hydrogen, hydrocarbyl, substituted hydrocarbyl or heterocyclo; and R$^b$ is hydrogen. For example, the α-hydroxy amino residue(s) may be the residue(s) of any of the naturally occurring α-amino acids, e.g., asparagine, glycine, alanine, valine, leucine, isoleucine, phenylalanine, proline, serine, threonine, cysteine, methionine, tryptophan, tyrosine, glutamine, aspartic acid, glutamic acid, lysine, arginine, and histidine. Preferably, the α-amino acid residue(s) include the residue(s) of one or more essential α-amino acids, i.e., isoleucine, phenylalanine, leucine, lysine, methionine, threonine, tryptophan, histidine and valine. Still more preferably, the α-amino acid residue(s) include the residue(s) of methionine and/or lysine.

In general, the α-amino acid residue may be the residue of an α-amino acid having the D configuration, the L configuration, or from a racemic or other mixture of the D and L isomers. In some embodiments, however, it is generally preferred that the α-amino acid residue be the residue of an α-amino acid having the L configuration.

Enzymatic Oligomerization

The oligomers or oligomeric segments of the present invention are enzymatically synthesized in a mixture. The mixture comprises at least one α-hydroxy carboxylic acid or a derivative thereof, at least one α-amino acid or a derivative thereof, and an enzyme.

The α-hydroxy carboxylic acid may be present in the mixture as a free acid or as a carboxylic acid derivative, e.g., the corresponding ester, acid halide, amide, anhydride, or ketene. Preferably, the α-hydroxy carboxylic acid and its derivatives have the formula R$^1$R$^3$C(OR$^2$)COY or R$^1$C(OR$^2$)=C=O wherein R$^1$, R$^2$ and R$^3$ are as previously defined and Y is hydroxy (for the free acid), halogen (for acid halide derivatives), hydrocarbyloxy (for ester derivatives), amino (for amide derivatives), and hydrocarbylcarboxy (for anhydride derivatives). In some embodiments, the α-hydroxy carboxylic acid is preferably present in the mixture in the form of an ester, i.e., where Y is —OR$^5$ and R$^5$ is hydrocarbyl, more preferably alkyl, alkene, or aryl, still more preferably lower alkyl. In other embodiments, the α-hydroxy carboxylic acid is preferably present in the mixture in the form of an amide, i.e., where Y is —NR$^6$R$^7$ and R$^6$ and R$^7$ are independently hydrogen or hydrocarbyl, more preferably lower alkyl, still more preferably hydrogen.

The mixture need not contain a single α-hydroxy carboxylic acid species. Thus, for example, the mixture may contain the hydroxy analog of methionine (in one or more of its free acid, acid halide, amide, anhydride or ketene forms) and, in addition, one or more other α-hydroxy carboxylic acids such as lactic acid, mandelic acid, malic acid, or tartaric acid (in one or more of their respective free acid, acid halide, amide, anhydride or ketene forms).

Similarly, the α-amino acids may be present in the mixture as a free acid or as a carboxylic acid derivative, e.g., the corresponding ester, acid halide, amide, anhydride, or ketene. In general, the α-amino acid and its derivatives have the formula R$^a$R$^b$C(NH$_2$)COY or R$^a$C(OR$^2$)=C=O wherein $R^a$, $R^2$ and $R^b$ are as previously defined and Y is hydroxy (for the free acid), halogen (for acid halide derivatives), hydrocarbyloxy (for ester derivatives), amino (for amide derivatives), and hydrocarbylcarboxy (for anhydride derivatives). In some embodiments, the α-amino acid is preferably present in the mixture in the form of an ester, i.e., where Y is —$OR^5$ and $R^5$ is hydrocarbyl, more preferably alkyl or aryl, still more preferably lower alkyl. In other embodiments, the α-amino acid is preferably present in the mixture in the form of an amide, i.e., where Y is —$NR^6R^7$ and $R^6$ and $R^7$ are independently hydrogen or hydrocarbyl, more preferably lower alkyl, still more preferably hydrogen.

The mixture need not contain a single α-amino acid species. Thus, for example, the mixture may contain one α-amino acid (in one or more of its free acid, acid halide, amide, anhydride or ketene forms) and, in addition, one or more other α-amino acids (in one or more of their respective free acid, acid halide, amide, anhydride or ketene forms). By way of further example, the mixture may contain methionine (in one or more of its free acid, acid halide, amide, anhydride or ketene forms) and, in addition, one or more other nutritionally important α-amino acid(s) such as lysine, tryptophan and/or phenylalanine (in one or more of their respective free acid, acid halide, amide, anhydride or ketene forms).

In addition to, or instead of α-amino acid monomers, the mixture may contain oligomers (e.g., dimers, trimers, tetramers, pentamer, hexamer, septamer, octamer, nonamer, decamer, etc.) of one or more α-amino acids. For example, the mixture may contain a homooligomer formed from methionine, lysine or other α-amino acid or a heterooligomer of an α-amino acid (e.g., methionine) and at least one other nutritionally important α-amino acid such as lysine, tryptophan and/or phenylalanine. When present in the mixture, such oligomers will be enzymatically linked through their amino terminus to the carboxy terminus of the α-hydroxy carboxylic acid, thereby forming an amide linkage between the two.

In general, the mixture contains an enzyme which catalyzes the formation of peptide bonds. Exemplary enzymes include serine proteinases (e.g., Trypsin, α-Chymotrypsin, Elastase, Carboxypeptidase, and Subtilisin), thiol proteinases (e.g., Papain, Ficin, Bromelain, Streptococcal proteinase, Cathepsins, Calpains, Clostripain, and Actinidin), metalloproteinases (e.g., Thermolysin), acid proteinases (e.g., Pepsin, Penicillopepsin, Chymosin, Cathepsin, and Renin), liver esterase (e.g., pig liver esterase), alkaline protease, carbonic anhydrase, nonribosomal peptide synthetase, thrombin, cardosins A or B, or pronase.

The enzyme may be dissolved in the mixture or, alternatively, it may be adsorbed or otherwise immobilized onto a variety of substrates. For example, the enzyme may be immobilized onto controlled pore glass, agarose, sepharose, nylon, or polyethylene glycol. Enzymes may also be adsorbed, for example, onto activated charcoal, ion exchange resins, silica, polyacrylamide, collagen, starch, bentonite, ultramembrane filters, cellulose, alumina, titania, and polyvinylchloride. In addition, enzymes may be retained by entrapment, microencapsulation, liposome formation, hollow fiber, inorganic bridge formation, and aggregation.

In one embodiment of the present invention, the enzymatic reaction is carried out in a single phase, aqueous solution under conditions typically employed in enzyme catalyzed reactions for the preparation of oligomers of α-amino acids. Such systems are typically used in enzymatic biochemical reaction. See, e.g., Lehninger, Nelson, and Cox, Principles of Biochemistry, 1993, Worth Publisher, NY, N.Y.

In a second embodiment of the present invention, the enzymatic reaction is carried out in a two-phase system comprising an aqueous phase and an organic phase. In general, the organic phase comprises an organic solvent selected from the group consisting of alkanes, alkenes, aryls and suitable derivatives thereof. See, e.g., Olmsted and Williams, Chemistry the Molecular Science, 1994, Mosby Publisher, St. Louis, Mo.

In a third embodiment of the present invention, the enzymatic reaction is carried out in a reverse micelle system. Such a system comprises a continuous organic phase, a dispersed aqueous phase, and a surfactant to obtain and stabilize micelle phase. In general, the organic phase comprises an organic solvent selected from the group consisting of alkyl, aryl, and suitable derivatives thereof, and the surfactant is selected from the group consisting of ionic or non-ionic surfactants. Such reverse micelle systems are typically used for biotechnological reactions. See, e.g., Vicente, Aires-Barros, and Empis, J. Chem. Tech. Biotechnol. 1994, 60, 291.

In a fourth embodiment of the present invention, the enzymatic reaction is carried out in a three-phase system comprising an aqueous phase, a first organic phase and a second organic phase with the two organic phases being immiscible. In general, the first organic phase comprises an organic solvent selected from the group consisting of hydrocarbon solvents and the second organic phase comprises an organic solvent selected from the group consisting of halogenated hydrocarbon, perhalogenated hydrocarbon, and halogenated hydrocarbyl solvents. Such three phase systems are routinely used for chemical and biochemical reactions.

In general, the reaction may be carried out over a relatively wide range of temperatures, e.g., about 40° C. to about 50° C., typically about 35 to about 40° C. The pH of the aqueous phase is typically about 5.5 to about 9. Depending upon whether the reaction is carried out in a single phase, aqueous solution or in a multi-phase system, the ratio of the water phase to the organic phase may range from 100:0 to 0.1:99.9 parts by weight, respectively. Reaction time varying from minutes to hours for desired yield. And with/without physical agitation for reaction system.

Separation

Specific oligomers can be separated from the reaction mixtures through precipitation, filtration, selective extraction, column chromatography, lyophilization, and evaporation techniques. Often, the oligomeric products are precipitates which may be easily filtered or centrifuged away from the reacting mixture containing the free hydroxy acids and α-amino acids. Soluble oligomer products can be separated from the free amino and hydroxy acids using membrane filtration. Alternatively, free amino acids and α-hydroxy acids may be removed from the mixture using ion exchange or other applicable chromatographic technique. The selection of separation procedure is dependent on the desired oligomers.

Use

Depending upon the desired application, the compositions of the present invention may be fed or otherwise administered orally, or sprayed into the eye, ear or nasal cavity of an animal, preferably a ruminant. Alternatively, the composition may be injected.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy; nitro, amino, amido, nitro, cyano, and thiol.

The alkyl groups described herein are preferably lower alkyl containing from one to six carbon atoms in the principal chain and up to 20 carbon atoms. They may be straight or branched chain and include methyl, ethyl, propyl, isopropyl, butyl, hexyl and the like.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic hydrocarbon groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include furyl, thienyl, pyridyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, and thiol.

The acyl moieties described herein contain hydrocarbyl, substituted hydrocarbyl or heterocyclo moieties.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include acetyl (Ac), benzyl (PhCH$_2$-), 1-ethoxyethyl (EE), methoxymethyl (MOM), (methoxyethoxy)methyl (MEM), (p-methoxyphenyl) methoxymethyl (MPM), tert-butyldimethylsilyl (TBS), tert-butyldiphenylsilyl (TBPS), tert-butoxycarbonyl (Boc), tetrahydropyranyl (THP), triphenylmethyl (Trityl, Tr), 2-methoxy-2-methylpropyl, benzyloxycarbonyl (Cbz), trichloroacetyl (OCCCl$_3$), benzyloxymethyl (BOM), tert-butyl (t-Bu), triethylsilyl (TES), trimethylsilyl (TMS), and triisopropylsilyl (TIPS).

The abbreviation "MHBA" shall mean the 2-hydroxy analog of methionine, i.e., 2-hydroxy-4-(methylthio)butyric acid.

The following examples illustrate the invention. In general, the enzymatic synthesis of co-oligomers of MHBA and methionine and their characterization through reverse phase HPLC and MALDI-TOF has been reported in the Examples herein. The problem of analysis of higher order oligomers was addressed by the oxidation of the methionine and the MHBA to their relatively hydrophilic sulfones with performic acid.

EXAMPLE 1

Procedure for the Synthesis of Methionine and MHBA-Methionine Oligomers

Papain catalyzed oligomerization of methionine analogues has been optimized under various conditions by S. Arai, M. Yamashita, and M Fujimaki, Agric. Biol. Chem., 43(5), 1069–1074 (1979). The same was applied for the co-oligomerization of MHBA and methionine. The reaction mixture consisted 10 mL nanopure filtered water containing 1.4 M amino acid ethyl esters (0.7 M each in the case of MHBA ethyl ester and methionine ethyl ester) along with 0.1 M L-cysteine, 10 mM EDTA, 1 M sodium citrate and 1% (w/w of the monomer) papain at pH 5.5 and a temperature of 37° C. Aliquots were removed at regular intervals to monitor the degree of oligomerization and the disappearance of the substrate. The mixture was allowed to incubate for a periods ranging between 10 minutes to 24 hours.

Papain catalyzed oligomerization of methionine analogues has also been optimized under various conditions by R. Jost, E. Brambilla and J. C. Monti, Helv. Chim. Acta, 63 (1980) 375–384 (1980). A synthesis was similarly carried out with a reaction mixture consisting of 10 g of L-methionine ethyl ester (5 g each in the case of co-oligomerization of L-methionine ethyl ester and HMB ethyl ester) dissolved in 50 ml of nanopure water containing 0.1 mole sodium bicarbonate buffer and 4 mmole L-cysteine set to a pH of 9. The solution was made up to 100 ml and then incubated for 24 hrs at 37° C. after adding 2 g papain. The reactions in all cases were terminated by thermal denaturation of the enzyme by heating the mixture at 80° C. for 10 minutes.

Analysis of Oligomers

An aliquot was removed and heated to 80° C. for 10 minutes to denature the enzyme. The mixture was centrifuged and the supernatant was analyzed on a RPLC to monitor the synthesis of methionine oligomers of order 3 or less along with the disappearance of the substrate. Attempts at resolving the higher order oligomers with RPLC and gel permeation liquid chromatography (GPC) were unsatisfactory especially for oligomers with 4–10 monomer residues. The experiments revealed underivatized oligomers could not be eluted from C-18 or C-8 columns with the common mobile phases due to poor solubility of oligomers in these mobile phases. The oligomers were soluble in dimethyl sulfoxide (DMSO) and tetrahydrofliran (THF) a common mobile phase in GPC for separations. However, oligomers with less than ten residues could not be resolved from the solvent in GPC separations. A persulfonation procedure was therefore adopted. Persulfonation of oligomers enhanced the polarity of the oligomers to a point that these could be separated on a C-18 column with a moderately polar mobile phase (M. Spindler, R. Stadler and H. J. Tanner, *J. Agri. Food Chem.*, 32(6) (1984)1366–1371).

Persulfonation of Oligomers

The mixture was washed thoroughly till no traces of the monomers and the salts were left behind. The mixture was then freeze dried and a part of it was subjected to persulfonation with a method which was adapted from a procedure outlined by Spidler and coworkers. The procedure involved oxidation of all sulfide moieties in the oligomers with performic acid. The performic acid for the purpose was prepared by oxidation of formic acid (HCOOH) with hydrogen peroxide ($H_2O_2$). A 0.5 mL solution of 30% $H_2O_2$ was mixed with 4.5 mL of 88% HCOOH and 25 mg phenol. The mixture was allowed to stand for 30 minutes at room temperature. After 30 minutes, the mixture was cooled to 0° C. for 15 minutes in an ice bath and used for the oxidizing 10 mg of finely divided oligomers powder in the ice bath. The reactants were stirred for 15 minutes and placed a refrigerator over night. The excess performic acid was reduced with 0.7 mL of 48% hydrobromic acid (HBr). The residual bromine and formic acid were removed with a rotary evaporator at 50–60° C.

Liquid Chromatography

The oligomer sulfone residues in the rotary evaporator round bottom flasks were dissolved in 5 mL of acetonitrile/water mixture (40:60) and filtered through a membrane filter. A 10 $\mu L$ aliquot of the solution was injected into a HPLC. The separation of persulfonated oligomers was achieved with a C-18 column using a phosphate buffer—acetonitrile mobile phase. A linear gradient was used to facilitate separations. In this gradient the mobile phase composition was changed from 100% eluant A (phosphate buffer, pH 6.5) to 60% A and 40% B (20% Acetonitrile) in 20 minutes. The mobile phase flow rate was maintained at 1 mL $min^{-1}$. The separated oligomers were detected with a UV/VIS diode array detector.

TOF Experiments

Aliquots of purified oligomers dissolved in DMSO were introduced into the mass spectrometer along with a thioglycerol matrix. The mass spectrometer operating parameters were:

| Accelerating Potential | +20KV |
| --- | --- |
| Grid Voltage | 80% |
| Low Mass Gate | 191.0 |
| Flight tube pressure | 3.3 $e^{-7}$ torr |

TOF-MALDI Analysis

The TOF-MALDI spectra of methionine (Met) oligomers are shown in FIG. 1. The spectra contain distinct ions which are separated by mass 131. This mass (131) represents the repeating Met moiety ($C_5H_9NOS$), since the masses of the N and C terminal methionine residues are 132 and 148 respectively. Therefore, a methionine hexamer $(Met)^6$, ($^N$Met-$(Met)_4$-Met$^C$) +H$^+$should appear at m/z 805 and $(Met)^7$ should appear at m/z 936. However, the m/z values of the dominant ions did not correspond to this series, instead, one set of dominant ions appeared at m/z 826, 957, 1088, 1219, 1350 and 1481. These ions most likely correspond to (($(Met)^n$+Na$^+$), where n is an integer between 6 and 11. The second group of ions appeared at m/z 724, 855, 986, 1117, 1248 and 1379. These ions most likely correspond to the series ($^N$Met-(Met)-Met-O—$C_2H_5$) +Na$^+$. A third set of ions appeared at m/z 739, 870, 1001 and 1134, these ions most likely correspond to $^N$Met-$(Met)_n$-Met-O—$C_2H_5$+K$^+$. A fourth set of unidentified ions seem to be present at regular intervals in the clusters and which might be assigned the mass values, 842, 973, 1104, 1235 and 1366 corresponding to the series $^N$Met-$(Met)_n$-Met$^C$)+K$^+$. In all these cases "n" can vary between 6 to 11.

Figure 2:
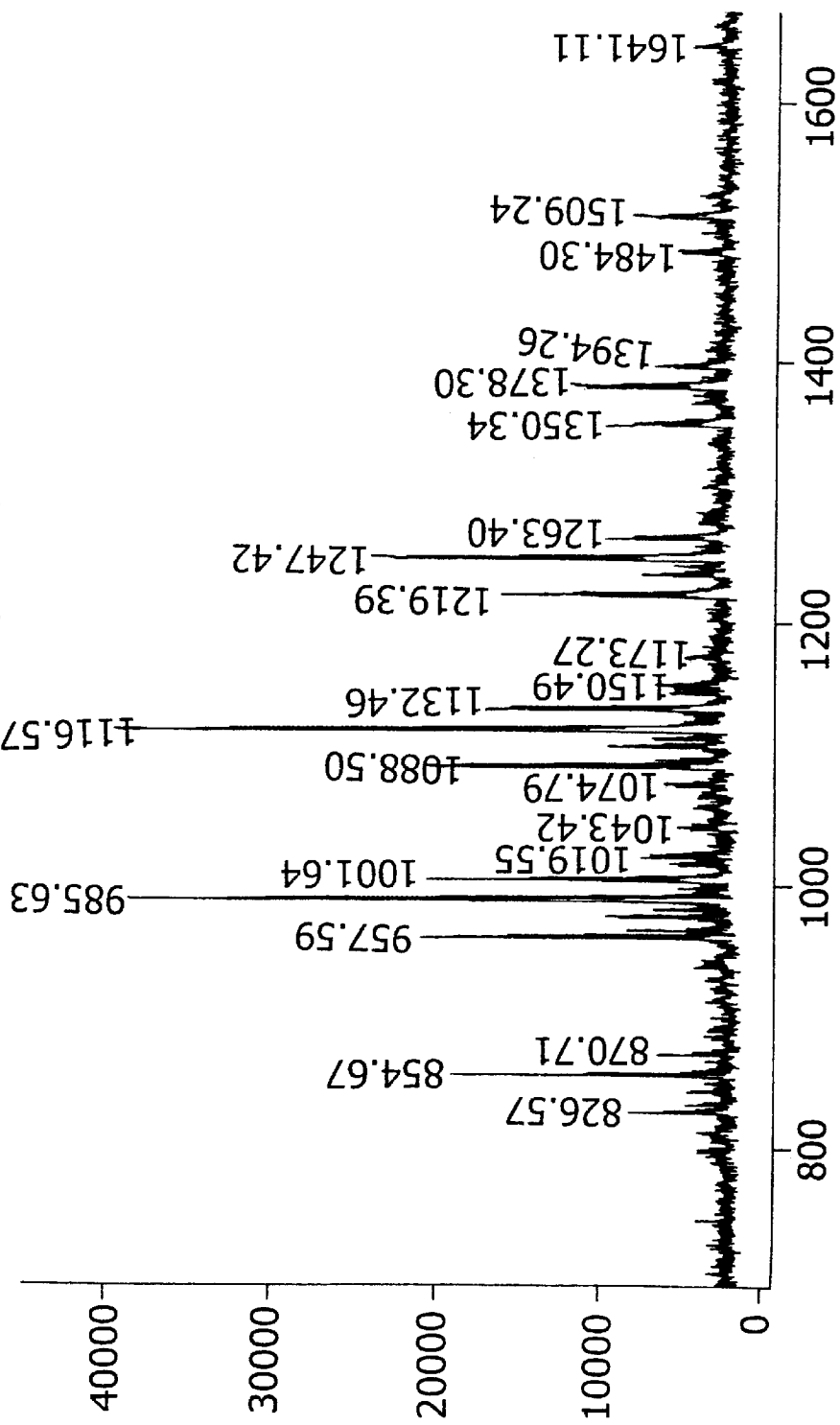
FIG. 2 is a MALDI-TOF graph of MHBA-methionine oligomers from a papain catalyzed synthesis.

The spectra of MHBA-Met co-oligomers is shown in FIG. 2. In this spectra ions corresponding to the series ($^N$Met -$(Met)_n$-Met$^C$) +Na$^+$, ($^N$Met-$(Met)_n$-Met-O—$C_2H_5$)+Na$^+$, $^N$Met-$(Met)_n$-Met$^C$+K$^+$, and $^N$Met-$(Met)_n$-Met-O—$C_2H_5$+K$^+$ were readily observed. However, the ions, which should correspond to (MHBA -$(Met)_n$-Met$^C$)+H$^+$or +Na$^+$m/z 806, 937 and 1118; 827, 958 and 1089 were not observed in the spectra. The apparent absence of these ions, however, does not necessarily mean the absence of MHBA-$(Met)^n$ co-oligomers in the in the product mixture. The absence of the ions can be attributed to two factors. The first relates to the low resolving power of the TOF-MS, which would prevent the resolution of the H$^+$MHBA-$(Met)^n$-Met$^C$ ions at m/z 806, 937, 1118 from the H$^{+N}$Met-$(Met)^n$-Met$^C$ ions at m/z 805, 936, 1117. The second, a more probable, cause is the low intensity of the H$^+$MHBA-$(Met)^n$-Met$^C$ ion due to the absence of a good protonation site in these co-oligomers.

HPLC Separations of Oligomers Sulfones

Figure 3:
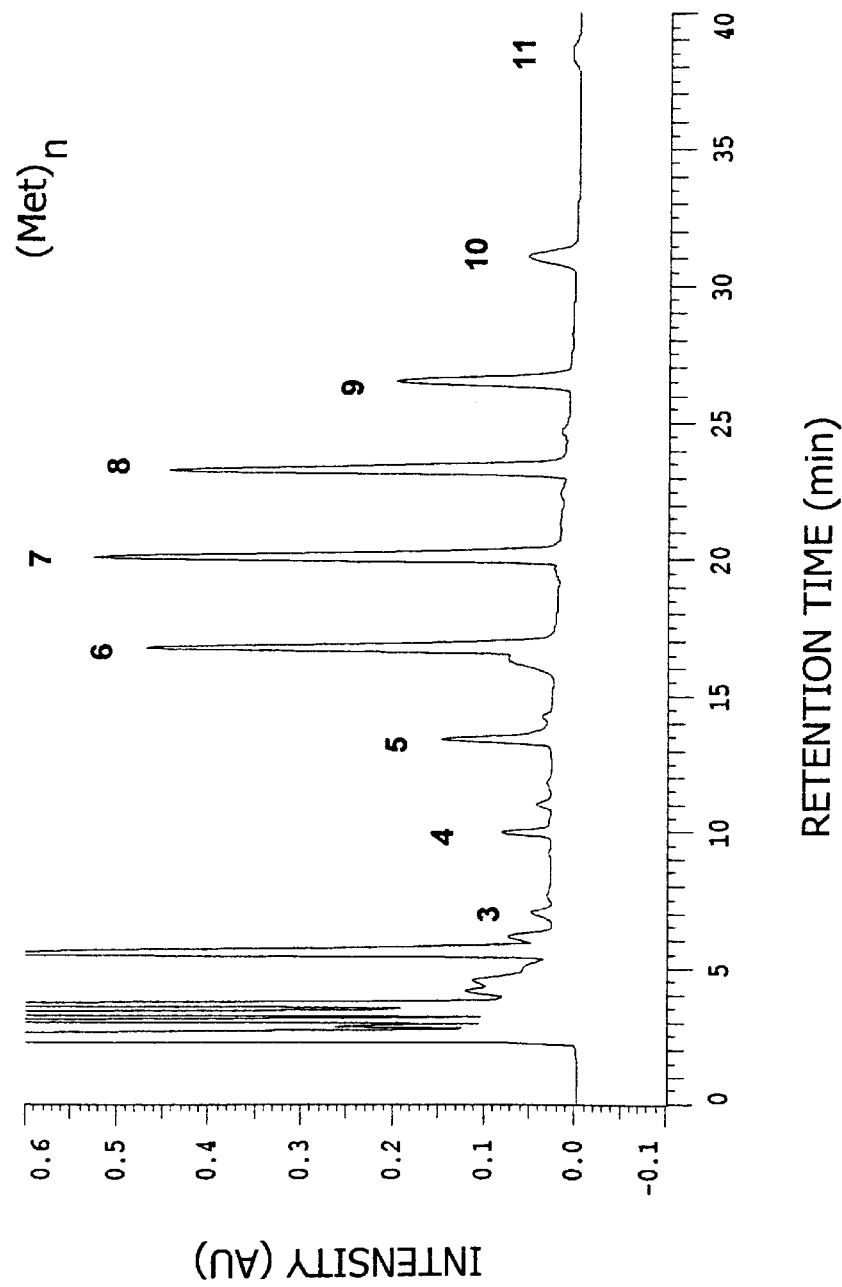
FIG. 3 is a HPLC graph of methionine sulfone oligomers.

The chromatographic separations of poly-methionine sulfones are shown in FIG. 3. A number of well-resolved peaks can be readily observed, of these, nine did not appear in the reagent blank and most likely represent the poly-methionine sulfones. This chromatographic separation is nearly identical to the chromatographic separations reported by Kasai et al. (T. Kasai, T. Tanaka, and S. Kiriyama, *Biosci. Biotech. Biochem.*,56(11) (1992) 1884–1885). However, because of a difference in the separation column or variations in the eluant composition the retention times reported by Kasai for most oligomers were approximately 0.5–0.6 minutes longer than retention times obtained in the present study.

Figure 4:
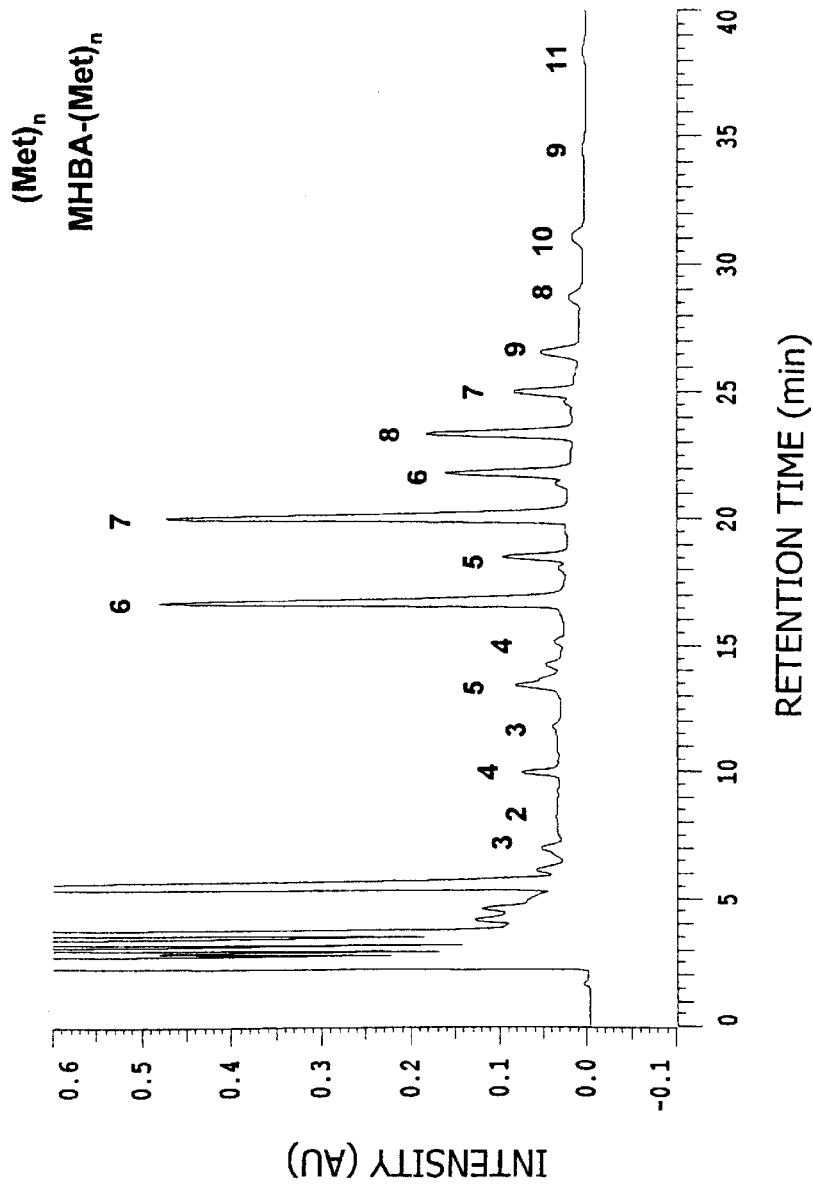
FIG. 4 is a HPLC graph of MHBA-methionine sulfone oligomers after a incubation period of 10 minutes.
Figure 5:
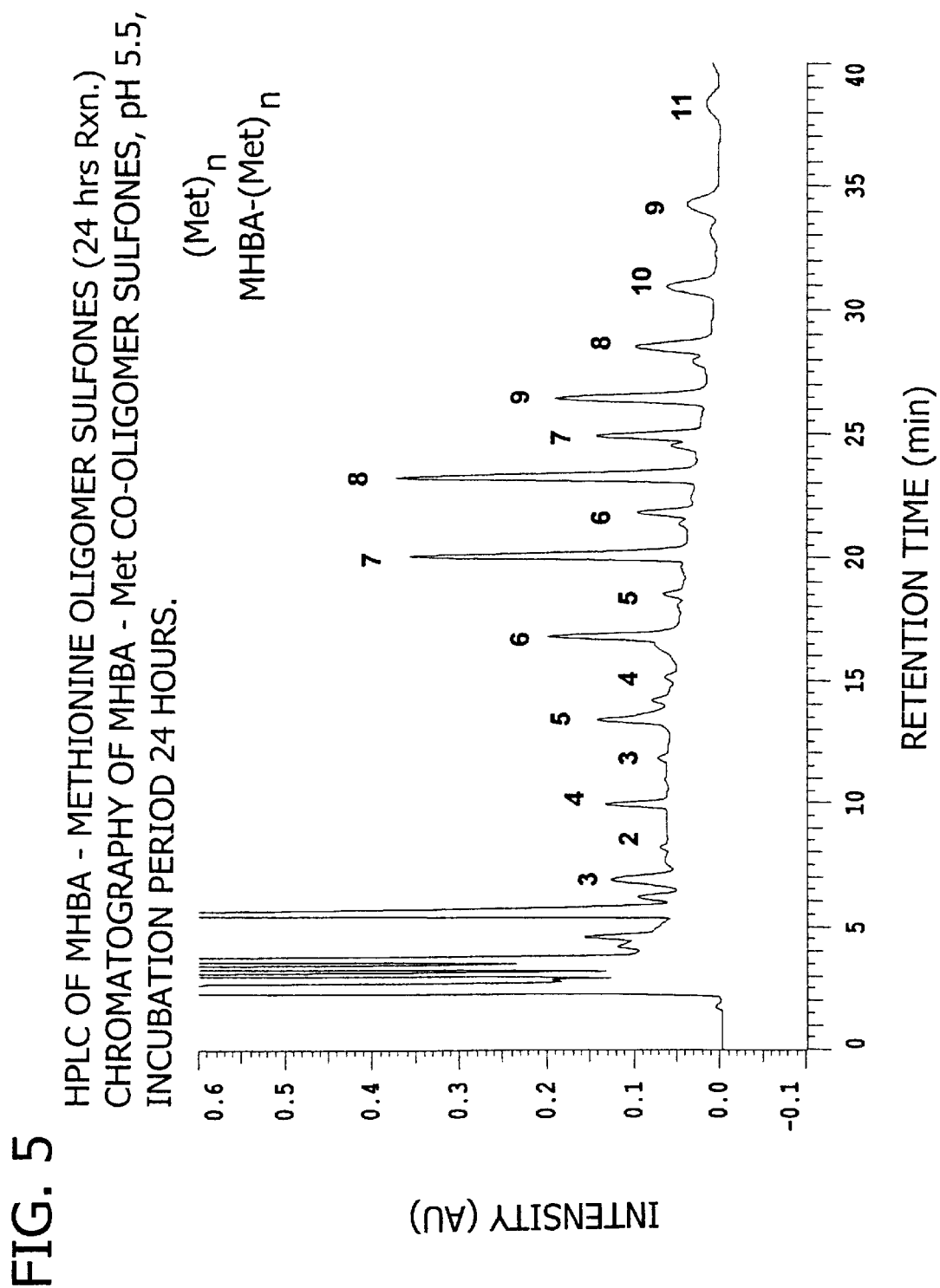
FIG. 5 is a HPLC graph of MHBA-methionine sulfone oligomers after a incubation period of 24 hours.
Figure 6:
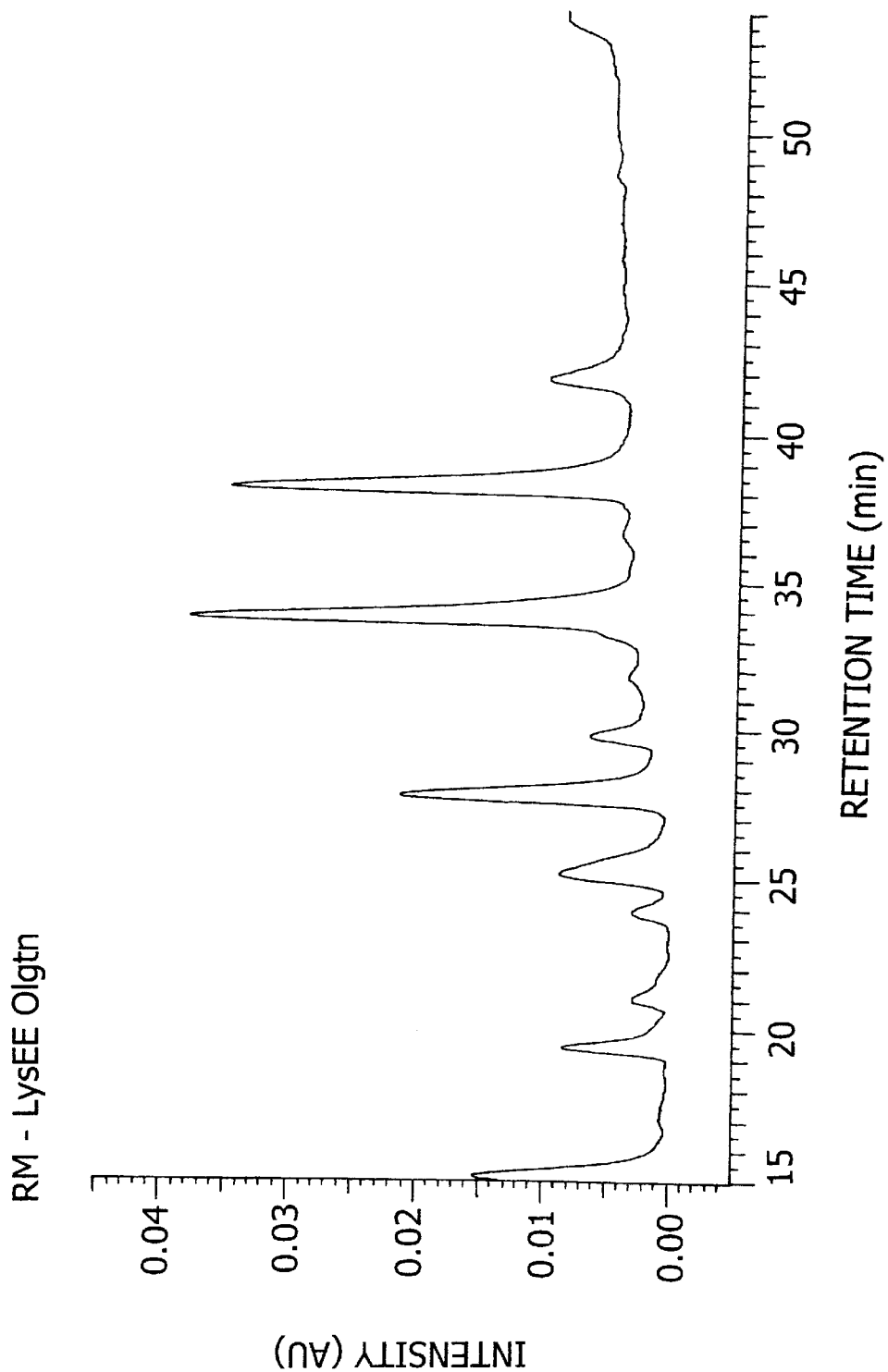
FIG. 6 is a ion-pair liquid chromatography and MALDI-TOF mass spectrometry graph of lysine oligomers synthesized in a reverse micellar system.
Figure 7:
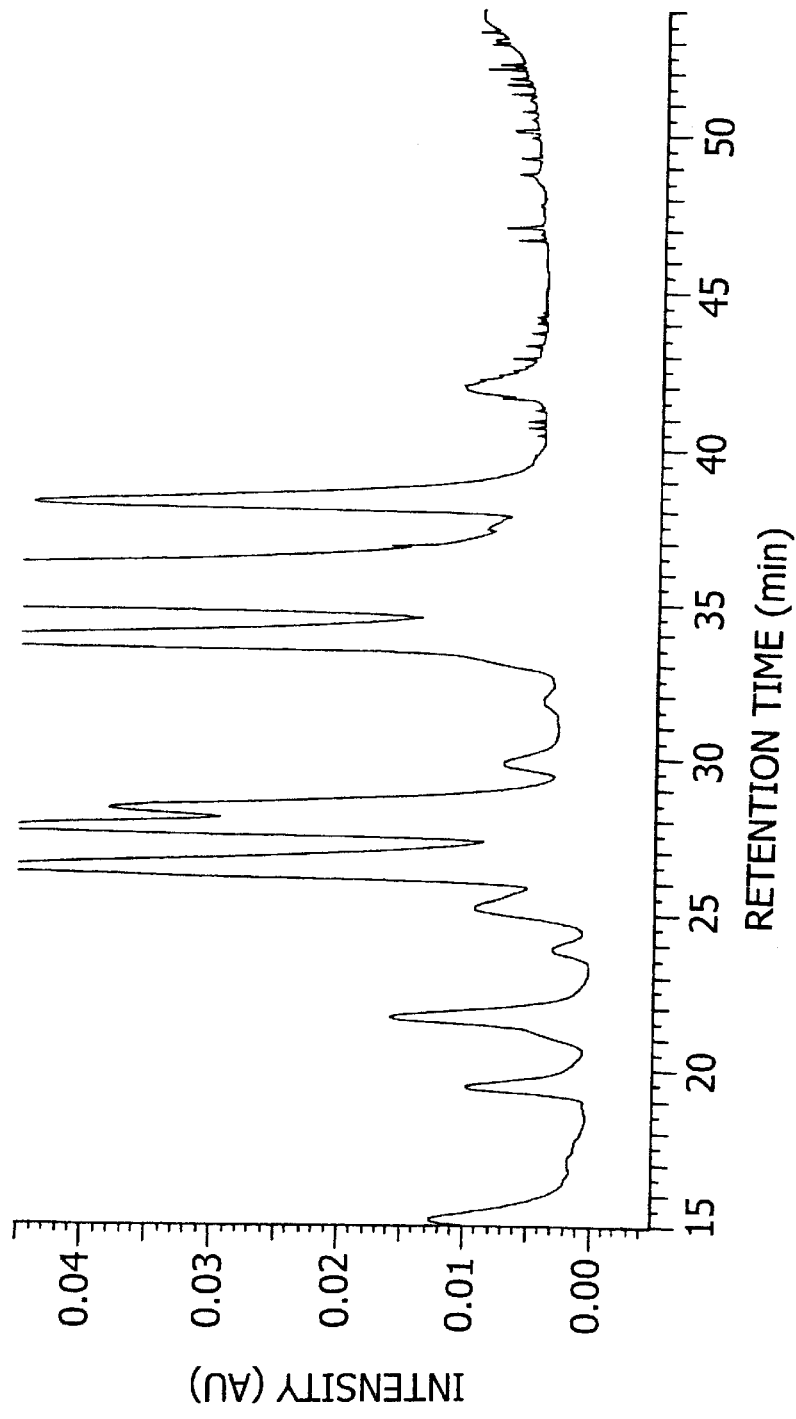
FIG. 7 is a ion-pair liquid chromatography and MALDI-TOF mass spectrometry graph of MHBA-lysine co-oligomers synthesized in a reverse micellar system.
Figure 8:
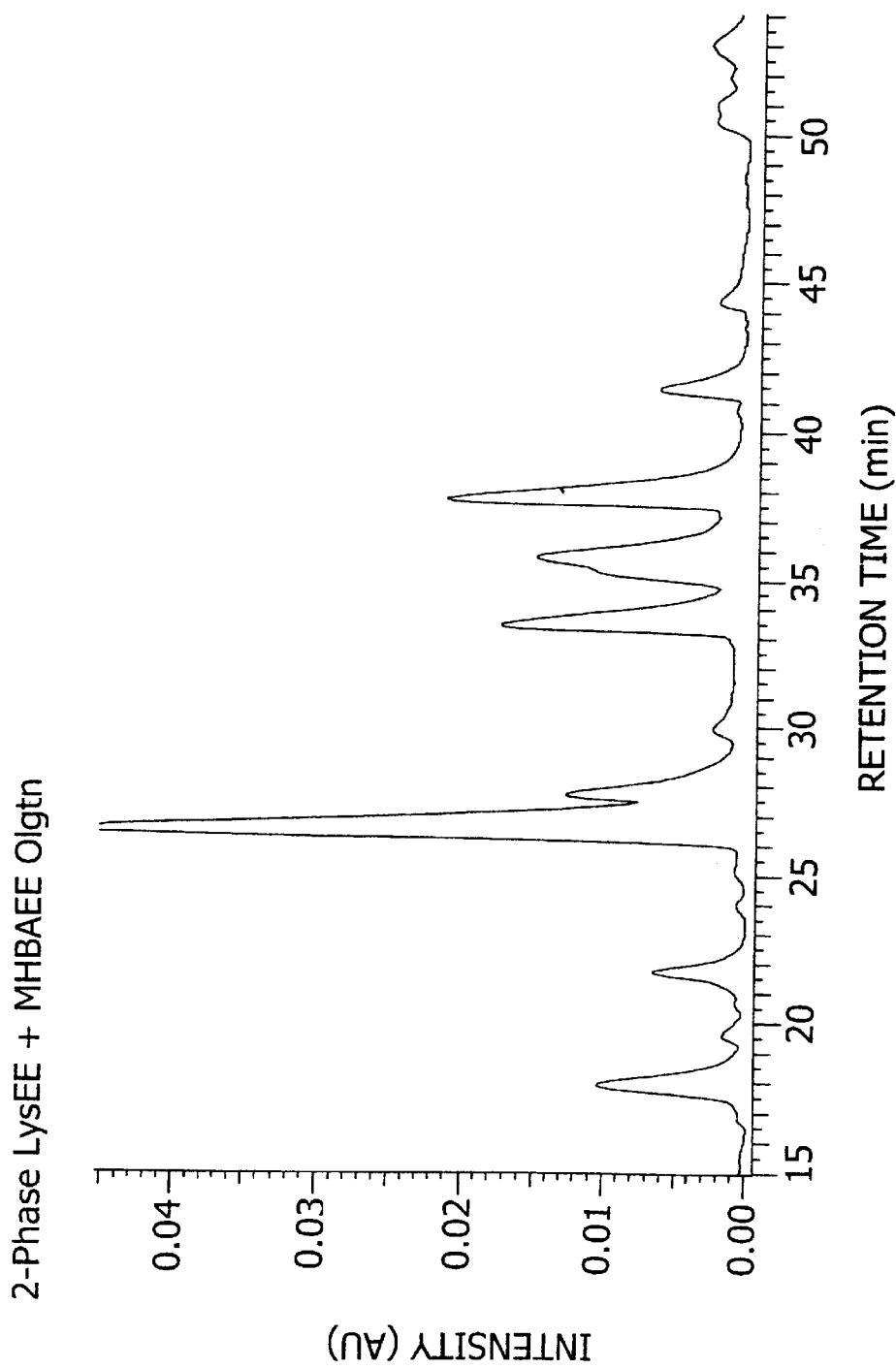
FIG. 8 is a ion-pair liquid chromatography and MALDI-TOF mass spectrometry graph of MHBA-lysine co-oligomers synthesized in a 2-phase system.
Figure 9:
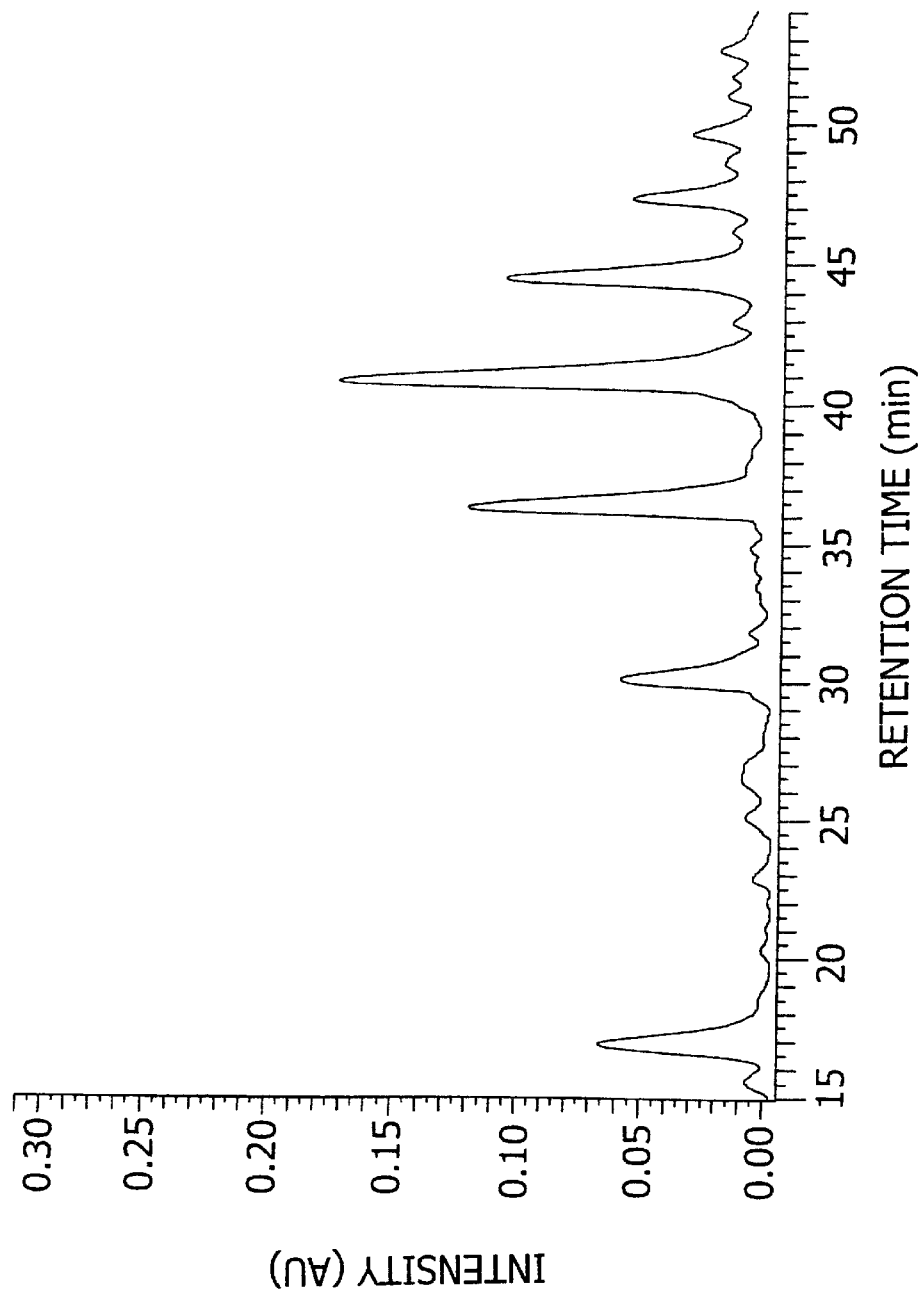
FIG. 9 is a ion-pair liquid chromatography and MALDI-TOF mass spectrometry graph of lysine oligomers synthesized in a 2-phase system.
Figure 10:
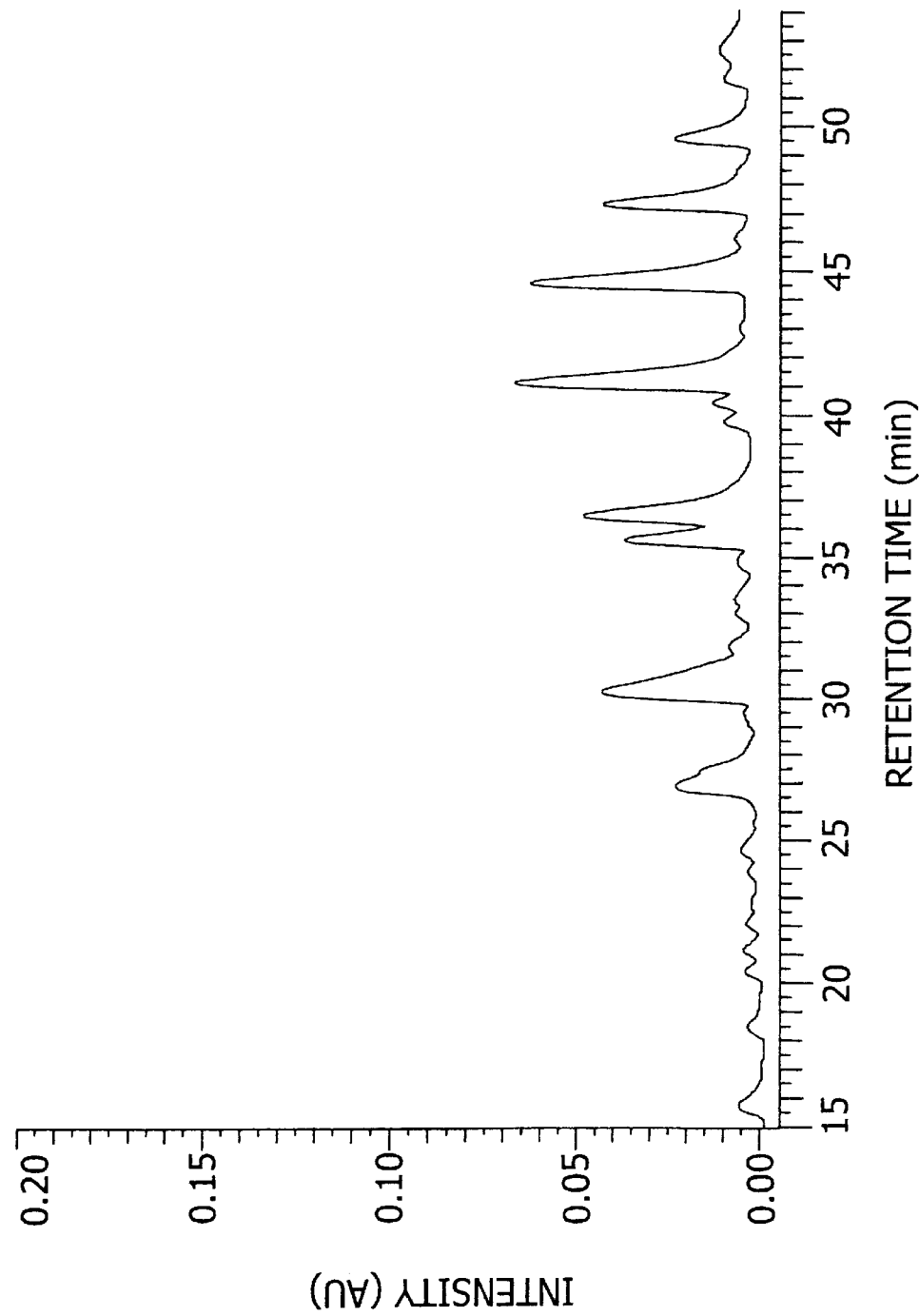
FIG. 10 is a ion-pair liquid chromatography and MALDI-TOF mass spectrometry graph of lysine oligomers synthesized in a 3-phase system.
Figure 11:
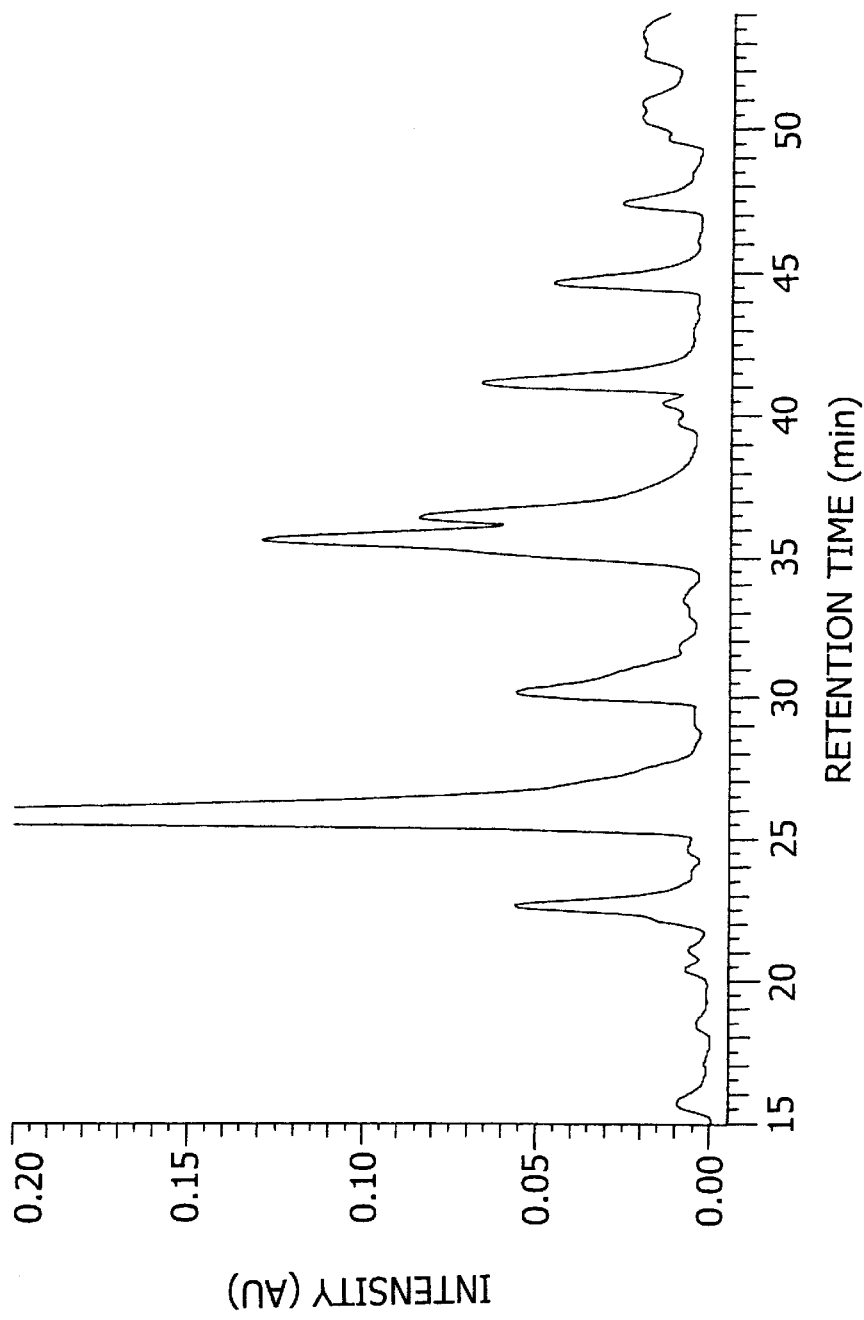
FIG. 11 is a ion-pair liquid chromatography and MALDI-TOF mass spectrometry graph of MHBA-lysine co-oligomers synthesized in a 3-phase system.
Figure 12:
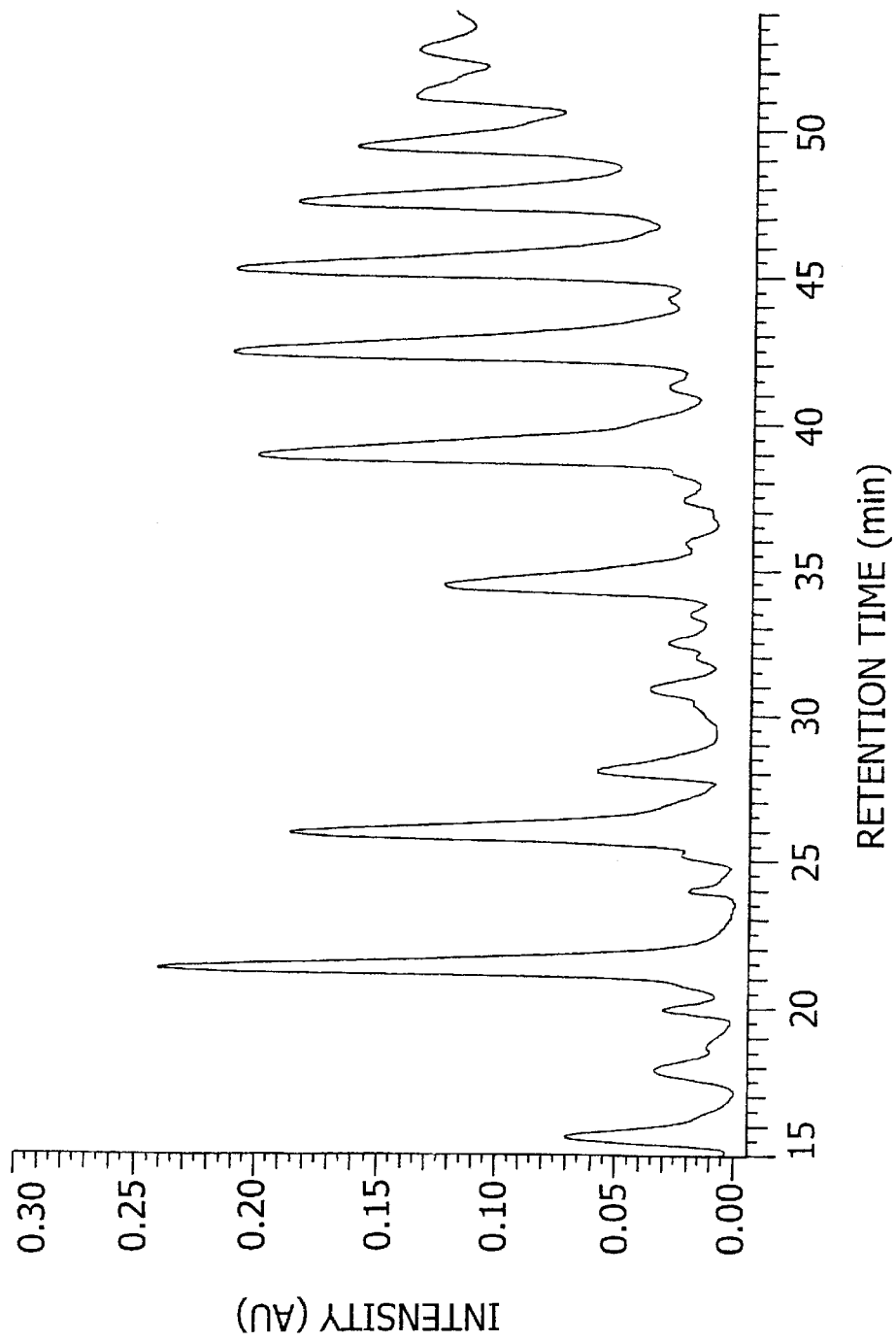
FIG. 12 is a ion-pair liquid chromatography and MALDI-TOF mass spectrometry graph of lysine oligomers synthesized in a reduced volume 2-phase system.
Figure 13:
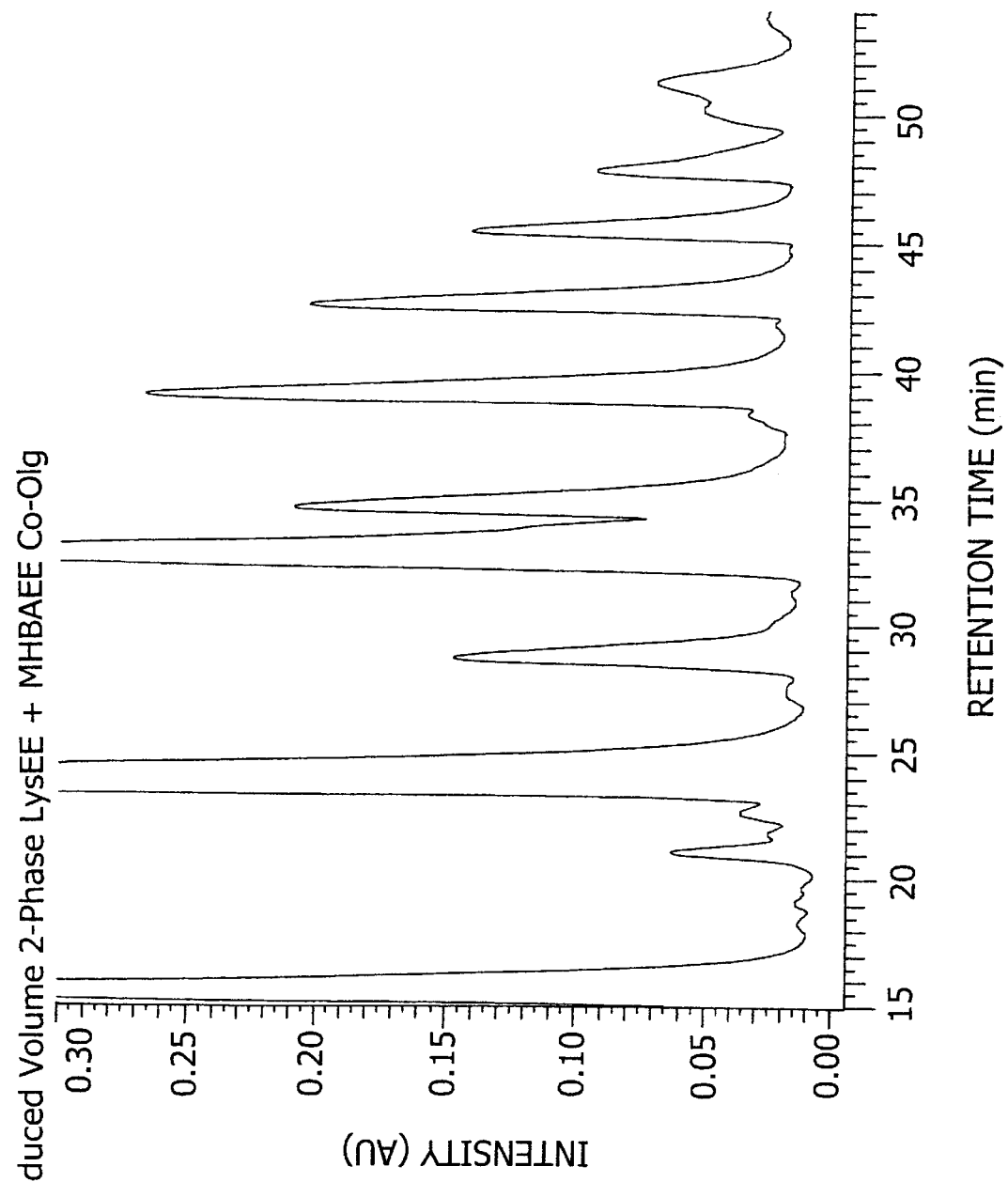
FIG. 13 is a ion-pair liquid chromatography and MALDI-TOF mass spectrometry graph of MHBA-lysine co-oligomers synthesized in a reduced volume 2-phase system.

The chromatographic separation of MHBA-polymethionine sulfones is shown in FIG. 4. This chromatogram contained a number of peaks, which were not present in the poly methionine sulfone chromatogram. This indicates that MHBA is incorporated in the $(Met)^n$ oligomer. The incorporation most likely occurs at the N-terminal end. The resulting MHBA-$(Met)^n$ oligomers, with the terminal hydroxyl, should be less polar than the corresponding $(Met)^n$ oligomers with the terminal amine moiety. Therefore, the MHBA containing oligomers should elute later than the corresponding Met oligomers and this appears to be the case. The elution times for methionine sulfones and MHBA -methionine sulfones are given in Table I. The chromatographic separations of methionine oligomer (sulfones) obtained after different incubation periods indicate that the relative abundance of methionine oligomers is dependent on the incubation period. The abundance of longer chain oligomers was higher in oligomers obtained after 24 hours incubation (FIG. 5) relative to the oligomers obtained after 10 minutes incubation (FIG. 4). It can be readily observed that the concentrations of longer chain oligomers increased with an increase in the incubation period. Chromatographic results also indicate that presence of MHBA may affect the relative distribution of methionine oligomers. These results are significant in light of the reports in the literature, which suggest that the uptake of methionine oligomers is dependent on the size of the oligomers.

TABLE 1

Elution Times of Met and MHBA-Met Oligomer Sulfones

| Oligomer | Elution Time (mins) Present Study | Elution Time (mins) Kasai et al. |
|---|---|---|
| (Met)$_4$ (SEQ ID NO: 1) | 10.0 | NR |
| MHBA- (Met)$_3$ (SEQ ID No 10) | 11.8 | NA |
| (Met)$_5$ (SEQ ID NO: 2) | 13.4 | 14.0 |
| MHBA- (Met)$_4$ (SEQ ID NO: 11) | 15.1 | NA |
| (Met)$_6$ (SEQ ID NO: 3) | 16.8 | 17.8 |
| MHBA- (Met)$_5$ (SEQ ID NO: 7) | 18.5 | NA |
| (Met)$_7$ (SEQ ID NO: 4) | 20.1 | 21.0 |
| MHBA- (Met)$_6$ (SEQ ID NO: 8) | 21.8 | NA |
| (Met)$_8$ (SEQ ID NO: 5) | 23.3 | 24.0 |
| MHBA- (Met)$_7$ (SEQ ID NO: 9) | 24.9 | NA |
| (Met)$_9$ (SEQ ID NO: 6) | 26.5 | 26.9 |
| MHBA- (Met)$_8$ (SEQ ID NO: 12) | 28.6 | NA |
| (Met)$_{10}$ (SEQ ID NO: 13) | 31.1 | 29.5 |
| MHBA- (Met)$_9$ (SEQ ID NO: 14) | 34.2 | NA |

NR: Not Reported
NA: Not Available

EXAMPLE 2

Oligomerization and co-oligomerization of lysine and MHBA

Protease catalyzed synthesis of water insoluble amino acid oligomers in aqueous media is driven by precipitation. The synthesis of water soluble oligomers of amino acids, such as lysine can be controlled only in mixed phase systems where the equilibria is shifted in favor of the synthesis of polypeptides due to enhanced partitioning of peptide in the organic phase. Puigserver et. al.[1] reported a procedure for papain catalyzed polymerization of lysine. The procedure involved binding of papain to modified PEG (MW 2000 or 5000) and the bound enzyme was used for synthesis of poly lysine in a two phase reaction mixture. A similar procedure was adopted to explore the feasibility co-oligomerization of lysine and MHBA. This procedure was found to be cumbersome and did not yield any discernable MHBA lysine co-oligomers in our laboratory. A summary of this procedure and three new procedures evaluated to bring about co-oligomerization of MHBA with lysine and other polar dibasic amino acids is given in the following section.

PEG Bound Papain System (Puigserver's Method)

10 mM of substrate was added to 98 mL of toluene along with 0.8 mL of Diisopropyl amino ethyl and 0.2 mL of mercaptoethanol, followed by 17 mM of PEG$_{2000}$ modified Papain. The mixture was allowed to incubate for 24 hours, before being evaporated and redissolved in deionized water and analyzed on a ion-pair liquid chromatography column.

Two Phase Toluene:Water System

This solvent system was evaluated with varied phase ratios, two of which are described below:

a) 10 mM of substrate was added to 98 mL of toluene along with 0.8 mL of Diisopropyl amino ethyl and 0.2 mL of mercaptoethanol, followed by 1 mL of aqueous papain suspension. The mixture was allowed to incubate for 24 hours, before being evaporated and redissolved in DI water and analyzed on a ion-pair liquid chromatography column.

b) 100 mM of substrate was added to 8.9 mL of toluene along with 0.08 mL of Diisopropyl amino ethyl and 0.02 mL of mercaptoethanol. This was followed by 1 mL of aqueous papain suspension, which resulted in a two phase system. The mixture was allowed to incubate for 24 hours, before being evaporated and redissolved in DI water and analyzed on an ion-pair liquid chromatography column.

Reverse Micellar System 10 mM of substrate was dissolved in 98 mL of a reverse micellar solution containing 150 mM of AOT (3.33 g), 0.8 mL of diisopropyl amino ethyl and 0.2 mL of mercaptoethanol in isooctane. 1 mL of Aqueous papain solution was added to the mixture and allowed to incubate for 24 hours, at the end of which the mixture was heated to denature the enzyme and the oligomeric products extracted with 1 M NaCl solution. The solution was later analyzed on a ion-pair liquid chromatography column.

Three Phase DFP:Octane:Water System

To a two phase system comprising of 4.45 mL of DFP and 4.45 mL of octane was added 100 mM of substrate along with 0.08 mL of Diisopropyl amino ethyl and 0.02 mL of mercaptoethanol. The addition of 1 mL of aqueous papain suspension which is insoluble in either of the phases converts this system to a three phase system. The mixture was allowed to incubate for 24 hours, before being evaporated and redissolved in DI water and analyzed on a ion-pair liquid chromatography column Results The yield and the degree of oligomerization were determined with ion-pair liquid chromatography and MALDI-TOF mass spectrometry. These results appear in FIGS. 6 to 13.

TABLE 2

Procedure for the various methods used to synthesize lysine oligomers and MHBA-lysine co-oligomers

| | Lysine Oligomerization | | | | | MHBA-lysine Co-oligomerization | | | | |
|---|---|---|---|---|---|---|---|---|---|---|
| Components | Pgsr[f] | 2-f[g] | RM[h] | 3-f[i] | RV 2-f[j] | Pgsr[f] | 2-f[g] | RM[h] | 3-f[i] | RV 2-f[j] |
| LysEE.2HCl(mM) | 10 | 10 | 10 | 100 | 100 | 5 | 10 | 10 | 50 | 50 |
| MHBA analog mM | | | | | | 5 | 10 | 10 | 50 | 50 |
| i-Pr$_2$NH$_2$Et (% v/v)[a] | 0.8 | 0.8 | 0.8 | 0.8 | 0.8 | 0.8 | 0.8 | 0.8 | 0.8 | 0.8 |
| SCH$_2$CH$_2$OH (% v/v)[b] | 0.2 | 0.2 | 0.2 | 0.2 | 0.2 | 0.2 | 0.2 | 0.2 | 0.2 | 0.2 |
| Papain (% v/v)[c] | | 1 | 1 | 10 | 10 | | 1 | 1 | 10 | 10 |
| Toluene (% v/v) | 98 | 98 | | | 89 | 98 | 98 | | 0 | 89 |
| Isooctane (% v/v) | | | 98 | | | | | 98 | | |
| DFP (% v/v)[d] | | | | 44.5 | | | | | 44.5 | |
| Octane (% v/v) | | | | 44.5 | | | | | 44.5 | |
| AOT (mM)[e] | | | 150 | | | | | 150 | | |

TABLE 2-continued

Procedure for the various methods used to synthesize lysine oligomers and MHBA-lysine co-oligomers

| Components | Lysine Oligomerization | | | | | MHBA-lysine Co-oligomerization | | | | |
|---|---|---|---|---|---|---|---|---|---|---|
| | Pgsr[f] | 2-f[g] | RM[h] | 3-f[i] | RV 2-f[j] | Pgsr[f] | 2-f[g] | RM[h] | 3-f[i] | RV 2-f[j] |
| PEG-Papain (mM) | 17 | | | | | 17 | | | | |
| Yields (%) | 0 | 17 | 22 | 95 | 90 | 0 | 17 | 22 | 95 | 90 |

[a]Di-isopropyl amino ethyl
[b]Mercaptoethanol
[c]Aqueous suspension of papain obtained from Sigma
[d]Decafluoropentane
[e]Aerosol-OT, Dioctyl sulfor succinate
[f]Puigserver's method
[g]Two-phase method
[i]Three Phase Method
[h]Reverse Micellar method
[i]Three Phase method
[j]Reduced volume (10%) m
[1]Anne Frejancic, Antoine Puigserver and Hubert Gaertner, Papain-Catalyzed Polymerization of Amino Acids in Low Water Organic Solvents, Biotech. Lett., 1991, 13 (3), 161–166.

EXAMPLE 3

MHBA-methionine and MHBA-lysine co-polymers were synthesized enzymatically through a papain-catalyzed reaction along with poly-methionine and poly-lysine (as controls) as described in Examples 1 and 2. The biological release of the amino acids from the oligomers was examined using several digestive enzymes including, pepsin, trypsin, chymotrypsin, intestinal peptidase and carboxypeptidase. The oligomers were dissolved at 10 mg/mL in 0.15 HCl (pH 2.5) or 50 mM KPO4 (pH 7.5). Samples (0.5mL) were incubated with 10 units of each enzyme for 2 hours at 37° C. The extent of digestion was quantified by measurement of newly released amino groups and their reaction with o-Phthalaldehyde (OPA) and 2,4,6-trinitrobenzene sulfonic acid (TNBSA). Acid hydrolysis was prepared by complete hydrolysis of 10 mg/mL polymers in 6 M HCl for 24 hours at 110° C. Results are summarized below in Table II.

Results show that MHBA-methionine and MHBA-lysine can be hydrolyzed by strong acid and heat. MHBA-met is digested only 3.5% by pepsin and not at all by the other proteases. Poly-lysine can be digested by intestinal peptidase (20% in 2 hours at 37° C.) but not by other proteases. MHBA-lysine is not digested by any of the proteases tested. In conclusion, these data suggest the lack of enzymatic digestion of MHBA-met and MHBA-lysine polymer was caused by a structural difference instead of solubility of the polymers.

TABLE 3

ENZYMATIC DIGESTION OF AMINO ACID POLYMERS

| Enzyme | Poly-Lys (~8mer) | MHBA-met | Poly-met | MHBA-Lys | Poly-Lys (~4mer) |
|---|---|---|---|---|---|
| pepsin | 0 | 0.030 (3%) | 0.062 (15%) | 0 | 0 |
| trypsin | 0.008 (15%) | 0 | 0 | 0 | 0 |
| chymotrypsin | 0 | 0 | 0 | 0 | 0 |
| intestinal peptidase | 0.013 (25%) | 0 | 0.052 (13%) | 0 | (TNBSA, ~20%) |
| carboxy-peptidase A | 0 | 0 | 0 | 0 | 0 |

TABLE 3-continued

ENZYMATIC DIGESTION OF AMINO ACID POLYMERS

| Enzyme | Poly-Lys (~8mer) | MHBA-met | Poly-met | MHBA-Lys | Poly-Lys (~4mer) |
|---|---|---|---|---|---|
| acid hydrolysis (-initial value) | 0.052 | 0.868 | 0.406 | 0.063 | 0.093 |

Readings were from OPA analysis of 20 μg samples
Hydrolysis was done at 37° C. for 2 hours
(%) refers to % of acid hydrolysis number

EXAMPLE 4

Figure 14A:
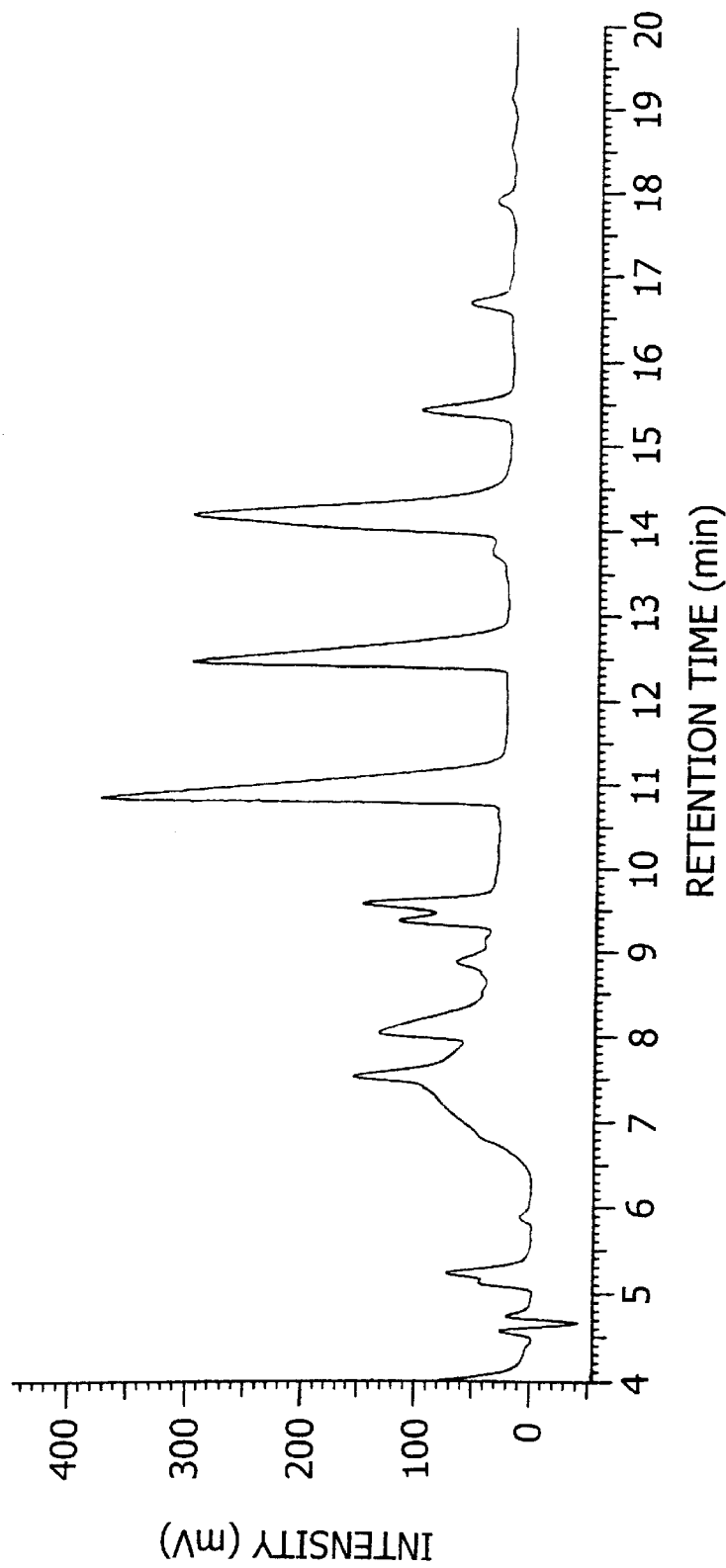
FIG. 14A is a chromatogram of persulfonated methionine oligomers using a UV absorption detector.
Figure 16:
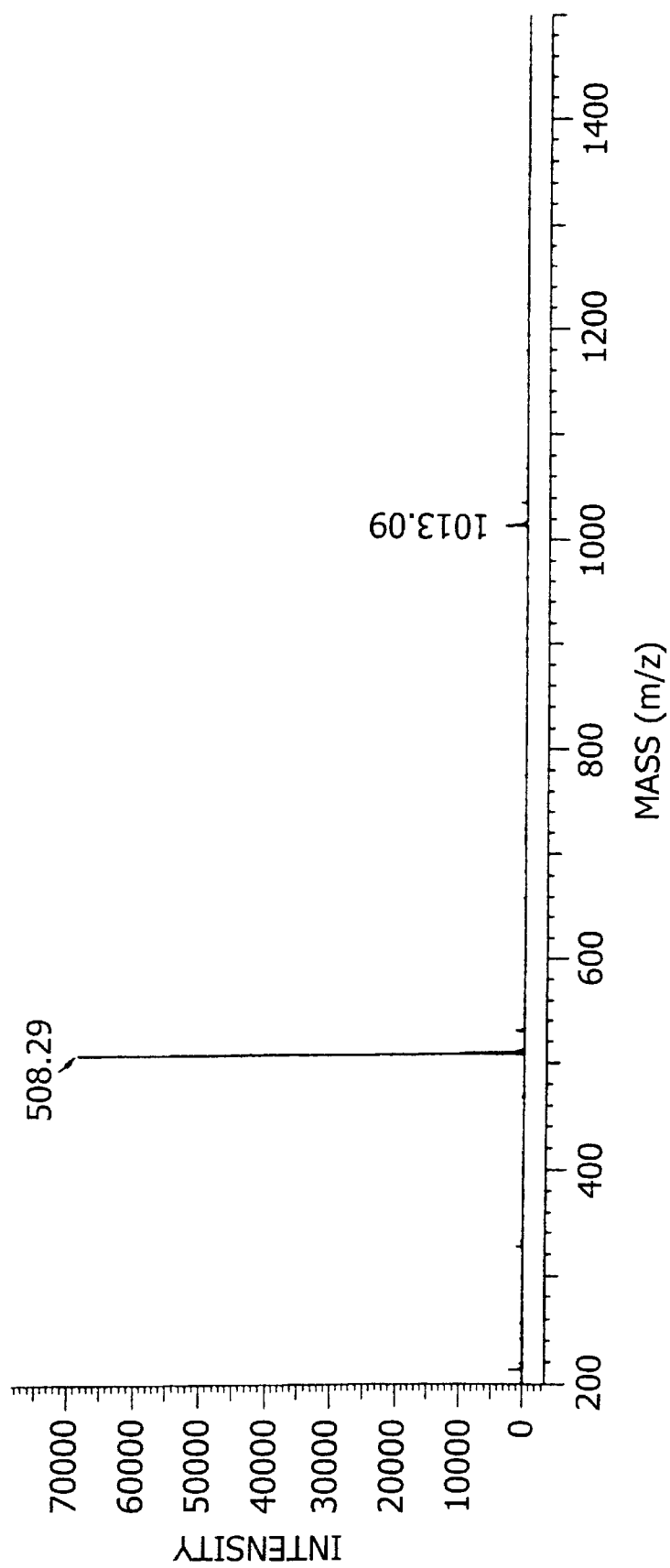
FIG. 16 is a positive ion ESI spectra of $(Met)_3$ sulfone peak eluting at 5.27 minutes.
Figure 17:
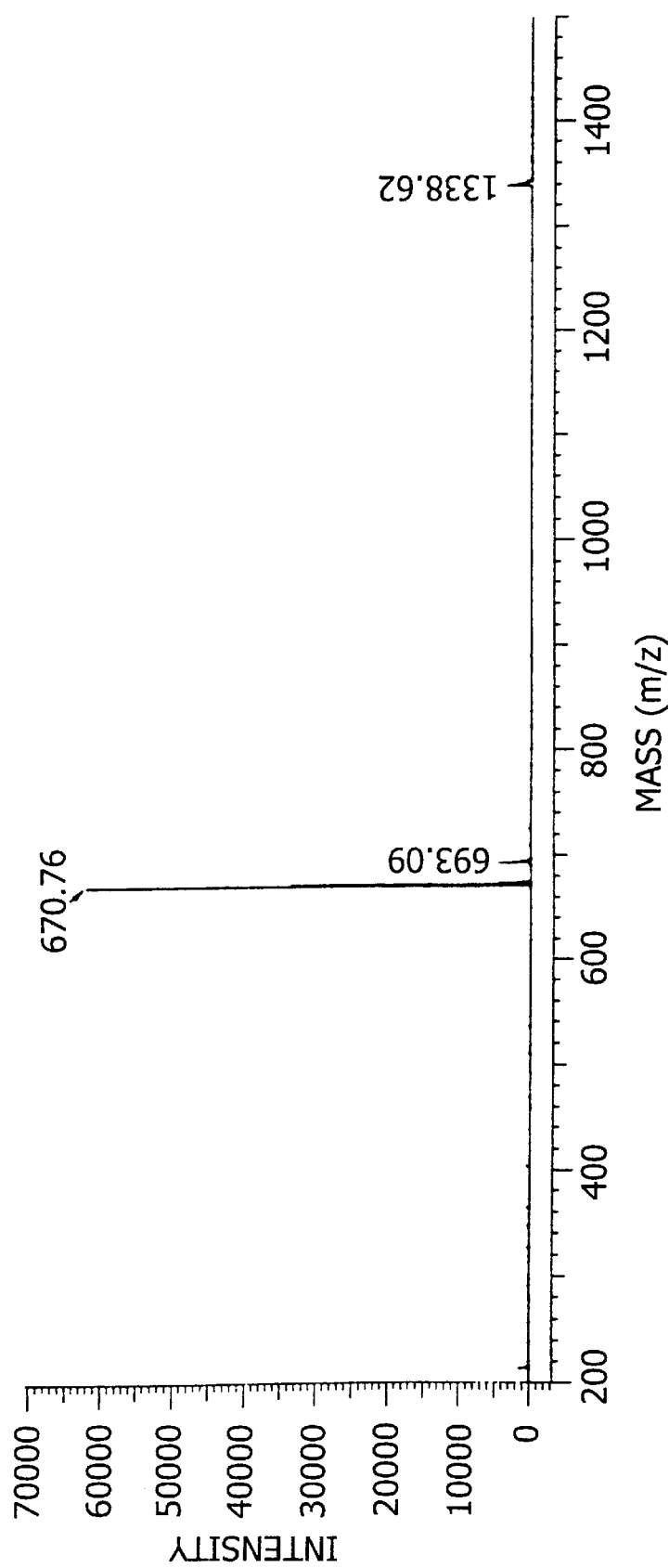
FIG. 17 is a positive ion ESI spectra of $(Met)_4$ sulfone (SEQ ID NO: 1) peak eluting at 7.70 minutes.
Figure 18:
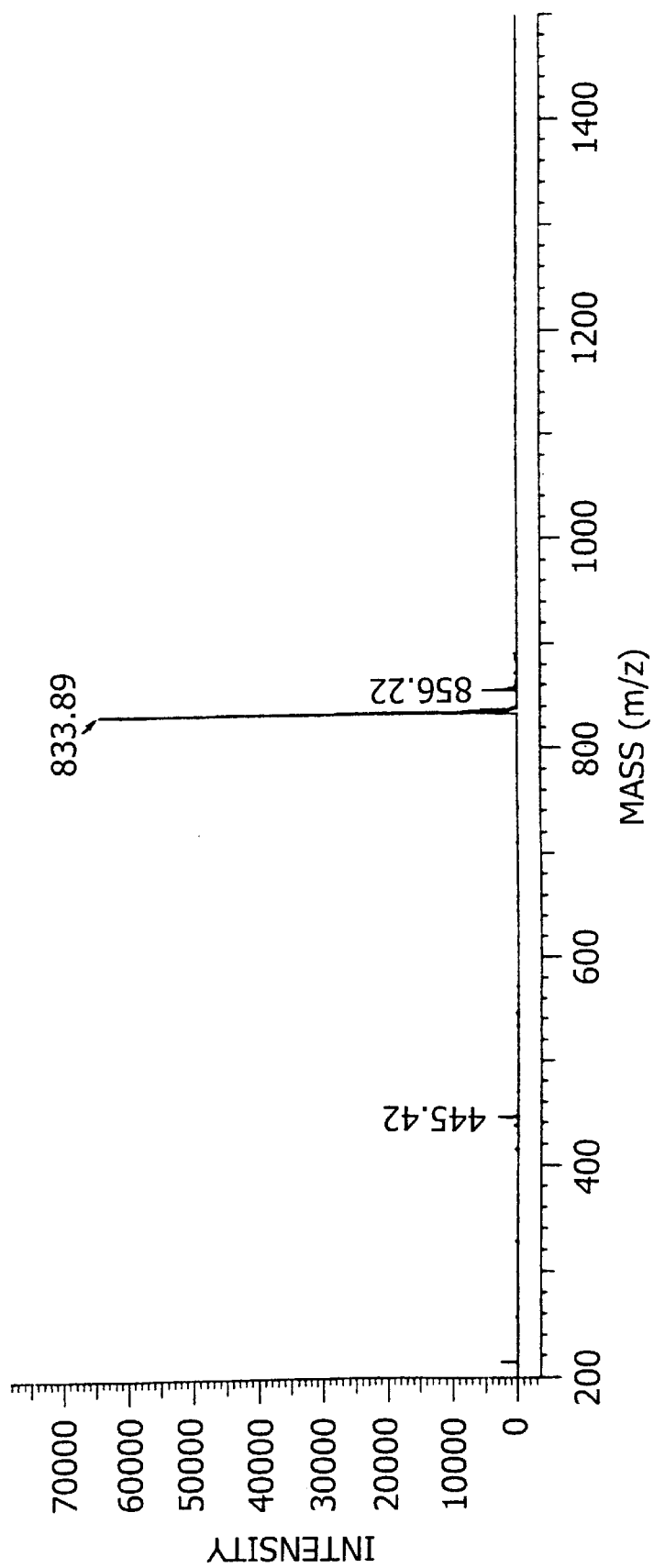
FIG. 18 is a positive ion ESI spectra of $(Met)_5$ sulfone (SEQ ID NO: 2) peak eluting at 9.47 minutes.
Figure 19:
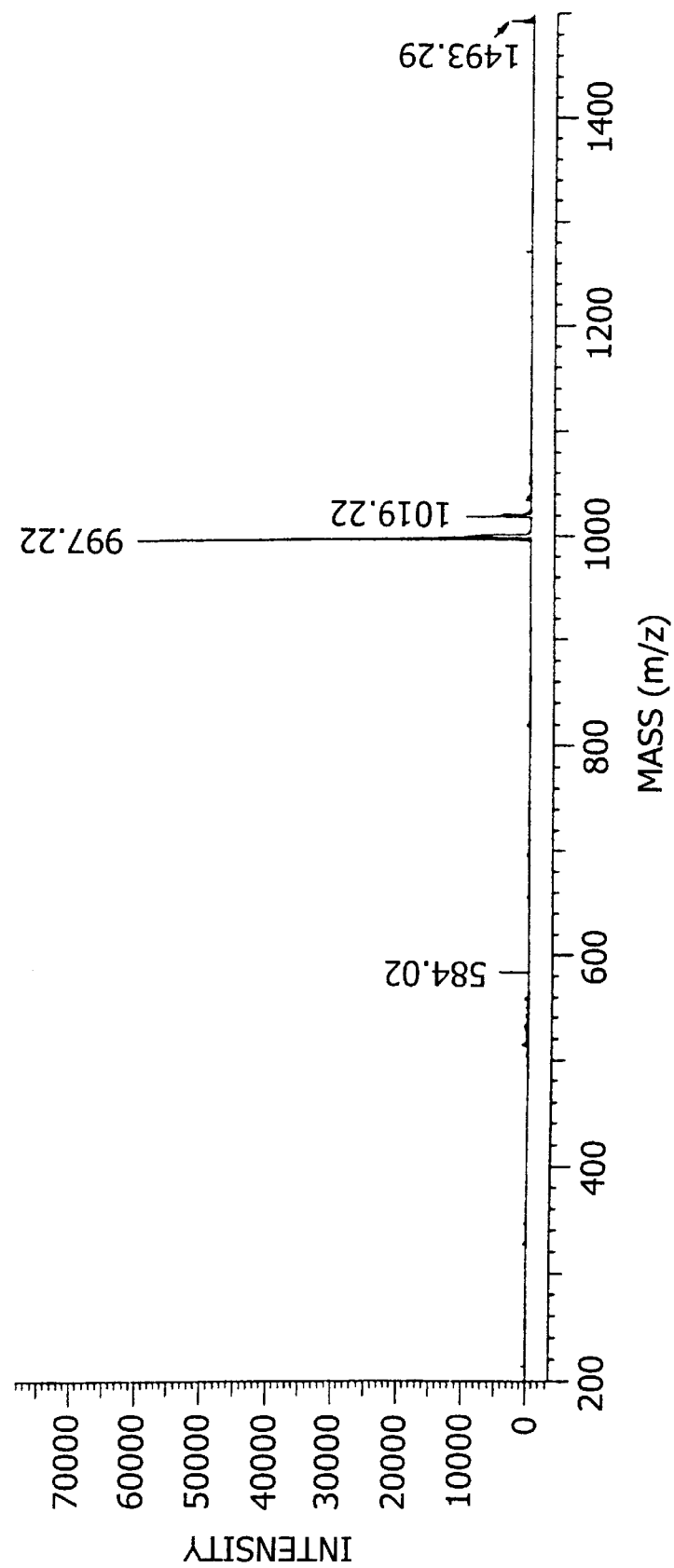
FIG. 19 is a positive ion ESI spectra of $(Met)_6$ sulfone (SEQ ID NO: 3) peak eluting at 11.09 minutes.
Figure 20A:
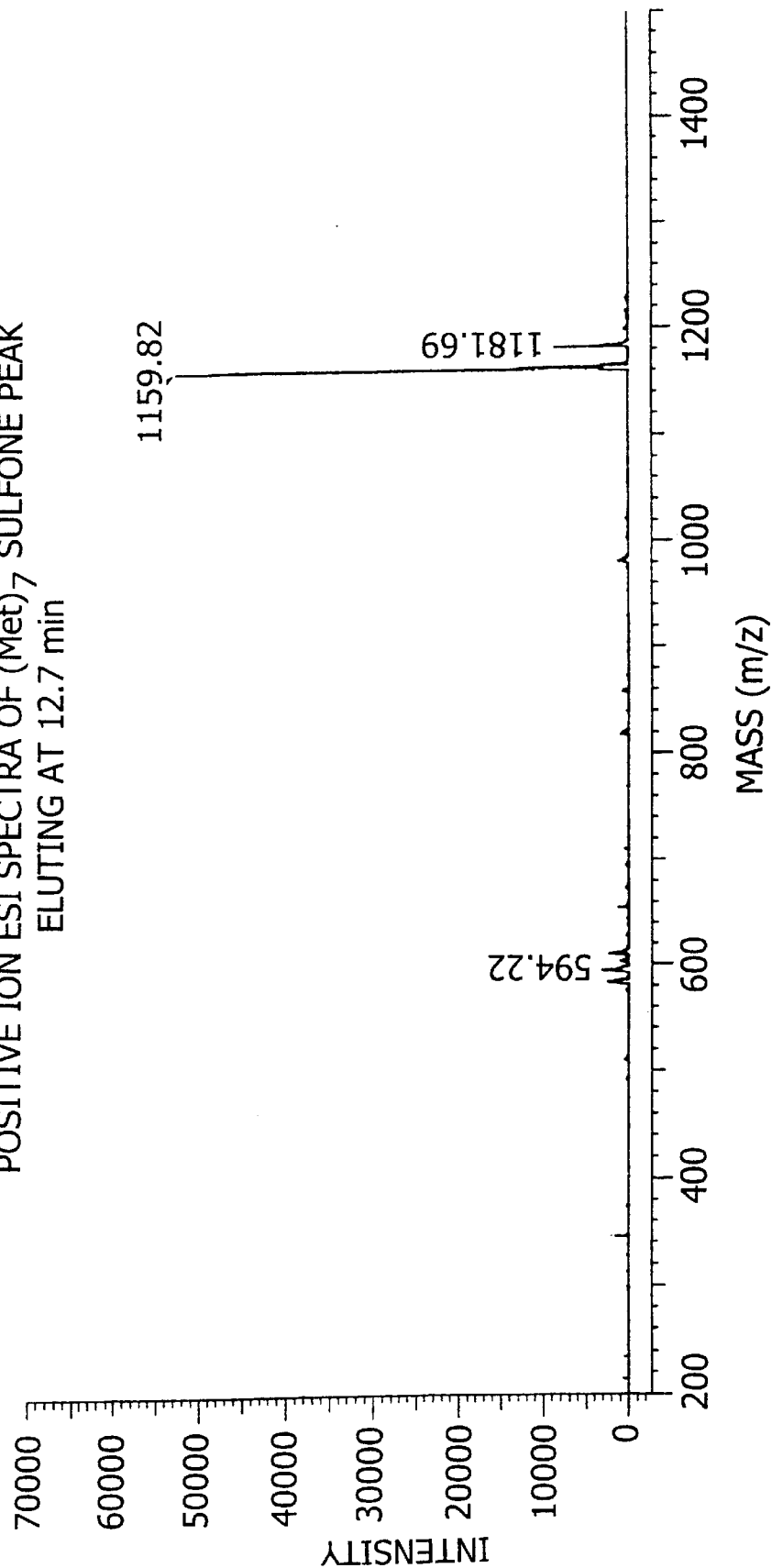
FIG. 20A is a positive ion ESI spectra of $(Met)_7$ sulfone (SEQ ID NO: 4) peak eluting at 12.7 minutes.

LC-ESI MS Characterization of Papain Catalyzed Methionine Oligomers and MHBA-Methionine Co-oligomers Met oligomers and MHBA-Met co-oligomers produced through papain mediated enzymatic reactions at pH 5.5 and pH 9.0 according to the procedure described in Example 1 were subjected to persulfonation. Persulfone derivatives were separated with the reverse phase liquid chromatography (RPLC). The separated oligomers and co-oligomers were monitored with a UV absorption spectrophotometeric detector and an electrospray ionization interface (ESI) mass spectrometer. The absorption wavelength was set at 210 nm. The mass spectrometer was operated in positive and negative ion modes. The outputs of the UV absorption detector and the positive ion ESI-MS are shown in FIGS. 14 and 15.

The chromatogram of (Met)n persulfones obtained with the UV detector and the positive ion total ion chromatogram (TIC) were similar to the chromatograms obtained from earlier with a earlier experiments using a RPLC-Diode Array Detector (DAD) system. These results had indicated the formation of Met homo-oligopeptides and MHBA-Met co-oligomers. The results were supported by data obtained from the matrix assisted laser desorption ionization-mass spectrometry (MALDI-MS) experiments.

The experiments with ESI-MS in the positive ion mode confirmed the formation of methionine oligomers. The ESI-MS spectrum for individual LC peaks provides conclusive evidence for the formation of (Met) to (Met) oligomers. The mass difference between in the molecular masses of successive oligomers was found to be 163, which corresponds to the sulfonated methionine residue.

Spectra corresponding to different peaks are shown in FIGS. 16–20. The general formula for the separated oligomers is:

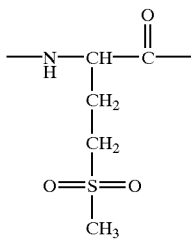

The positive ion TIC of MHBA-(Met)n co-oligomers obtained with ESI-MS did not contain extra peaks observed in the LC-UV chromatogram. The spectra of individual peaks in the MHBA-Met co-oligomers did not provide any evidence for MHBA-(Met)n co-oligomers formation. These results were not unexpected, the lack of pseudo-molecular positive ions in the MALDI-TOF spectra of MHBA-(Met)n in the earlier experiments had led us to the conclusion that MHBA is attached at the N-terminal end of the polymethionine chain. The lack of protonated ions in the MHBA-Met co-oligomers is the result the weak proton affinity of the terminal hydroxyl group.

Figure 21A:
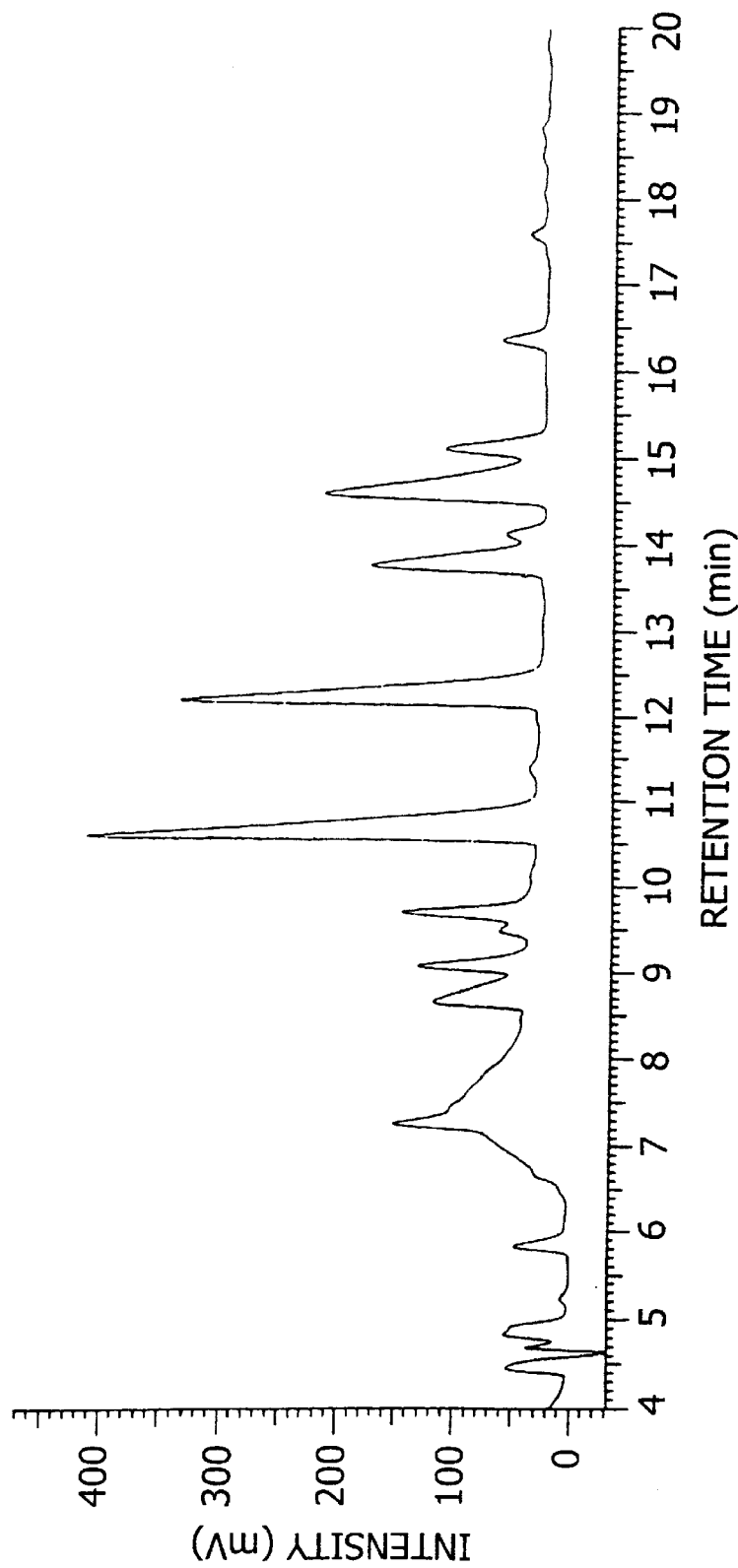
FIG. 21A is a chromatogram of persulfonated methionine oligomers using a UV absorption detector.
Figure 21B:
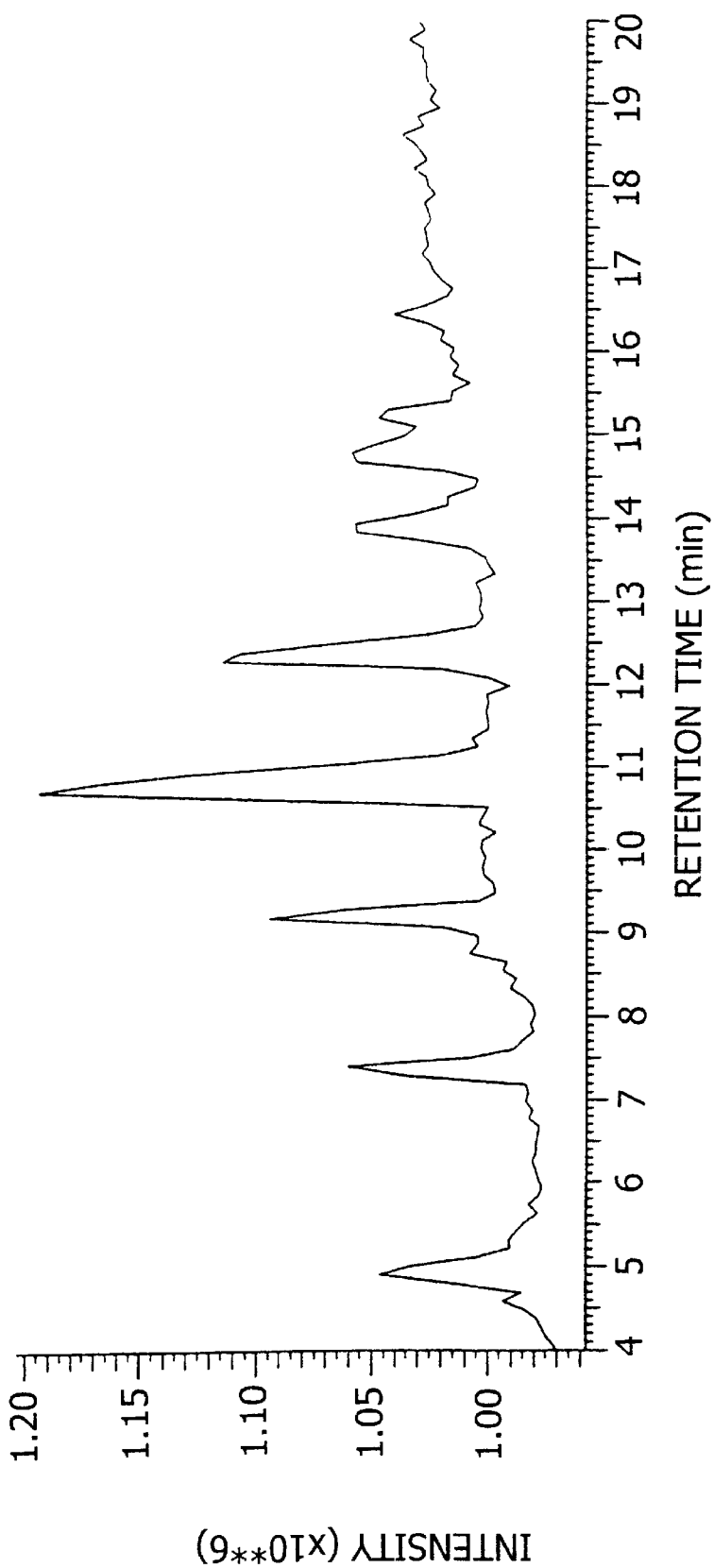
FIG. 21B is a total ion chromatogram ESI-negative ion of persulfonated methionine oligomers.

The confirmation of the MHBA-(Met)n was obtained by monitoring negative ions formed through electron attachment to the (Met)n and MHBA-(Met)n chains. The TIC of MHBA-(Met)n in this case contained extra components (peaks) which corresponded to the extra peaks observed in the LC-UV chromatograms FIGS. 21 and 22.

Figure 25:
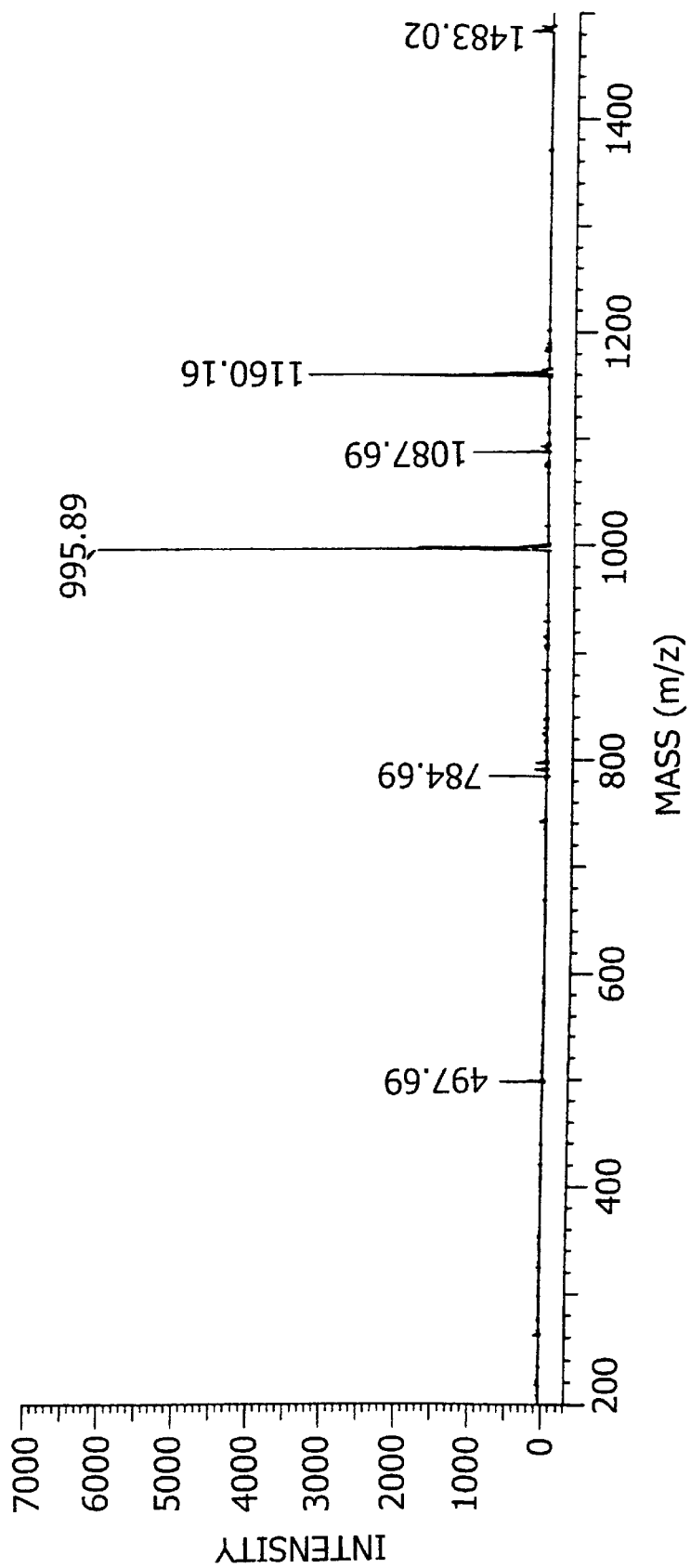
FIG. 25 is a negative ion ESI spectra of HMBA-$(Met)_7$ sulfone (SEQ ID NO: 9) peak eluting at 15.31 minutes.

A few representative spectra for the MHBA-(Met)n peaks are shown in FIGS. 23–25. As expected, the molecular ions for MHBA-(Met)n appear at one mass unit higher than the corresponding (Met)n ions. In addition, the retention times of MHBA-(Met)n peaks are longer than the corresponding (Met)n peaks. This is to be expected since the terminal amine group of the (Met)n imparts higher polarity to methionine oligomers than the terminal hydroxyl to the MHBA-(Met)n co-oligomers.

The presence of sulfonated methionine residue in both (Met)n and the MHBA-(Met)n oligomers chains is again revealed by mass difference of 163 amu between the molecular masses of the separated chromatographic peaks. The mass difference corresponds to the mass of the methionine sulfone residue.

Figure 26:
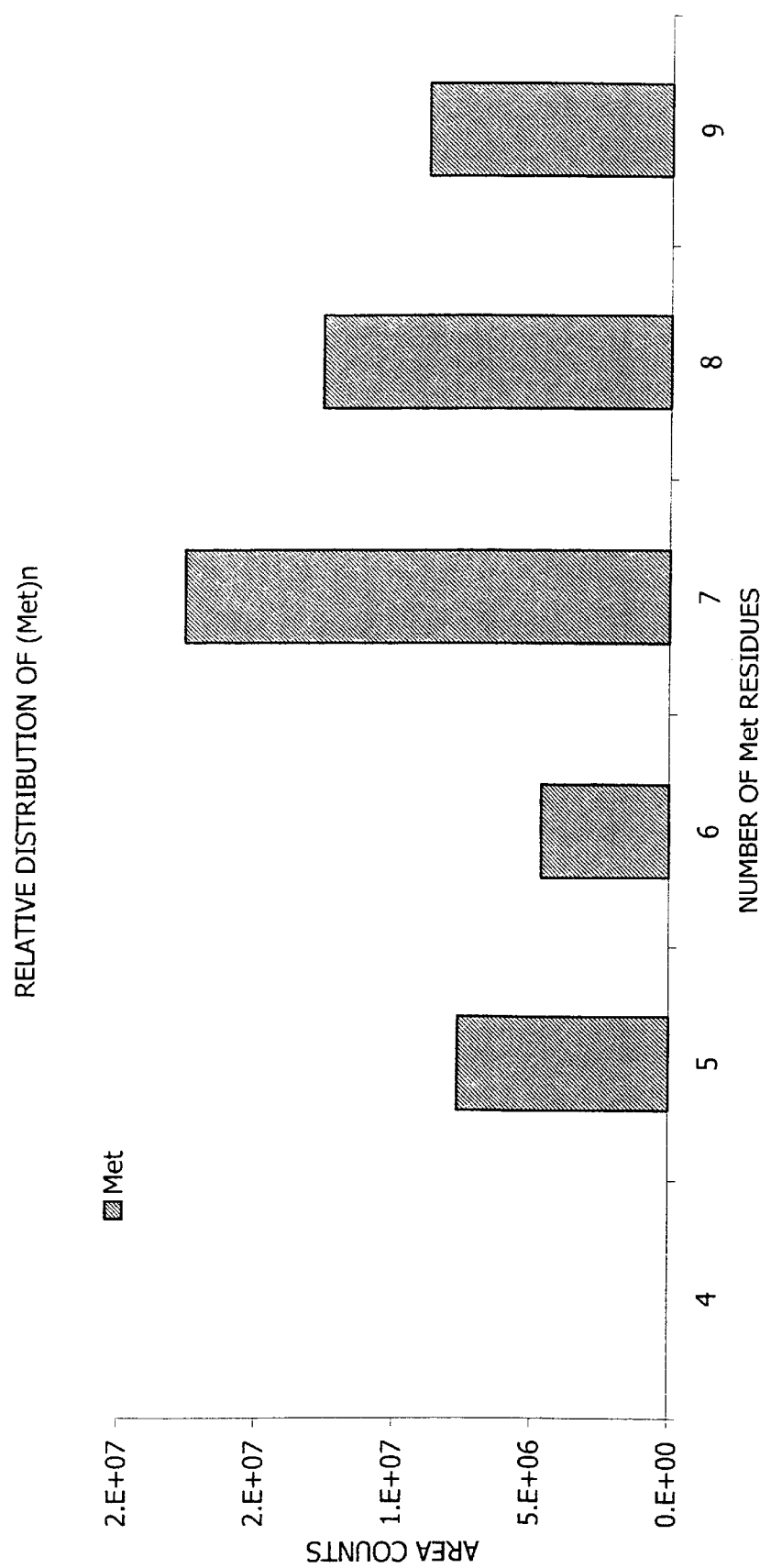
FIG. 26 is a bar graph of the relative distribution of $(Met)_n$ wherein n is the number of methionine residues in the methionine oligomers.
Figure 27:
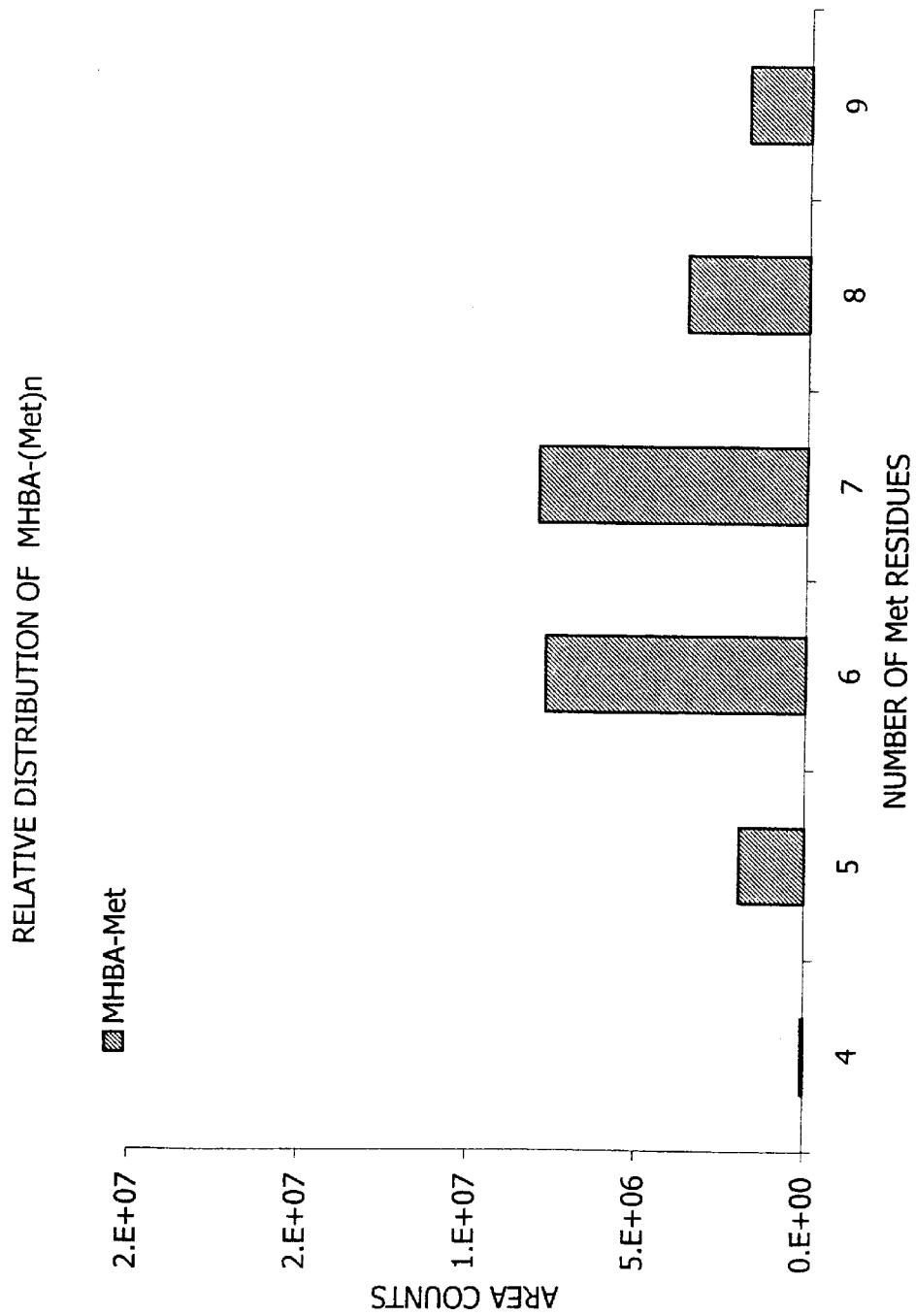
FIG. 27 is a bar graph of the relative distribution of HMBA-$(Met)_n$ wherein n is the number of methionine residues in the HMBA-methionine co-oligomers.

Both the positive ion and negative ion LC-ESIMS data show that the predominant (Met)n are composed of four to ten methionine residues. Likewise, the negative ion LC-ESI data shows that the predominant MHBA-(Met)n co-oligomers contain one MHBA residue and four to nine methionine residues. The relative distribution (Met)n and MHBA-(Met)n oligomers is presented in FIGS. 26 and 27.

EXAMPLE 5

Figure 28A:
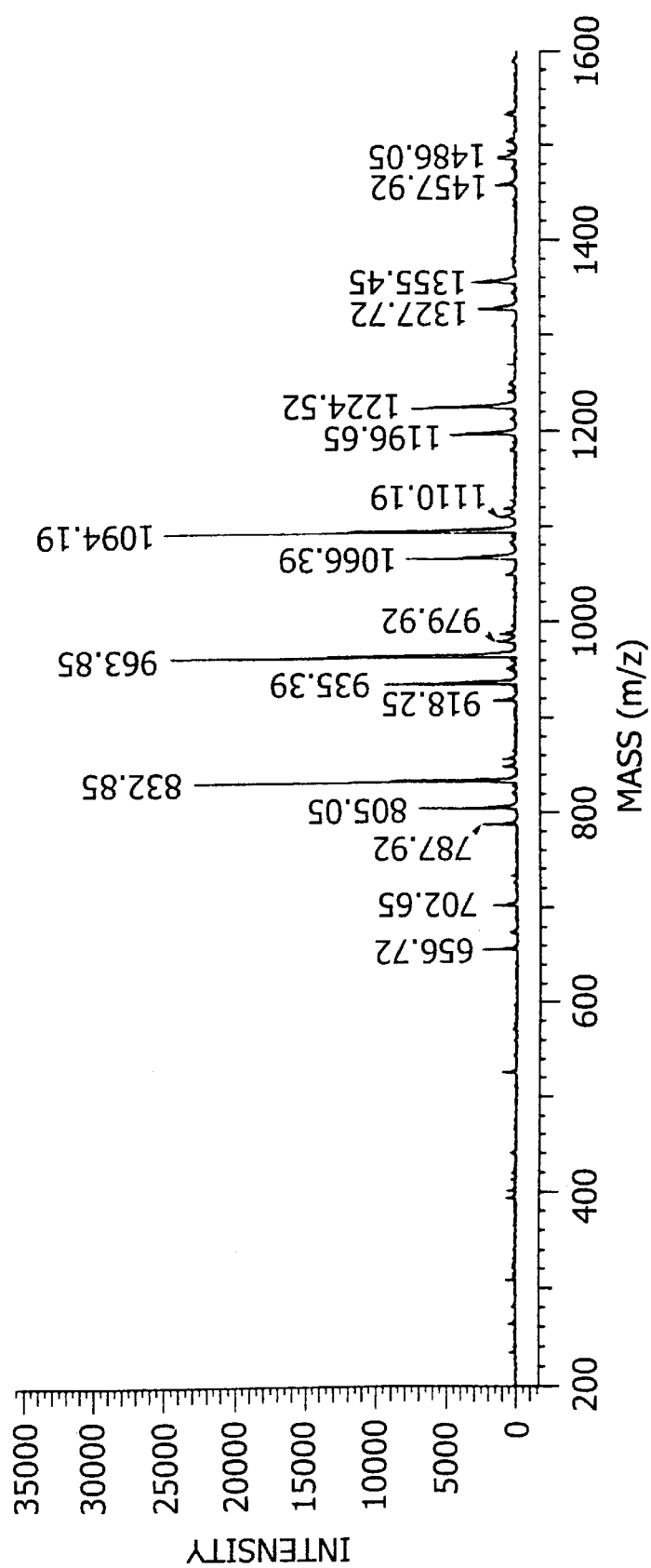
FIG. 28A is a positive ion ESI-MS spectra of HMBA-methionine co-oligomers synthesized with HMBA methyl ester and methionine ethyl ester.

Synthesis of MHBA-(Met)n Co-oligomers with MHBA-methyl ester and Met-ethyl ester ESI-MS Results Further experiments were conducted to confirm that MHBA is attached at the N-terminal of the oligomers chain. In one such experiment methyl ester of MHBA and ethyl ester of methionine were prepared. Equivimolar amounts of mixed esters were subjected to papain mediated oligomerization at pH 5.5 with the procedure outlined in Example 1. The product was washed with water until it was free of monomers. The product was then freeze-dried, dissolved in DMSO and introduced in the MS through an ESI interface. The positive and negative ion spectra obtain for the mixed oligomers are shown in FIG. 28.

The positive ion spectra (FIG. 28A) of shows two series of ions that are 28 mass units apart. One series containing ions m/z 674, 805, 936, 1067, 1198 and 1229 correspond to $((Met)_n+H^+)$ ions. The other series of ions which occur at m/z 702, 833, 964, 1095, 1226 and 1357 correspond to $((Met)n\text{-}OET) +H^+$ions. Ions in both series are 131 mass units or one methionine residue ($C_5H_9NOS$) apart. In both series, the value of n lies between 4–10.

Incorporation of MHBA at the C-terminal end of the polymethionine chain should have resulted in a series of ions corresponding to $((Met)n\text{-}MHBA\text{-}OCH_3)+H^+$ions. Such ions, if formed, would appear at m/z 688, 819, 958, 1081, 1212 and 1343. However, none of the peaks of this series were observed in the spectra. Similar results were obtained in the case of the negative ions (FIG. 28B). The absence of the methyl group provides indirect evidence that MHBA is incorporated at the N-terminal end. It should be pointed out that dominant ions obtained in negative ion mode were adduct ions and contained a dimethyl sulfone moiety.

EXAMPLE 6

Sonic Spray—MS-MS Results

The polymethionine and MHBA-polymethionine prepared from Met-ethyl ester and MHBA-ethyl ester were also subjected to MS-MS experiments. The freeze-dried precipitates were dissolved in DMSO ($2 \mu g/\mu l$) and the solution was introduced into the mass spectrometer with the sonic spray interface at the rate of 1 mL/hr. The solution was mixed with 1:1 acetonitrile:water mixture containing 0.1% acetic acid. The total fluid volume entering the SSI-MS was maintained at 0.2 mL min.$^{-1}$ The parent ion and spectra obtained with the system are shown in FIG. 29.

Ions of (Met)n-O Et +H$^+$corresponding to methionine hexamer, heptamer, octamer and nanomer were observed at m/z 833, 964, 1095 and 1225 amu respectively. For MS-MS experiment the ion at m/z 833 was excited with an auxiliary Vrf and subjected to collision induced dissociation. The daughter spectrum of $(Met)_6$-EE (SEQ ID NO: 3) is shown in FIG. 30. The prominent fragment ion was observed at m/z 657, this ion results from the cleavage of the amide bond resulting in the loss of Met-O Et ($C_7H_{14}NO_2S$) moiety from the C-terminal end. Similar results were obtained with molecular ions resulting from MHBA-$(Met)_n^-$. Daughter ions resulting from the loss of MHBA-O Methyl ($C_6H_{12}NO_2S$) moiety were not observed, indicating the absence of MHBA-O Methyl at the C-terminal end.

EXAMPLE 7

Papain Catalyzed Synthesis of MHBA-Tyrosine Co-oligomers

The success achieved in the papain catalyzed synthesis of methionine and MHBA oligomers led us to explore the synthesis of oligomers and co-oligomers of other hydrophobic amino acids. Candidate amino acids were tyrosine, tryptophan, leucine and phenyl alanine.

Synthesis of tyrosine oligomers and MHBA-tyrosine co-oligomers was initiated with tyrosine ethyl ester (Tyr- OMe) and MHBA ethyl ester as the monomer substrate. The overall synthesis and purification approach was similar to the one used for methionine and MHBA-methionine described in Example 1.

TABLE 4

Reaction Mixtures Used for Tyrosine and HMB-Tyrosine Oligomerization

| Components | MW | Moles | Wt |
|---|---|---|---|
| AA-ester | | | 3 g |
| L-Cys.HCl.H$_2$O | 175.6 | 100 mM | 0.1756 g |
| EDTA (anhyd) | 292.0 | 10 mM | 0.0292 g |
| Na Citrate | 294.1 | 1M | 2.941 |
| Papain | 21428D | 7*10$^{-5}$M | 15 mg |
| Volume | | | 10 ml |
| pH | | | 5.5 |

Dissolve the Tyr-OMe (equal amounts (wt %) in the case of HMB-OEt and Tyr-OMe) in 9.5 ml of 1M citrate buffer. Add EDTA and L-Cysteine. Set the of the reaction mixture pH to 5.5 and add 0.5 ml of papain suspension.

After incubation in a shaker for 24hrs, denature the enzyme by heating the broth to 80° C. for 10 min. Cool to room temperature.

Filter the broth and collect the precipitate—(or centrifuge the precipitate).

Dissolve the oligomers in DMSO and separate them from the monomers which are relatively insoluble in the solvent.

Evaporate the solvent and wash the precipitate with water, followed by freeze drying to obtain the dry oligomers.

Figure 31B:
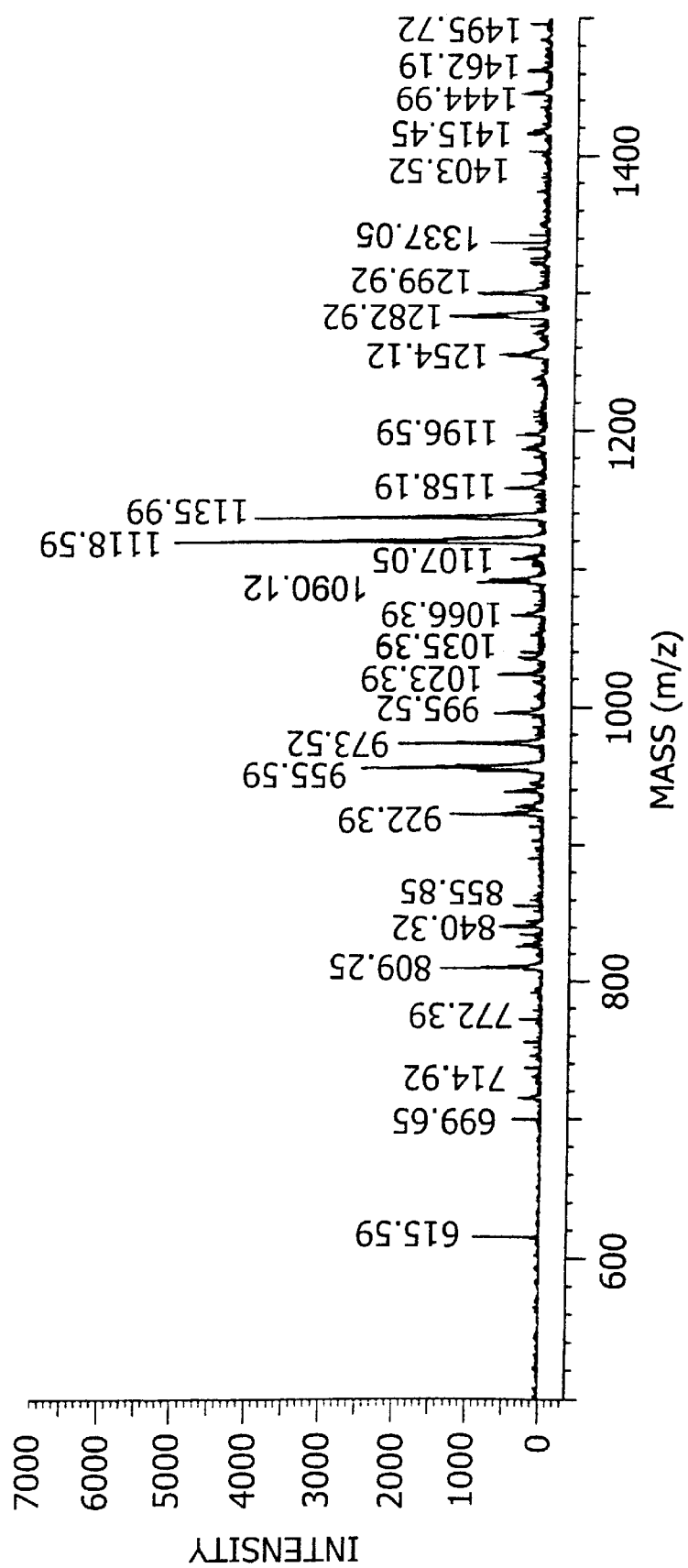
FIG. 31B is a negative ion ESI-MS spectra of tyrosine (Tyr)n oligomers wherein n is the number of tyrosine residues in the oligomers.

The reaction rate similar to those obtained with methionine were achieved. Approximate oligomer yield was 70–80%. The freeze-dried oligomers precipitates were solubilized in DMSO. The solution concentration was brought to approximately 2 μg/μl. The solution was mixed with 1:1 acetonitrile:water mixture containing 0.1% acetic acid. The total fluid volume entering the ESI-MS was maintained at 0.2 mL min.$^{-1}$ The positive mass spectrum of the tyrosine oligomers is shown in FIG. 31.

Two sets of prominent ions appeared in the Tyr oligomers spectra. One series of ions appeared at m/z 834, 997, 1160 and 1323, while the other series of ions were found at m/z 862, 1025, 1188 and 1351. The ions in the first series represent (Tyr)n+H$^+$, while the ions in the second series represent (Tyr)n-OEt+H$^+$. The ions in the two series are 28 amu (C$_2$H$_4$) apart indicating the presence of O-Et at the C-terminal end in one series. Ions within the two series are separated by 163 amu, corresponding to the repeating unit of the Tyr residue (C$_9$H$_9$NO$_2$). Thus, the protonated ion at 862 most probably represents the tyrosine oligomers with five residues and a ethyl ester attached to the C-terminal end. Similarly, the ion at m/z 1025 most likely results from the (Tyr)$_6$_OEt+H$^+$. The ion at m/z 997 results from (Tyr)$_6$+H$^+$. The presence of oligomers with 5 to 8 Tyr residues is clearly evident, furthermore, the (Tyr)$_6$ was found to be the most prominent oligomer.

The positive ion mass spectrum of MHBA-tyrosine co-oligomer is shown in FIG. 32A. The dominant ions in this spectrum were the same ions observed in the positive ion spectrum of polytyrosines, FIG. 31A. However, additional ions appeared at m/z 831, 994 and 1157. These ions appear at a mass difference of 133, suggesting the presence of a MHBA residue in the oligomer. The peak at m/z 831 most probably represents the co-oligomer with one MHBA residue and 4 tyrosine residues with the ethyl ester moiety (MHBA-(Tyr)$_4$ OEt+H$^+$). Similarly, the residues at m/z 994 and 1157 represent co-oligomers with one MHBA residue and 6 and 7 tyrosine residues respectively. The weak intensity of these ions in part relate to lower proton affinity of the hydroxyl group.

EXAMPLE 8

Papain Catalyzed Synthesis of MHBA-Leucine Co-oligomers

The papain-catalyzed synthesis of leucine and MHBA co-oligomers was also explored. Synthesis of leucine oligomers and MHBA-leucine co-oligomers was initiated with leucine ethyl ester and MHBA ethyl ester as the substrates. The overall synthesis and purification approach was similar to the one used in the case of methionine and MHBA-methionine. Reaction rates similar to those obtained with methionine and tyrosine were achieved. Approximate oligomer yield was 58%. The freeze-dried oligomers precipitates were solubilized in DMSO. The solution concentration was brought to approximately 2 μg/μl. The solution was mixed with 1:1 acetonitrile:water mixture containing 0.1% acetic acid. The total fluid volume entering the ESI-MS was maintained at 0.2 mL min.$^{-1}$ The positive mass spectrum of the leucine oligomers is shown in FIG. 33A.

Four sets of ions appeared in the positive ion spectra of (Leu)$_n$. One set of ions corresponding to (Leu)$_n$+H$^+$appeared at m/z 698, 811 and 924. The other set of ions appeared at m/z 720, 833 and 947 and correspond to (Leu)$_n$+Na$^+$. Another set of ions appeared at m/z 747, 860 and 973 which correspond to (Leu)$_6$-OEt +Na$^+$, (Leu)$_7$-OEt+Na$^+$and (Leu)$_8$-OEt+Na$^+$. However, the two prominent ions in the spectra appear to be (Leu)$_6$-OEt Na+Na$^+$and (Leu)$_7$-OEt Na +Na$^+$. These results clearly show that the dominant oligomers are (Leu)$_5$, (Leu)$_6$, (Leu)$_7$ and (Leu)$_8$. The mass difference of 28 amu (C$_2$H$_4$) indicates the presence of O-Et at the C-terminal. Ions within the two series are separated by 113 amu, corresponding to the repeating unit of the Leu residue (C$_6$H$_{11}$NO). Thus, the doubly sodiated (Na$_2$) ion at m/z 770 and 883 most probably represents leucine oligomers with six and seven residues and a ethyl ester attached to the C-terminal end.

The negative ion mass spectrum of the leucine oligomers is shown in FIG. 33B. The overall appearance of the spectra is similar to that of the positive ion spectra. The two dominant ion in this spectra correspond to (Leu)$_6$-OEt +Na and (Leu)$_7$-OEt +Na.

The positive and the negative ion spectra of MHBA-Leu co-oligomers are shown in FIG. 34. As expected, the positive spectra contained all of the dominant ions observed in the positive ion ESI-MS spectra of (Leu)$_n$. However, three additional strong ions at m/z 740, 853 and 866 were also found. These masses correspond to sodiated co-oligomers MHBA-(Leu)$_5$+Na$^+$, MHBA-(Leu)$_6$+Na$^+$and MHBA-(Leu)$_7$+Na$^+$respectively. Thus, formation of co-oligomers with one MHBA residue with five to seven leucine residues is clearly evident.

EXAMPLE 9

Papain Catalyzed Synthesis of MHBA-Phenylalanine Co-oligomers

Papain catalyzed synthesis of phenylalanine and MHBA co-oligomers was also conducted. Synthesis of phenylalanine oligomers and MHBA-phenylalanine co-oligomers was initiated with phenylalanine ethyl ester and MHBA ethyl ester as the substrates. The overall synthesis and purification approach was similar to the one used in the case of methionine and MHBA-methionine in Example 1. The oligomerization reaction did not proceed when phenylalanine was the only substrate present in the reaction mixture. The reaction did proceed when MHBA-ethyl ester was added to the reaction mixture. Reaction rates similar to those with methionine and tyrosine were achieved. Approximate oligomer yield was 90%. The freeze-dried oligomers precipitates were solubilized in DMSO. The solution concentration was brought to approximately 2 $\mu g/\mu l$. The solution was mixed with 1:1 acetonitrile:water mixture containing 0.1% acetic acid. The total fluid volume entering the ESI-MS was maintained at 0.2 mL min.$^{-1}$ As stated earlier, phenylalanine homo-oligomers were not formed.

The ESI-MS results of MHBA-PheMHBA co-oligomerization reaction are given in FIG. 35. The positive ion spectra of MHBA-Phe co-oligomers are depicted in FIG. 35A, while the negative ion spectra are depicted in FIG. 35B. The positive spectra of the co-oligomers yielded three ion peaks at m/z 790, 937 and 1084. The mass difference between these ions is 147 or a difference of one phenylalanine residue ($C_6H_6NO=147$). The m/z values of the ions most likely correspond to MHBA-(Phe)$_4$-OEt+Na$^+$, MHBA-(Phe)$_5$-OEt+Na$^+$ and MHBA-(Phe)$_6$-OEt +Na$^+$. Thus, formation of co-oligomers with one MHBA residue and four to six Phe residues is clearly evident.

EXAMPLE 10

Optimization of Papain Catalyzed Synthesis of (Lys)n Oligomers and MHBA-(Lys)n Co-oligomers Experiments were conducted to optimize the reactions conditions for papain catalyzed synthesis of lysine oligomers and lysine co-oligomers with MHBA. Reactions were carried out in two systems. The first system consisted of an aqueous phase and an immiscible organic phase, while the second system consisted of an aqueous phase sandwiched between two mutually immiscible organic phases (a three phase system).

A. Two Phase Reaction System

The two-phase reaction system consisted of a small amount of polar phase and a larger amount of a immiscible non-polar phase. The polar phase was comprised of water, isopropyl amino ethyl and mercaptoethanol. This phase also contained the amino acid ester substrate and papain. During optimization parameters such as the volume ratio of the aqueous and the non-aqueous phase, composition of additives, concentrations of the additives, concentrations of the substrates, and the concentration of the enzyme were varied. The effect of these parameters on the degree of oligomerization and yield were monitored. The results of the experiments are summarized below:

A.1 Aqueous:Organic Phase Ratio

Figure 36:
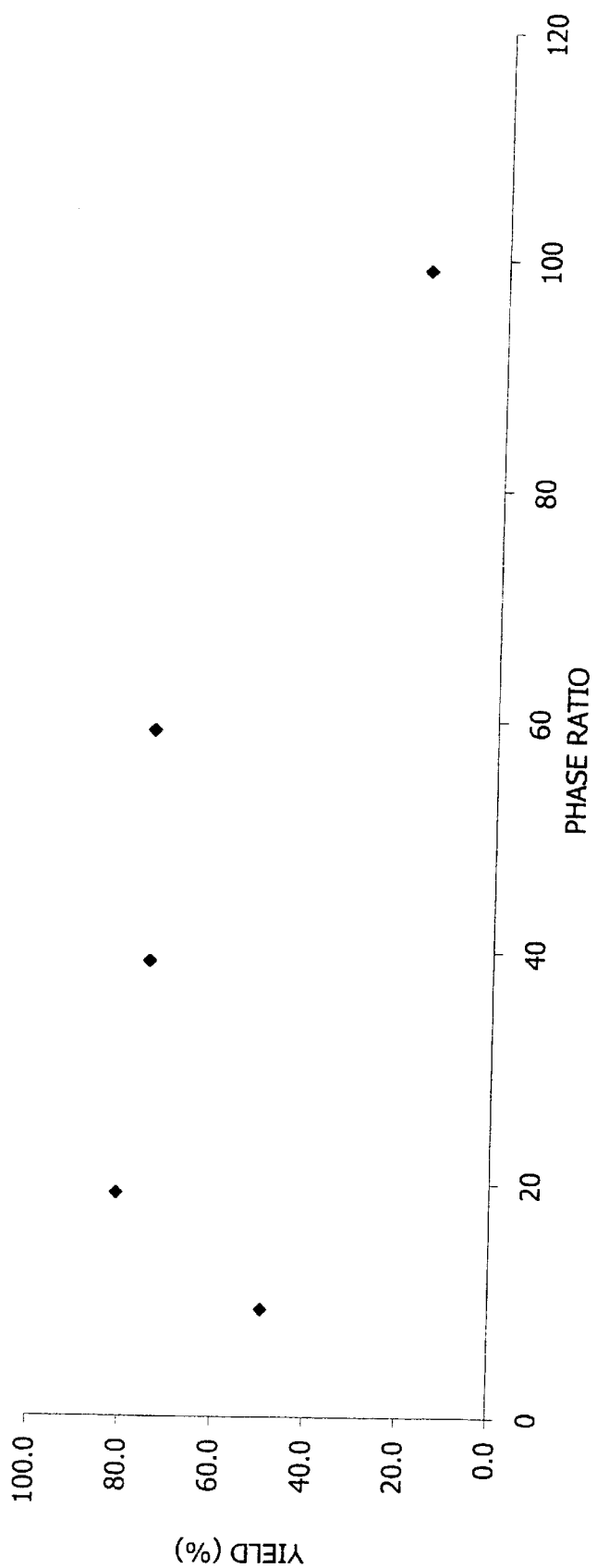
FIG. 36 is a graph of the effect of Aqueous:Non-Aqueous ratios on $(Lys)_n$ oligomer yield wherein n is the number of lysine residues in the oligomers in a two-phase system.

To optimize the volume ratio of the aqueous and organic phases (toluene), the oligomer yields and degree of oligomerization were monitored over phase ratios ranging from 1:9–1:99, the reaction was allowed to proceed for 24 hours. Oligomer were recovered from the aqueous phase and analyzed. Results of these experiments are shown in FIG. 36.

Figure 37:
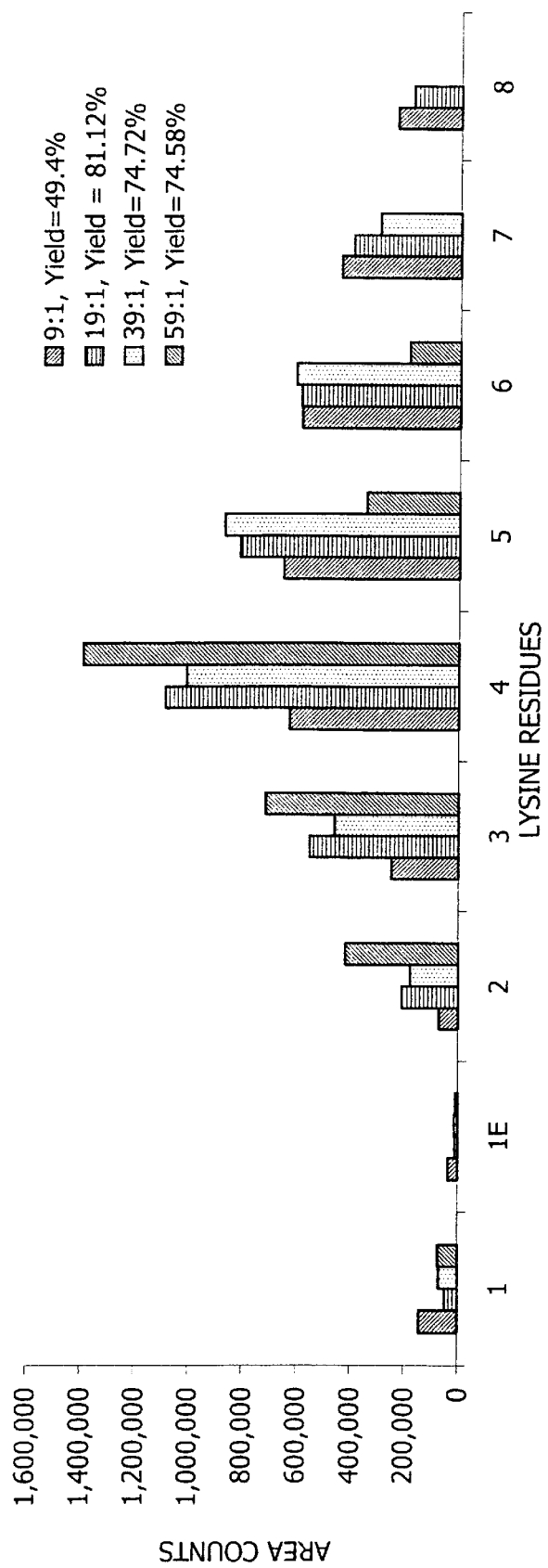
FIG. 37 is a bar graph of the effect of volumetric ratios on the degree of $(Lys)_n$ oligomer yield in a two-phase reaction system wherein n is the number of lysine residues in the oligomers.

The results indicate that the yields dropped at ratios below 19 and the higher ratios did not lead to an appreciable change in total yield. The results also showed that while the total yield did not change at higher organic solvent volumes, the degree of oligomerization was affected. Higher toluene volume led to a decrease in the degree of oligomerization. The length of oligomers chains at phase ratio 1:19 extended up to nine lysine residues (Lys)$_9$ (SEQ ID NO: 15), whereas at phase ratio 1:39, the largest oligomers contained only six lysine residues (Lys)$_6$ (SEQ ID NO: 16), FIG. 37. In light of these results and to conserving organic solvent, all subsequent experiments were carried out at phase ratio 1:19.

A.2 Optimization of Additive Concentration

Figure 38:
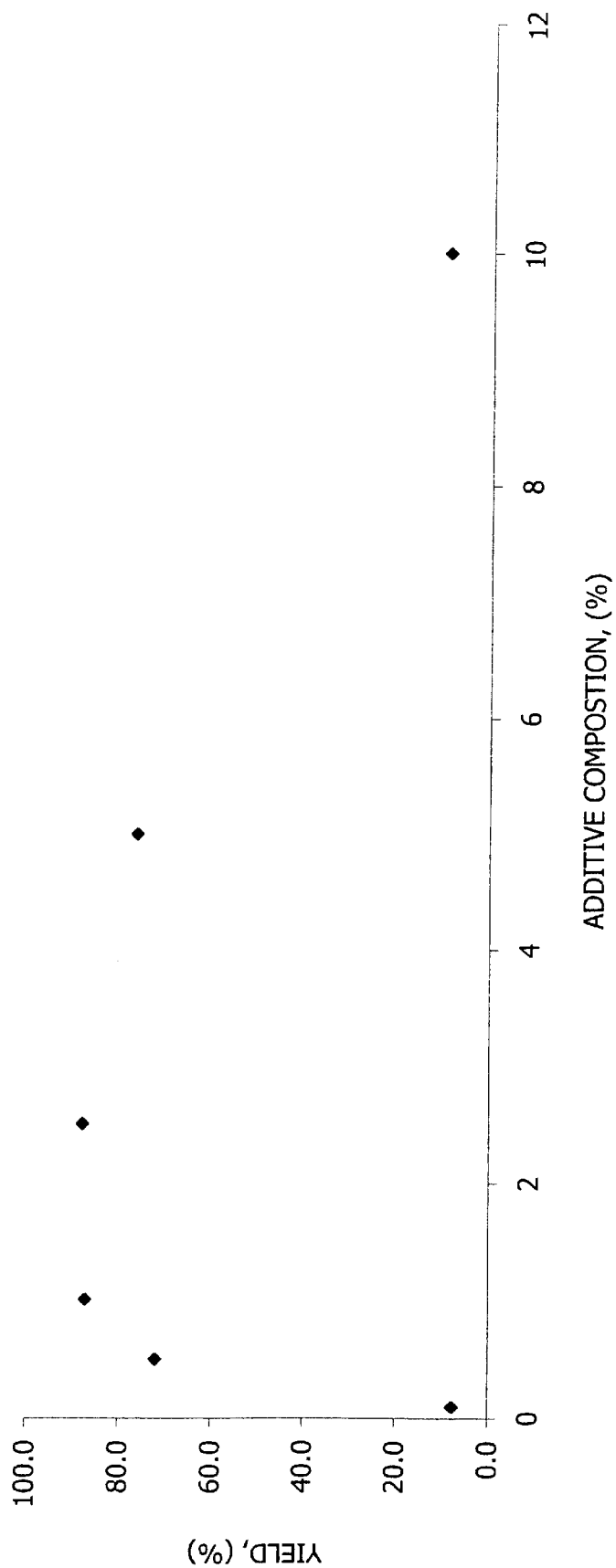
FIG. 38 is a graph of the effect of additive concentrations on $(Lys)_n$ oligomer yield wherein n is the number of lysine residues in the oligomers.

The effect of the concentration of additives (mercaptoethanol and isopropyl ethyl amine) on yield and degree of oligomerization was also examined. These additives act as antioxidants and prevent oxidation of cysteine moiety in the enzyme. The reaction was carried out for 24 hours. Oligomers were recovered from the aqueous phase and analyzed. Results showed that concentration of additives had a marked effect on the total yield and the degree of oligomerization. The total yield increased with an increase in additive concentration from 0.1–2%. However, a pronounced decrease in total oligomers yield was observed when the additive concentration was increased above 5%. A 2% additive concentration was found to the optimum under conditions used in these experiments. The total oligomers yield at this additive concentration was approximately 87%, FIG. 38.

Figure 39:
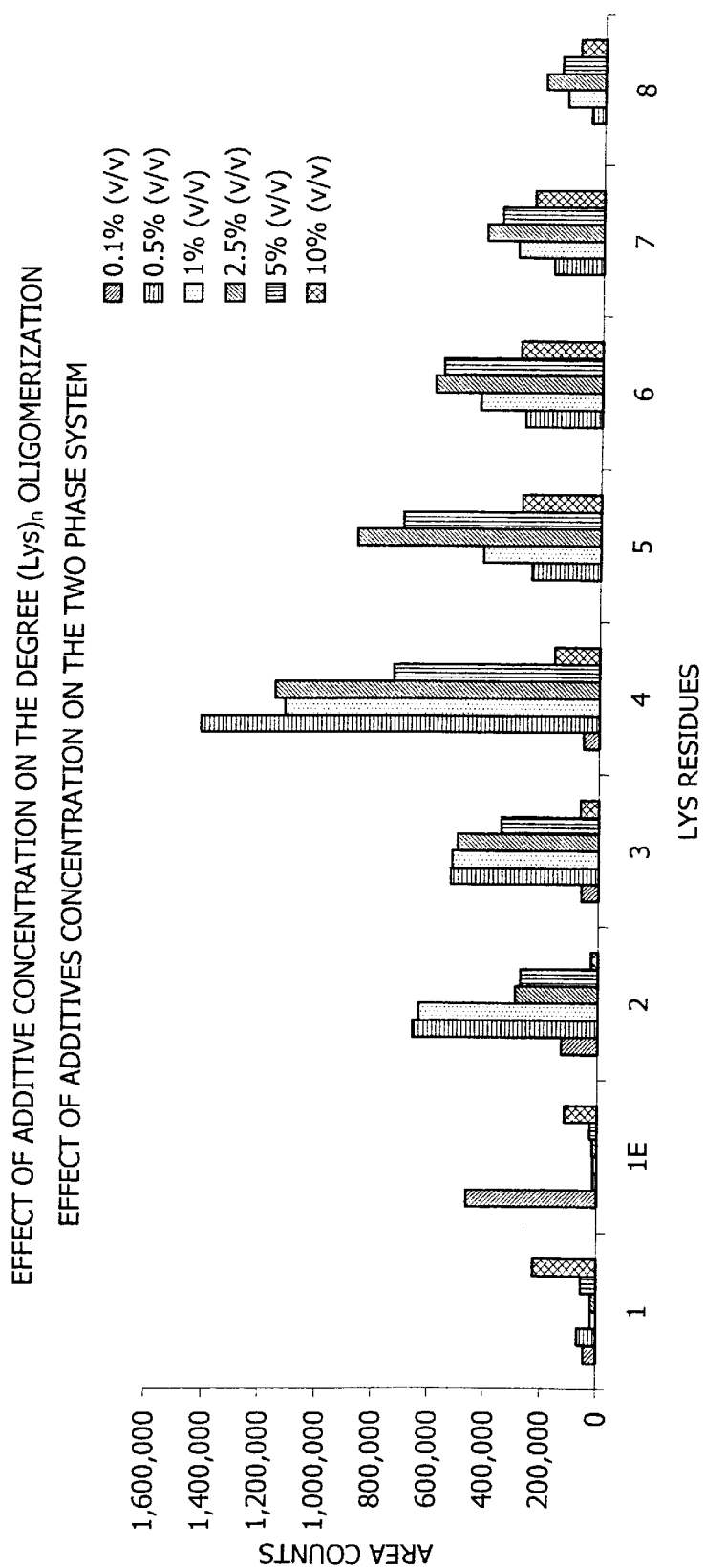
FIG. 39 is a bar graph of the effect of additive concentrations on the degree of $(Lys)_n$ oligomerization wherein n is the number of lysine residues in the oligomers.

The degree of oligomerization was found to increase with an increase in additive concentration up to 2%, still higher concentrations did not lead an appreciable change in the oligomers distribution, FIG. 39.

A.3 Optimization of Substrate Concentration

Figure 40:
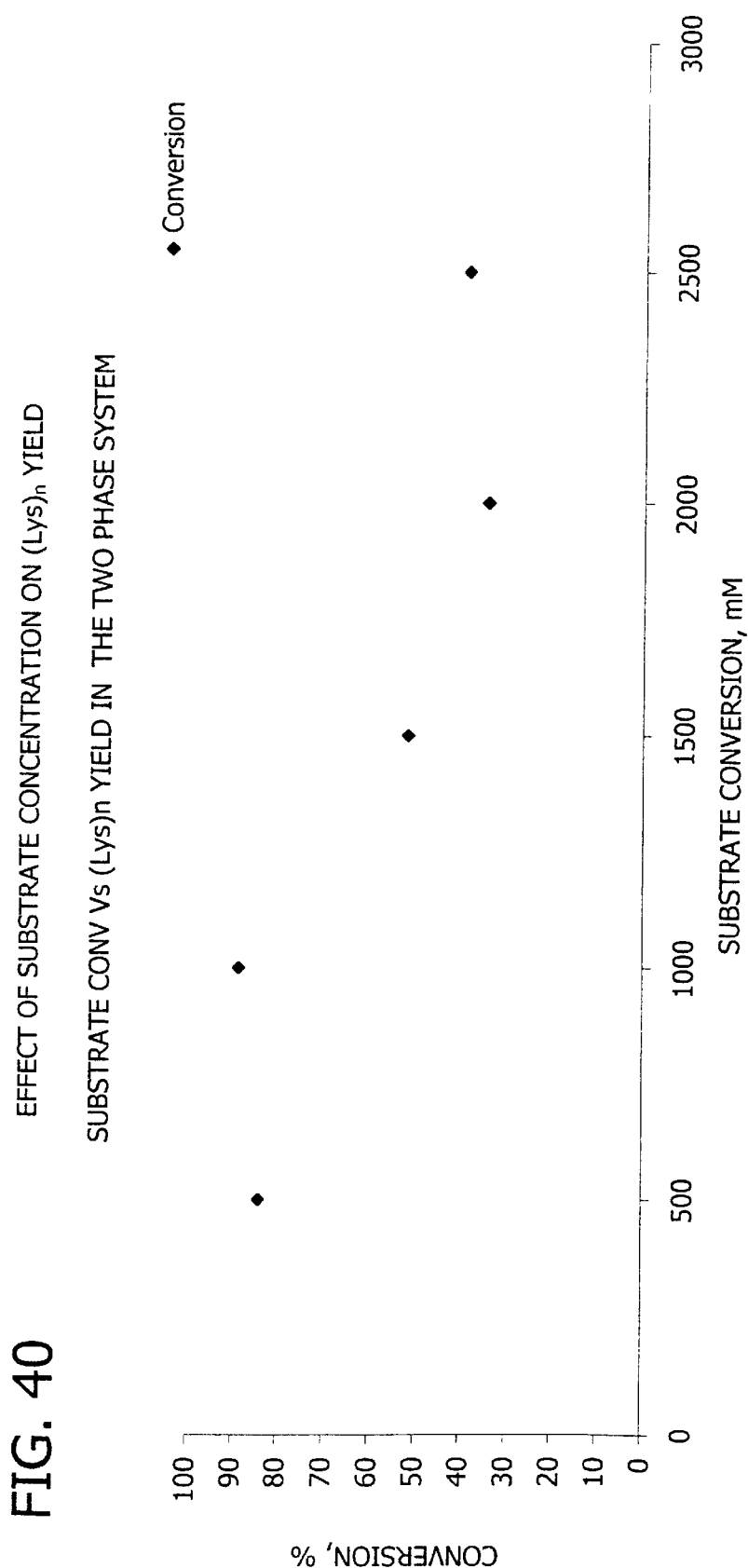
FIG. 40 is a graph of the effect of substrate concentrations on $(Lys)_n$ oligomer yield wherein n is the number of lysine residues in the oligomers.

A series of experiments were carried to optimize the substrate (lysine ethyl ester) concentration at a fixed enzyme activity. The concentration of substrate was varied five folds, from 500 mM to 2,500 mM, while the enzyme concentration was held constant at 1.21 mM. Oligomerization reactions were allowed to proceed for 24 hours after which the enzyme was deactivated and oligomers recovered from the aqueous phase and analyzed. A plot of the percent oligomers yield (total oligomers mass/total substrate mass×100) vs the substrate mass is shown in FIG. 40.

Figure 41:
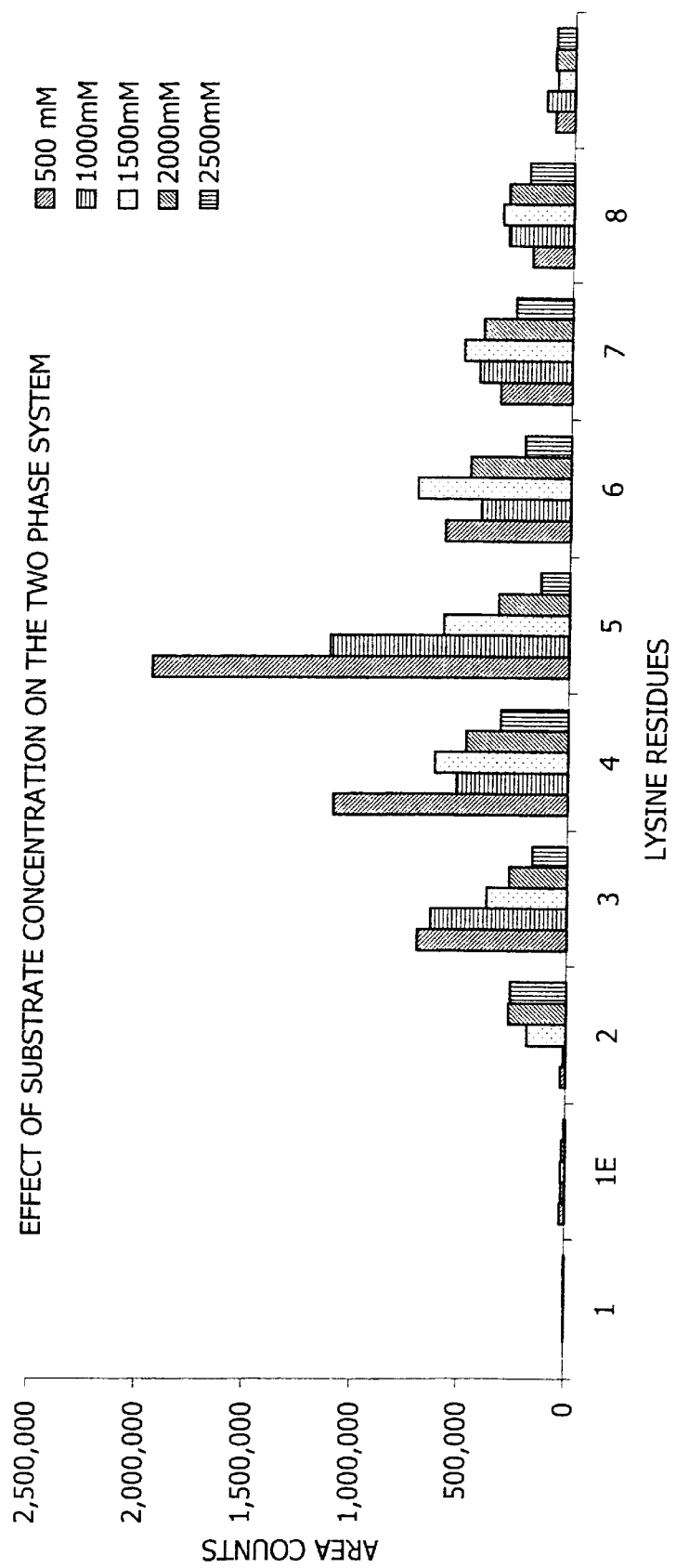
FIG. 41 is a bar graph of the distribution of lysine oligomers formed in reaction mixtures with varied substrate concentrations.

The results show that the highest conversion efficiency was achieved at a substrate concentration of 1000 mM. A noticeable drop in conversion efficiency above this concentration was clearly evident. The degree of oligomerization was also affected by the substrate concentration. In general, higher concentration led to the formation of oligomers with higher lysine residues (e.g., the most abundant oligomers at 500 mM lysine ethyl ester was (Lys)$_4$ (SEQ ID NO: 17) and the yield of higher homlogs was quite low). The most abundant oligomer was (Lys)$_5$ (SEQ ID NO: 18). In addition, concentrations of higher homologs (Lys)$_6$ (SEQ ID NO: 16), (Lys)$_7$ (SEQ ID NO: 19) and (Lys)$_8$ (SEQ ID NO: 20) were noticeably higher, FIG. 41.

A.4 Optimization of Incubation Period

Figure 42:
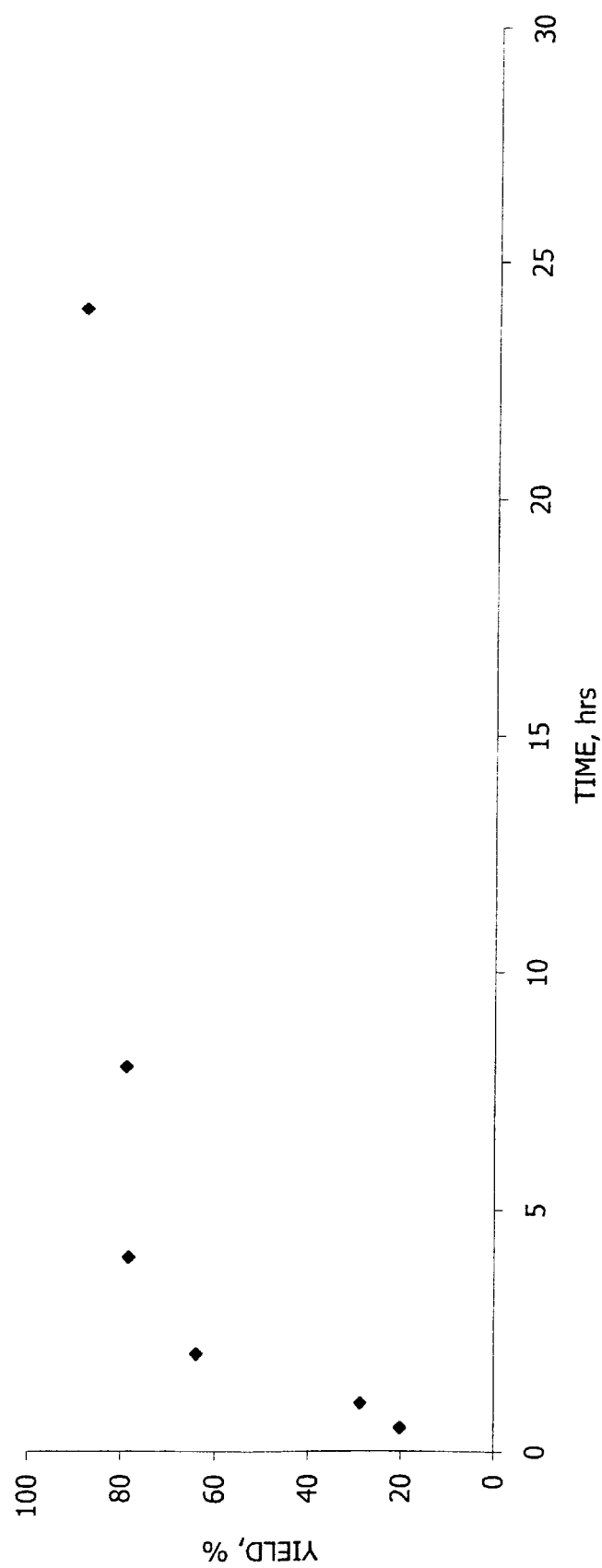
FIG. 42 is a graph of the effect of incubation time on total lysine oligomer yield.

Another set of experiments was carried out to determine an optimum incubation period for oligomerization of lysine. The reaction were conducted with 1:19 phase ratio, 1 M substrate concentration and 1% additive concentration. The reaction was allowed to continue for time periods ranging between 30 minutes to 24 hours. After each time period, the reaction was brought to halt by deactivating the enzyme. The oligomers were recovered from the aqueous phase and analyzed. The total oligomers yield obtained at various time periods is shown FIG. 42.

Figure 43:
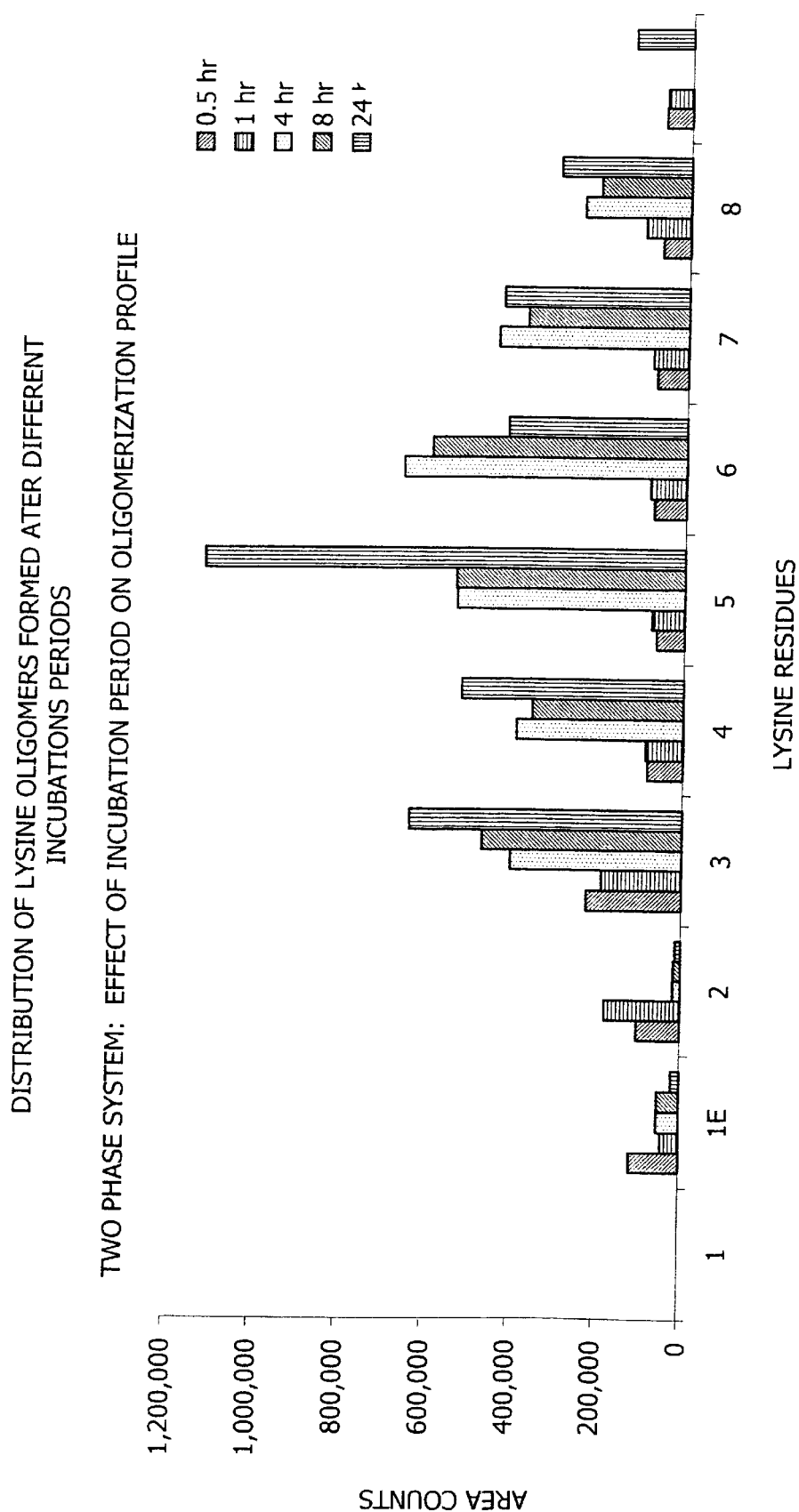
FIG. 43 is a bar graph of the distribution of lysine oligomers formed after different incubation time periods.

The graph shows that the reaction is nearly complete within the first four hours and only a marginal increase in yield is obtained at longer incubation periods. Analyses of oligomers obtained after different time periods showed that the time periods shorter than 4 hours yield an even distribution of oligomers from $(Lys)_2$ to $(Lys)_8$ (SEQ ID NO: 20), while the longer periods yield higher concentrations of $(Lys)_4$ (SEQ ID NO: 17) to $(Lys)_6$ (SEQ ID NO: 16) oligomers, FIG. 43.

B. Three Phase System

The three-phase system consisted of an aqueous phase present in between two immiscible non-aqueous phases, one lighter than the aqueous phase and the other heavier than the aqueous phase. The heavier phase was comprised of decafluoropentane and the lighter phase was n-octane. Isopropyl ethyl amine and mercaptoethanol additives were added to the aqueous phase along with the lysine ethyl ester (substrate) and papain (enzyme). The effects of parameters such as the relative volumes of aqueous to non-aqueous phases, the concentration of the additives, the substrate concentration and the enzyme activity on oligomers yield and degree of oligomerization were monitored through a set of experiments.

B 1. Optimization of Aqueous and Non-aqoueous Phase Ratio

Figure 44:
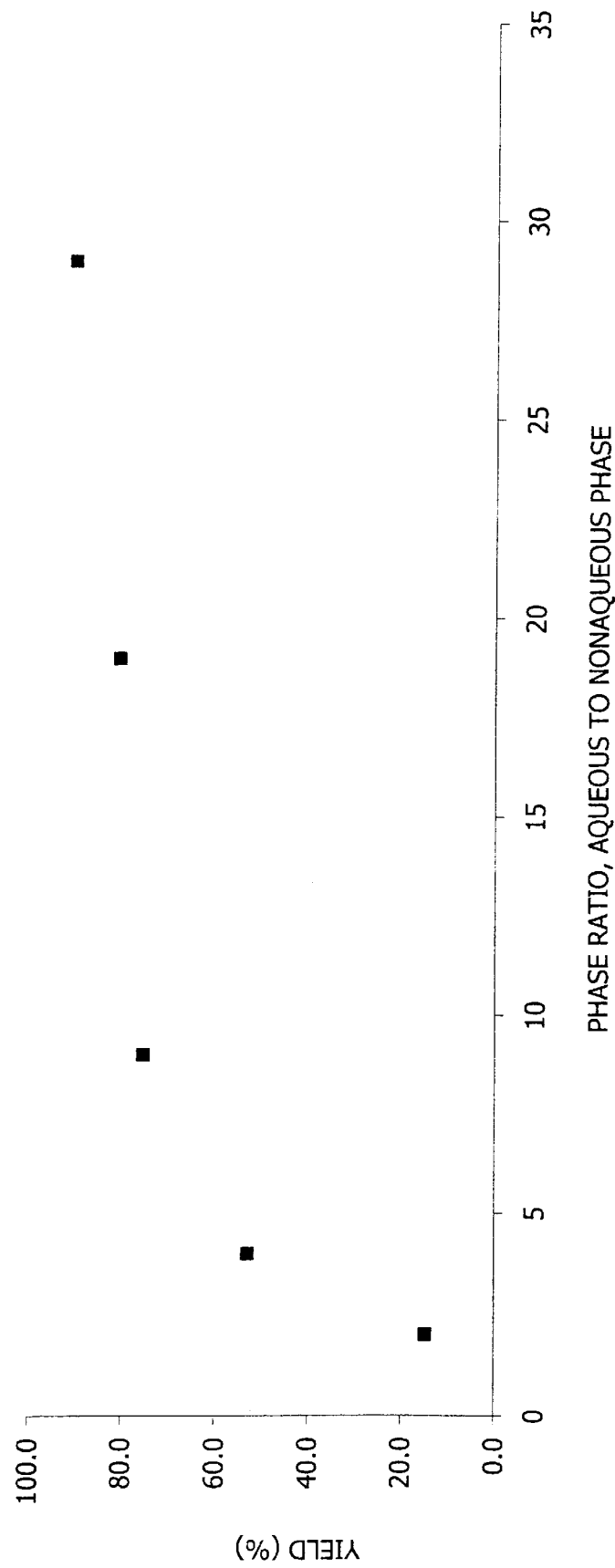
FIG. 44 is a graph of the effect of aqueous to non-aqueous solvent phase ratios on total lysine oligomer yield in a three-phase system.

The ratio of the non-aqueous phase volume to aqueous phase volume was varied by changing the volumes of the two organic solvents in equal proportion while holding the aqueous phase volume constant. Substrates, antioxidant additives and enzyme were added to the aqueous phase. The reactants and the enzyme were placed in a stirred reactor and allowed to incubate at 37° C. for 24 hours. The total oligomers yield was determined gravimetrically, while the degree of oligomerization was determined through RPLC analysis. Results of gravimetric determination are represented in FIG. 44.

Figure 45:
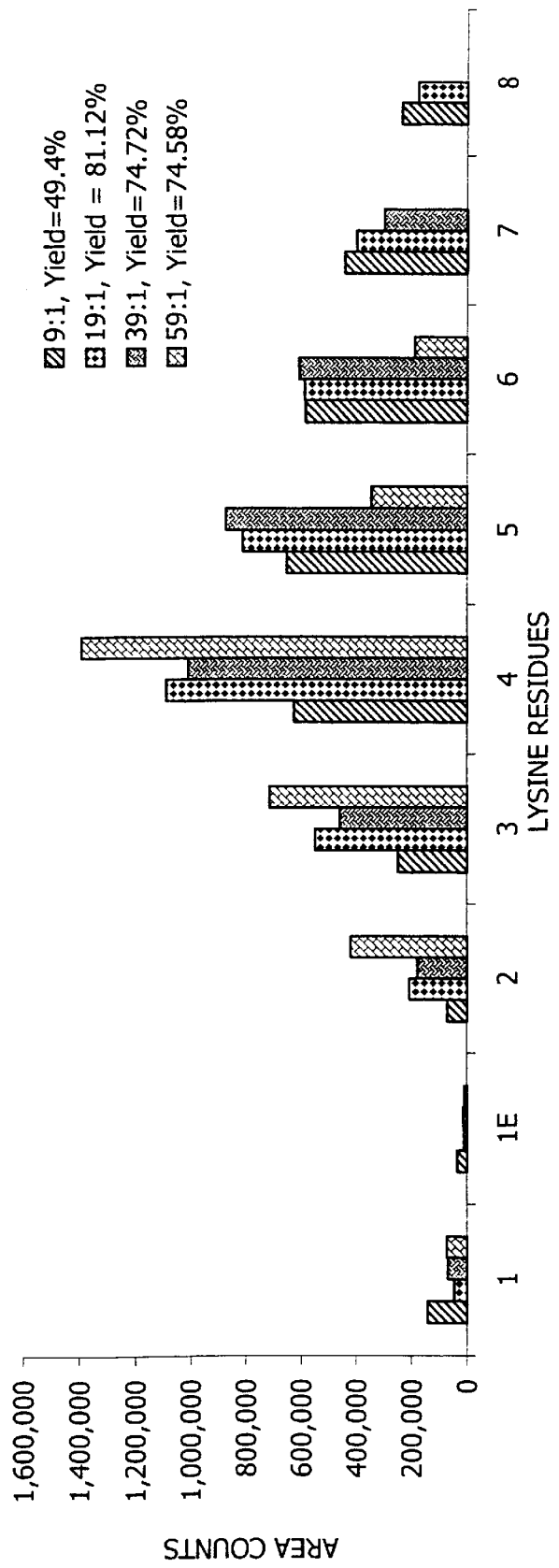
FIG. 45 is a bar graph of the distribution of lysine oligomers formed in reaction mixtures at various aqueous to non-aqueous solvent ratios.

The results show that the oligomer yield increased with an increase in total organic phase. However, the increase in yield was relatively small above an aqueous:organic ratio of 1:10. The effect of phase ratio on the degree of oligomerization is shown in FIG. 45. Results show that while the total yields are lower (approximately 15–50%) at the lower phase ratios, the degree of oligomerization is higher and oligomers with up to10 lysine residues can be readily obtained. At higher phase ratios, the total oligomers yields are significantly greater (e.g., up to approximately 85%). The degree of oligomerization was generally lower, however, as the predominant oligomers formed under these conditions contained three to five lysine residues.

B 2. Optimization of Additives Concentration

Figure 46:
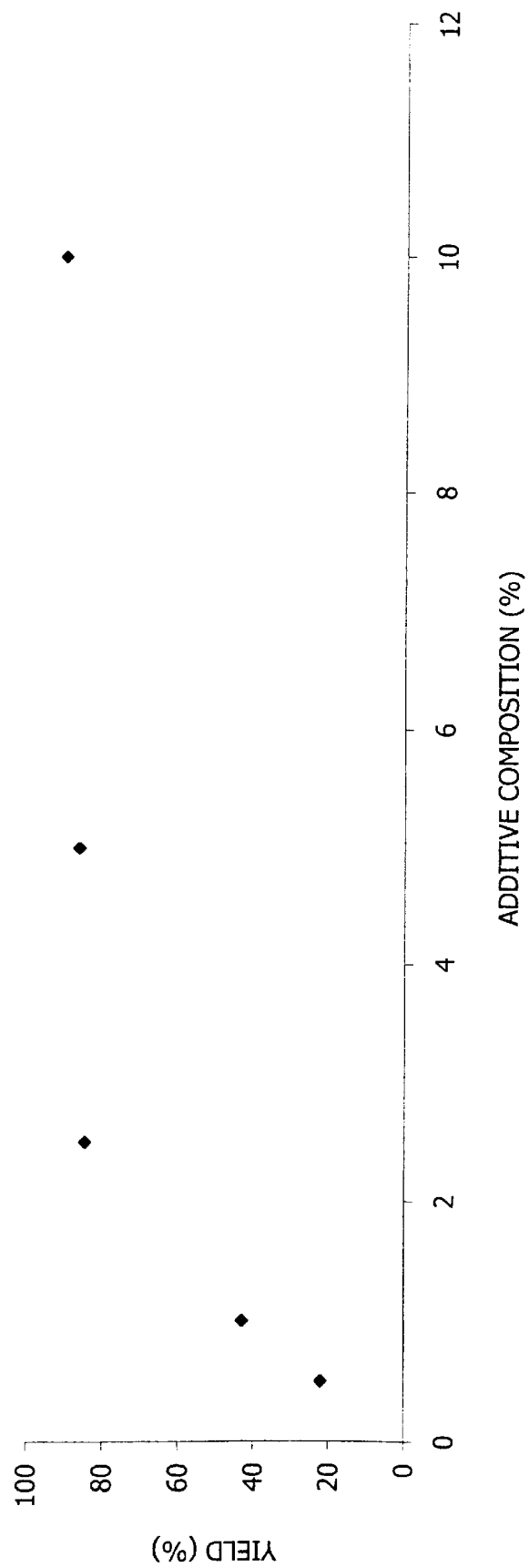
FIG. 46 is a graph of the effect of additive concentrations on the total lysine oligomers yield.
Figure 47:
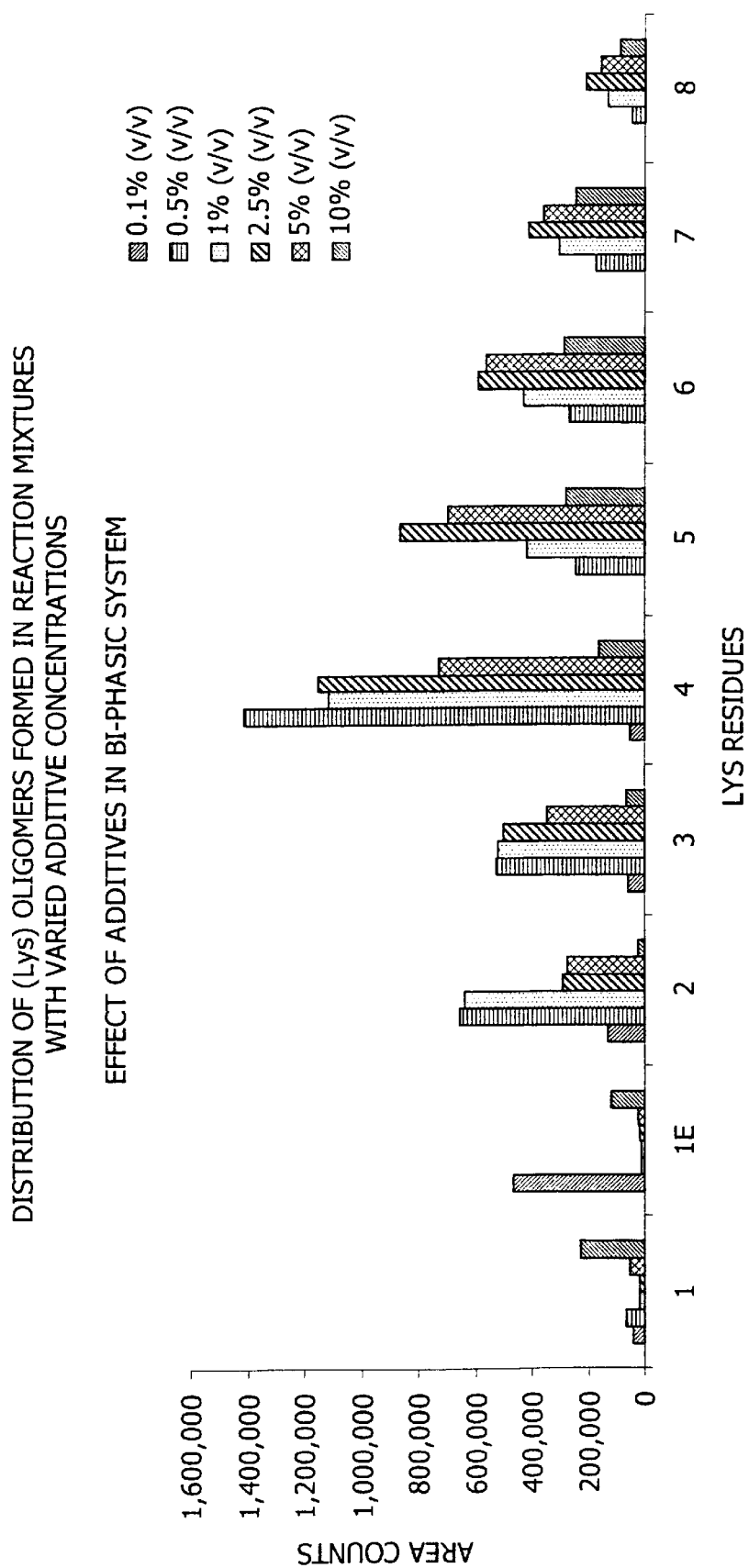
FIG. 47 is a bar graph of the distribution of lysine oligomers formed with varied additive concentrations in a 2-phase system.

The effect of the total additive concentration on the oligomers yield and degree of oligomerization was examined. At low additive concentrations (e.g., concentrations <1.5%), the overall oligomers yields were low (e.g., approximately 40%). An increase in additive concentration up to 2.5% led to an increase in the oligomers yield, however, concentration above this level did not lead to higher yields, FIG. 46. The concentration of the additives did not assert a pronounced effect on the distribution of lysine oligomers, FIG. 47.

B 3. Optimization of Incubation Period

Figure 48:
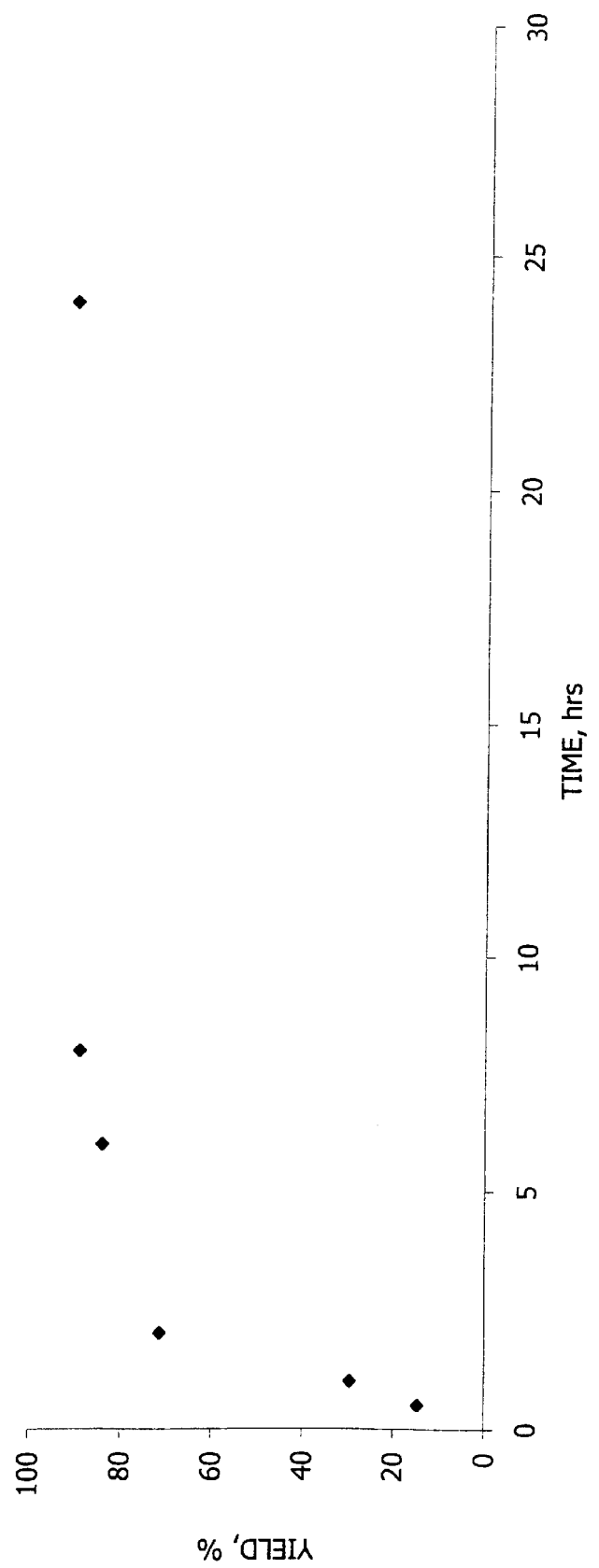
FIG. 48 is a graph of the total lysine oligomer yield formed after different incubation time periods in a 3-phase system.
Figure 49:
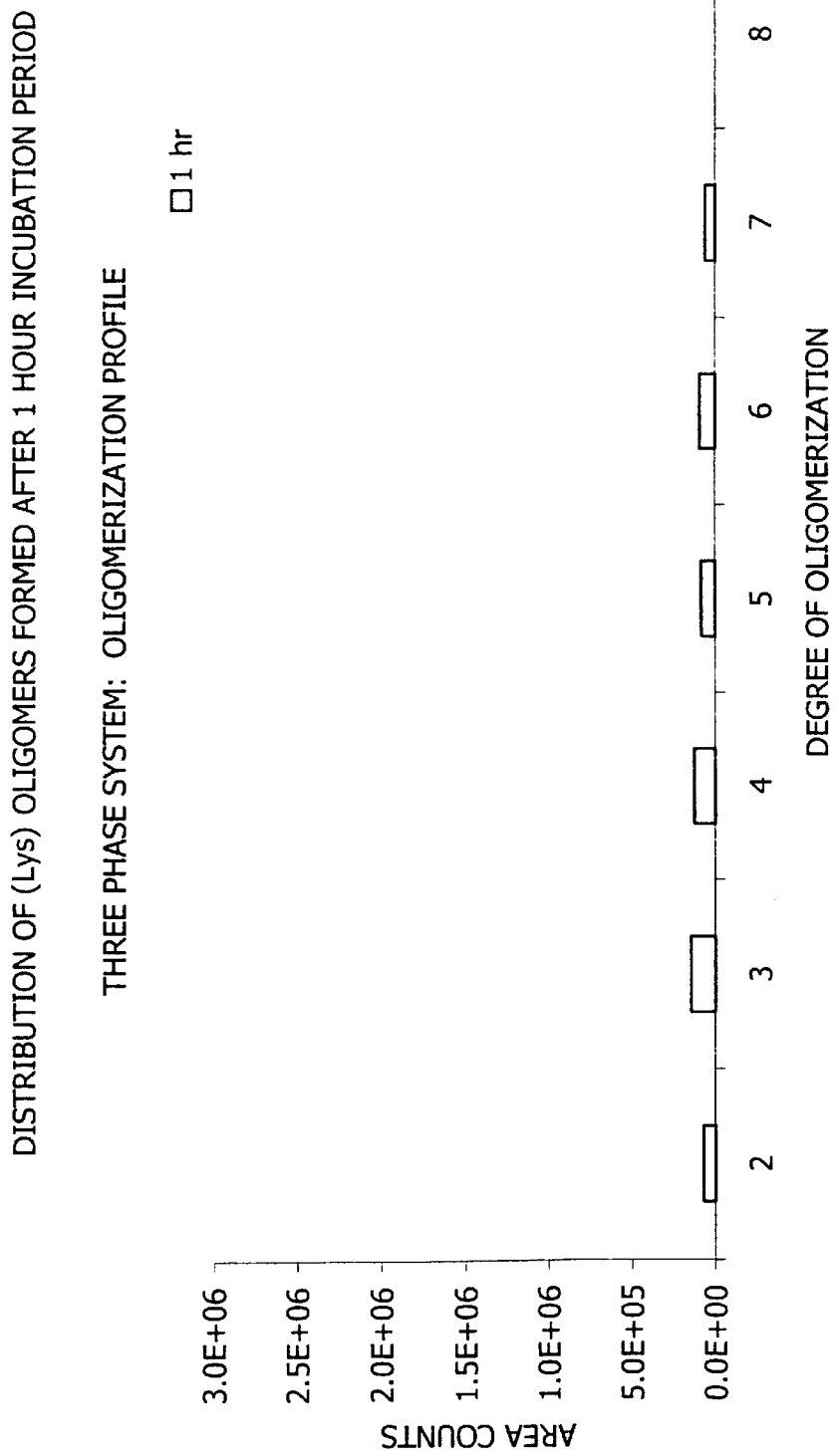
FIG. 49 is a bar graph of the distribution of lysine oligomers formed after a one hour incubation period in a 3-phase system.

The incubation period for the three-phase reaction system was examined through another set of experiments. The experiments were conducted with three phase reaction mixtures consisting of aqueous phase and total organic phases, the aqueous:organic phase ratio was set at 1:9. The additive concentrations were varied. The incubation periods were varied from 30 minutes to 30 hours. After each time period, total oligomer yield and degree of oligomerization were examined. Results are shown in FIG. 48. The results indicate that the reaction reaches completion in approximately six hours and nearly 90% of the initial substrate mass is converted into the oligomers. Longer incubation periods did not lead to higher yields.

Figure 50:
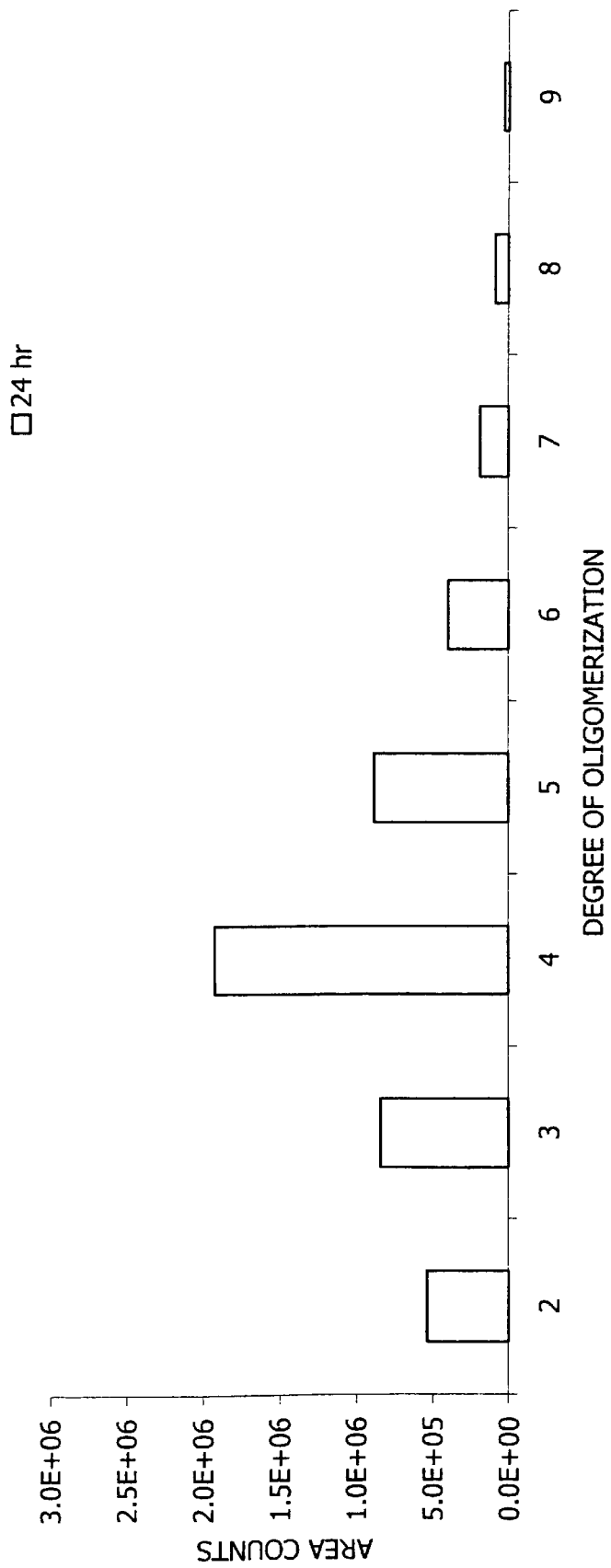
FIG. 50 is a bar graph of the distribution of lysine oligomers formed after a 24 hour incubation period in a 3-phase system.

RPLC results showed that the longer incubation periods favored oligomers with smaller lysine residues. The predominant residue after a 24 hour incubation period was found to be $(Lys)_4$ (SEQ ID NO: 17), FIG. 50.

The studies above demonstrate the effect of various parameters in the three phase and two-phase systems and can be used to tailor the reaction to produce the required residue range and composition.

As various changes could be made in the above compositions and processes without departing from the scope of the invention, it is intended that all matter contained in the above description be interpreted as illustrative and not in a limiting sense.

What is claimed is:

1. A composition comprising

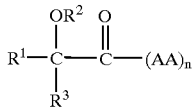

wherein

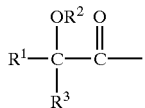

is the residue of an α-hydroxy acid analog of a naturally occurring α-amino acid, wherein $R^1$ is hydrogen, hydrocarbyl or substituted hydrocarbyl, $R^2$ is hydrogen, hydrocarbyl, substituted hydrocarbyl, or is another hydroxy protecting group selected from the group consisting of tert-butyldimethylsilyl (TBS), tert-butyldiphenylsilyl (TBPS), triethylsilyl (TES), trimethylsilyl (TMS), and triisopropylsilyl (TIPS), $R^3$ is hydrogen, hydrocarbyl or substituted hydrocarbyl, each AA is the residue of an α-amino acid selected from the group consisting of α-amino acids independently of any other α-amino acid residue, and n is at least 2, wherein said $R^2$ substituted hydrocarbyl moieties are hydrocarbyl moieties that are comprised of one or more substituted atoms other than carbon, wherein the substituted atoms are selected from the group consisting of oxygen, silicon, phosphorus, boron, sulfur, and halogen atoms.

2. The composition of claim 1 wherein $R^1$ is $CH_3SCH_2CH_2$—.

3. The composition of claim 2 wherein $R^2$ is H.

4. The composition of claim 1 wherein $R^2$ is H.

5. The composition of claim 1 wherein each AA is methionine.

6. The composition of claim 1 wherein each AA is selected from the group consisting of methionine and lysine.

7. The composition of claim 1 wherein n is at least 2 and no more than 10 and each AA is selected from the group consisting of methionine and lysine.

8. A process of providing an animal with its nutritional or pharmacological amino acid needs comprising providing the composition of claim 1 to the animal wherein the method of administration is selected from the group consisting of oral administration, eye spray, placement in ear, placement in nasal cavity, and injection.

9. The process of claim 8 wherein the composition is orally administered to the animals.

10. The process of claim 9 wherein the animal is a ruminant.

11. The process of claim 10 wherein the ruminant is a dairy cow or beef cattle.

12. The process of claim 11 wherein the cow is a lactating dairy cow.

13. The composition of claim 3 wherein $R^3$ is H.

14. The composition of claim 13 wherein AA comprises at least one methionine α-amino acid residue.

15. The composition of claim 1 wherein AA comprises at least one amino acid residue selected from the group consisting of methionine and lysine.

16. The composition of claim 14 wherein —(AA)$_n$ comprises at least one methionine residue and at least one lysine residue.

17. The composition of claim 16 wherein the ratio of lysine to methionine residues contained in AA is about 3:1.

18. The composition of claim 1 wherein the α-amino acid residues are selected from residues of one or more essential α-amino acids.

19. The composition of claim 18 wherein the essential α-amino acids are selected from the group consisting of isoleucine, phenylalanine, leucine, lysine, methionine, threonine, tryptophan, histidine and valine.

20. A composition comprising

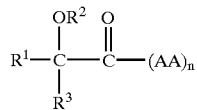

wherein

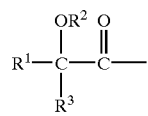

is the residue of an α-hydroxy acid analog of a naturally occurring α-amino acid and each AA is an amino acid residue selected from the group consisting of asparagine, proline, cysteine, methionine, tryptophan, tyrosine, aspartic acid, and histidine, wherein $R^1$ is hydrogen, hydrocarbyl or substituted hydrocarbyl, $R^2$ is hydrogen, hydrocarbyl, substituted hydrocarbyl, or is another hydroxy protecting group selected from the group consisting of tert-butyldimethylsilyl (TBS), tert-butyldiphenylsilyl (TBPS), triethylsilyl (TES), trimethylsilyl (TMS), and triisopropylsilyl (TIPS), $R^3$ is hydrogen, hydrocarbyl or substituted hydrocarbyl, and n is 1, wherein said $R^2$ substituted hydrocarbyl moieties are hydrocarbyl moieties that are comprised of one or more substituted atoms other than carbon, wherein the substituted atoms are selected from the group consisting of oxygen, silicon, phosphorus, boron, sulfur, and halogen atoms.

21. The composition of claim 20, wherein AA is an essential amino acid residue selected from the group consisting of methionine, tryptophan, and histidine.

22. The composition of claim 1, wherein $R^2$ is a hydrocarbyl or substituted hydrocarbyl, wherein the hydrocarbyl is selected from the group consisting of benzyl (PhCH$_2$—), triphenyl methyl (Trityl, Tr), and tert-butyl (t-Bu), and wherein the substituted hydrocarbyl is selected from the group consisting of acetyl (Ac), 1-ethoxyethyl (EE), methoxymethyl (MOM), (methoxyethoxy)methyl (MEM), (p-methoxyphenyl)methoxymethyl (MPM), tert-butoxycarbonyl (Boc), tetrahydropyranyl (THP), 2-methoxy-2-methylpropyl, benzyloxycarbonyl (Cbz), trichloroacetyl (OCCCl$_3$), and benzyloxymethyl (BOM).

* * * * *